(12) United States Patent
Kumar et al.

(10) Patent No.: US 7,553,619 B2
(45) Date of Patent: *Jun. 30, 2009

(54) DETECTION METHOD USING DISSOCIATED ROLLING CIRCLE AMPLIFICATION

(75) Inventors: Gyanendra Kumar, Guilford, CT (US); Patricio Abarzua, West Caldwell, NJ (US); Michael Egholm, Woodbridge, CT (US)

(73) Assignee: Qiagen GmbH, Hilden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/072,666

(22) Filed: Feb. 8, 2002

(65) Prior Publication Data

US 2003/0152932 A1 Aug. 14, 2003

(51) Int. Cl.
C12Q 1/68 (2006.01)
C07H 21/04 (2006.01)
(52) U.S. Cl. .................. 435/6; 435/91.2; 536/24.33
(58) Field of Classification Search .......... 435/6, 435/91.1, 91.2, 91.21; 536/23.1, 24.31, 24.33, 536/24.34, 24.32
See application file for complete search history.

(56) References Cited

U.S. PATENT DOCUMENTS

| | | | |
|---|---|---|---|
| 2,264,423 A | 12/1941 | Wingenroth | |
| 3,687,808 A | 8/1972 | Merigan et al. | 435/91.3 |
| 3,921,105 A | 11/1975 | Brgetz | |
| 3,983,421 A | 9/1976 | Yogore | |
| 4,469,863 A | 9/1984 | Ts'o | |
| 4,476,301 A | 10/1984 | Imbach et al. | |
| 4,748,111 A | 5/1988 | Dattagupat et al. | |
| 4,845,205 A | 7/1989 | Huynh Dinh et al. | |
| 4,883,750 A | 11/1989 | Whiteley et al. | |
| 4,965,188 A | 10/1990 | Walker et al. | |
| 4,981,957 A | 1/1991 | Lebleu et al. | |
| 4,984,957 A | 1/1991 | Noguchi et al. | |
| 4,994,373 A | 2/1991 | Stavrianopoulos et al. | |
| 5,001,050 A | 3/1991 | Blanco et al. | 435/5 |
| 5,023,243 A | 6/1991 | Tullis | |
| 5,034,506 A | 7/1991 | Summerton et al. | |
| 5,043,272 A | 8/1991 | Hartley | |
| 5,118,800 A | 6/1992 | Smith et al. | |
| 5,130,238 A | 7/1992 | Malek et al. | |
| 5,130,302 A | 7/1992 | Spielvogel et al. | |
| 5,134,066 A | 7/1992 | Rogers et al. | |
| 5,166,315 A | 11/1992 | Summerton et al. | |
| 5,175,273 A | 12/1992 | Bischofberger et al. | |
| 5,177,196 A | 1/1993 | Meyer, Jr. et al. | |
| 5,185,444 A | 2/1993 | Summerton et al. | |
| 5,188,897 A | 2/1993 | Suhadolnik et al. | |
| 5,198,543 A | 3/1993 | Blanco et al. | 536/23.2 |
| 5,214,134 A | 5/1993 | Weis et al. | |
| 5,216,141 A | 6/1993 | Benner | |
| 5,235,033 A | 8/1993 | Summerton et al. | |
| 5,242,794 A | 9/1993 | Normal et al. | |
| 5,264,423 A | 11/1993 | Cohen et al. | |
| 5,264,562 A | 11/1993 | Matteucci | |
| 5,264,564 A | 11/1993 | Matteucci | |
| 5,264,567 A | 11/1993 | Numata et al. | |
| 5,273,638 A | 12/1993 | Konrad et al. | |
| 5,276,019 A | 1/1994 | Cohen et al. | |
| 5,278,302 A | 1/1994 | Caruthers et al. | |
| 5,286,717 A | 2/1994 | Cohen et al. | |
| 5,319,080 A | 6/1994 | Leumann | |
| 5,321,131 A | 6/1994 | Agrawal et al. | |
| 5,328,824 A | 7/1994 | Ward et al. | |
| 5,354,668 A | 10/1994 | Auerbach | |
| 5,359,044 A | 10/1994 | Cook et al. | |
| 5,367,066 A | 11/1994 | Urdea et al. | |
| 5,367,069 A | 11/1994 | Beck et al. | |
| 5,393,878 A | 2/1995 | Leumann | |
| 5,399,676 A | 3/1995 | Froehler | |
| 5,405,938 A | 4/1995 | Summerton et al. | |

(Continued)

FOREIGN PATENT DOCUMENTS

AU 649066 5/1994

(Continued)

OTHER PUBLICATIONS

Baner et al. Signal amplification of padlock probes by rolling circle replication. Nucleic Acids Res., vol. 26 (22), p. 5073-5078, 1998.*

(Continued)

*Primary Examiner*—Suryaprabha Chunduru
(74) *Attorney, Agent, or Firm*—Ballard Spahr Andrews & Ingersoll, LLP

(57) ABSTRACT

Disclosed are compositions and methods for detecting small quantities of analytes such as proteins and peptides. The method involves associating a DNA circle with the analyte and subsequent release and rolling circle replication of the circular DNA molecule. In the method, an amplification target circle is associated with analytes using a conjugate of the circle and a specific binding molecule that is specific for the analyte to be detected. Amplification target circles not associated with the proteins are removed, the amplification target circles that are associated with the proteins are decoupled from the specific binding molecule and amplified by rolling circle amplification. The amplification is isothermic and can result in the production of a large amount of nucleic acid from each primer. The amplified DNA serves as a readily detectable signal for the analytes.

136 Claims, 9 Drawing Sheets

U.S. PATENT DOCUMENTS

| | | | |
|---|---|---|---|
| 5,405,939 A | 4/1995 | Suhadolnik et al. | |
| 5,409,818 A | 4/1995 | Davey et al. | |
| 5,412,087 A | 5/1995 | McGall et al. | |
| 5,427,930 A | 6/1995 | Birkenmeyer et al. | |
| 5,429,807 A | 7/1995 | Matson et al. | |
| 5,432,272 A | 7/1995 | Benner | |
| 5,434,257 A | 7/1995 | Matteucci et al. | |
| 5,443,986 A | 8/1995 | Haughland et al. | |
| 5,446,137 A | 8/1995 | Maag et al. | |
| 5,451,067 A | 9/1995 | Pieper | |
| 5,451,203 A | 9/1995 | Lamb | |
| 5,453,496 A | 9/1995 | Caruthers et al. | |
| 5,455,166 A | 10/1995 | Walker | |
| 5,455,233 A | 10/1995 | Spielvogel et al. | |
| 5,457,187 A | 10/1995 | Gmeiner et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,427 A | 12/1995 | Fujima | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,502,177 A | 3/1996 | Matteucci et al. | |
| 5,510,270 A | 4/1996 | Fodor et al. | |
| 5,514,785 A | 5/1996 | Van Ness et al. | |
| 5,516,134 A | 5/1996 | Crawford et al. | |
| 5,516,663 A | 5/1996 | Backman et al. | |
| 5,519,126 A | 5/1996 | Hecht | |
| 5,519,134 A | 5/1996 | Acevedo et al. | |
| 5,521,065 A | 5/1996 | Whiteley et al. | |
| 5,523,204 A | 6/1996 | Singer et al. | |
| 5,525,711 A | 6/1996 | Hawkins et al. | |
| 5,536,821 A | 7/1996 | Agrawal et al. | |
| 5,538,871 A | 7/1996 | Nuovo et al. | |
| 5,539,082 A | 7/1996 | Nielsen et al. | 530/300 |
| 5,541,306 A | 7/1996 | Agrawal et al. | |
| 5,541,307 A | 7/1996 | Cook et al. | |
| 5,547,843 A | 8/1996 | Studier et al. | |
| 5,550,111 A | 8/1996 | Suhadolnik et al. | |
| 5,552,540 A | 9/1996 | Haralambidis | |
| 5,556,772 A | 9/1996 | Sorge et al. | |
| 5,561,225 A | 10/1996 | Maddry et al. | |
| 5,563,037 A | 10/1996 | Sutherland et al. | 435/6 |
| 5,563,253 A | 10/1996 | Agrawal et al. | |
| 5,563,912 A | 10/1996 | Yasunaga et al. | |
| 5,567,811 A | 10/1996 | Misiura et al. | |
| 5,571,799 A | 11/1996 | Tkachuk et al. | |
| 5,576,427 A | 11/1996 | Cook et al. | |
| 5,587,361 A | 12/1996 | Cook et al. | |
| 5,587,469 A | 12/1996 | Cook et al. | |
| 5,591,609 A | 1/1997 | Auerbach | |
| 5,591,722 A | 1/1997 | Montgomery et al. | |
| 5,594,121 A | 1/1997 | Froehler et al. | |
| 5,596,086 A | 1/1997 | Matteucci et al. | |
| 5,596,091 A | 1/1997 | Switzer et al. | |
| 5,597,909 A | 1/1997 | Urdea et al. | |
| 5,599,921 A | 2/1997 | Sorge et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,389 A | 3/1997 | Auerbach | |
| 5,614,390 A | 3/1997 | McCaslin et al. | |
| 5,614,617 A | 3/1997 | Cook et al. | |
| 5,618,704 A | 4/1997 | Sanghui et al. | |
| 5,623,070 A | 4/1997 | Cook et al. | |
| 5,625,050 A | 4/1997 | Beaton et al. | |
| 5,627,053 A | 5/1997 | Usman et al. | |
| 5,629,158 A | 5/1997 | Uhlen | |
| 5,629,179 A | 5/1997 | Mierendorf et al. | |
| 5,633,360 A | 5/1997 | Bischofberger et al. | |
| 5,639,873 A | 6/1997 | Barascut et al. | |
| 5,646,265 A | 7/1997 | McGee | |
| 5,648,245 A | 7/1997 | Fire et al. | |
| 5,658,873 A | 8/1997 | Bentsch-Frank et al. | |
| 5,663,312 A | 9/1997 | Chaturvedula | |
| 5,670,633 A | 9/1997 | Cook et al. | |
| 5,677,437 A | 10/1997 | Teng et al. | |
| 5,677,439 A | 10/1997 | Wies et al. | |
| 5,681,941 A | 10/1997 | Cook et al. | |
| 5,700,920 A | 12/1997 | Altmann et al. | |
| 5,710,028 A | 1/1998 | Eyal et al. | |
| 5,714,320 A | 2/1998 | Kool | |
| 5,714,331 A | 2/1998 | Buchardt et al. | 435/6 |
| 5,719,262 A | 2/1998 | Buchardt et al. | 530/300 |
| 5,728,526 A | 3/1998 | George et al. | |
| 5,733,733 A | 3/1998 | Auerbach | |
| 5,766,891 A | 6/1998 | Shuman | |
| 5,795,714 A | 8/1998 | Cantor et al. | |
| 5,821,084 A | 10/1998 | Olmsted et al. | |
| 5,854,033 A * | 12/1998 | Lizardi | 435/91.2 |
| 5,854,053 A | 12/1998 | Donovan et al. | |
| 5,866,329 A | 2/1999 | Demetriou et al. | |
| 5,866,336 A | 2/1999 | Nazarenko et al. | |
| 5,871,921 A | 2/1999 | Landgren et al. | |
| 5,874,260 A | 2/1999 | Cleuziat et al. | |
| 5,876,924 A | 3/1999 | Zhang et al. | |
| 5,909,132 A | 6/1999 | Trofimenkoff et al. | |
| 5,925,517 A | 7/1999 | Tyagi et al. | |
| 5,942,391 A | 8/1999 | Zhang et al. | |
| 5,985,639 A | 11/1999 | Christianson et al. | |
| 6,008,373 A | 12/1999 | Waggoner et al. | |
| 6,017,703 A | 1/2000 | Kinders et al. | |
| 6,033,881 A | 3/2000 | Himmler et al. | |
| 6,037,130 A | 3/2000 | Tyagi et al. | |
| 6,054,274 A | 4/2000 | Sampson et al. | |
| 6,057,105 A | 5/2000 | Hoon et al. | |
| 6,077,668 A | 6/2000 | Kool | |
| 6,077,674 A | 6/2000 | Schleifer et al. | |
| 6,096,880 A | 8/2000 | Kool | |
| 6,117,635 A | 9/2000 | Nazarenko et al. | |
| 6,124,120 A | 9/2000 | Lizardi | |
| 6,132,728 A | 10/2000 | Beachy et al. | |
| 6,143,495 A | 11/2000 | Lizardi et al. | 435/6 |
| 6,183,960 B1 | 2/2001 | Lizardi | 435/6 |
| 6,203,984 B1 | 3/2001 | Hu et al. | |
| 6,210,884 B1 | 4/2001 | Lizardi | 435/6 |
| 6,214,587 B1 | 4/2001 | Dattagupta et al. | |
| 6,221,603 B1 | 4/2001 | Mahtani | |
| 6,235,502 B1 | 5/2001 | Weissman et al. | |
| 6,248,535 B1 | 6/2001 | Dandenberg et al. | |
| 6,255,082 B1 | 7/2001 | Lizardi et al. | |
| 6,274,320 B1 | 8/2001 | Rothberg et al. | |
| 6,277,607 B1 | 8/2001 | Tyagi et al. | |
| 6,280,949 B1 | 8/2001 | Lizardi | |
| 6,287,768 B1 | 9/2001 | Chenchik et al. | |
| 6,287,776 B1 | 9/2001 | Hefti | |
| 6,287,824 B1 | 9/2001 | Lizardi | |
| 6,288,220 B1 | 9/2001 | Kambara et al. | |
| 6,291,187 B1 | 9/2001 | Kingsmore et al. | |
| 6,291,193 B1 | 9/2001 | Khodadoust | |
| 6,291,669 B1 | 9/2001 | Kwiatkowski et al. | 536/25.3 |
| 6,294,664 B1 | 9/2001 | Ravikumar et al. | 536/25.3 |
| 6,297,006 B1 | 10/2001 | Drmanac et al. | |
| 6,312,902 B1 | 11/2001 | Shultz et al. | |
| 6,316,229 B1 | 11/2001 | Lizardi et al. | |
| 6,323,009 B1 | 11/2001 | Lasken et al. | |
| 6,329,150 B1 | 12/2001 | Lizardi et al. | 435/6 |
| 6,344,329 B1 | 2/2002 | Lizardi | 435/6 |
| 6,355,431 B1 | 3/2002 | Chee et al. | |
| 6,365,729 B1 | 4/2002 | Tyagi et al. | |
| 6,368,801 B1 | 4/2002 | Faruqi | |
| 6,403,319 B1 * | 6/2002 | Lizardi et al. | 435/6 |

| | | | | | | |
|---|---|---|---|---|---|---|
| 6,440,707 | B1 | 8/2002 | Kwok et al. | WO | WO 92/01813 | 2/1992 |
| 6,458,544 | B1 | 10/2002 | Miller | WO | WO 94/16108 | 7/1994 |
| 6,472,185 | B2 | 10/2002 | McCasky Feazel et al. | WO | WO 94/24312 | 10/1994 |
| 6,475,736 | B1 | 11/2002 | Stanton | WO | WO 95/03430 | 2/1995 |
| 6,479,242 | B1 | 11/2002 | Guo et al. | WO | WO 95/03432 | 2/1995 |
| 6,479,244 | B1 | 11/2002 | Belouchi et al. | WO | WO 95/22623 | 8/1995 |
| 6,498,023 | B1 * | 12/2002 | Abarzua ............... 435/91.2 | WO | WO 95/25180 | 9/1995 |
| 6,531,283 | B1 * | 3/2003 | Kingsmore et al. ........... 435/6 | WO | WO 95/35390 | 12/1995 |
| 6,573,051 | B2 | 6/2003 | Alsmadi et al. | WO | WO 96/33207 | 10/1996 |
| 6,617,137 | B2 | 9/2003 | Dean et al. | WO | WO 97/17076 | 5/1997 |
| 6,632,609 | B2 | 10/2003 | Lizardi | WO | WO 97/17471 | 5/1997 |
| 6,635,425 | B2 | 10/2003 | Bandaru et al. | WO | WO 97/19193 | 5/1997 |
| 6,670,126 | B2 | 12/2003 | Kingsmore et al. | WO | WO 97/20948 | 6/1997 |
| 6,686,157 | B2 | 2/2004 | Ward et al. | WO | WO 97/42346 | 11/1997 |
| 6,703,228 | B1 | 3/2004 | Landers et al. | WO | WO 98/04746 | 2/1998 |
| 6,703,885 | B1 | 3/2004 | Fan et al. | WO | WO 99/18241 | 4/1999 |
| 6,713,257 | B2 | 3/2004 | Shoemaker et al. | WO | WO 99/31276 | 6/1999 |
| 6,777,183 | B2 | 8/2004 | Abarzua | WO | WO 00/04193 | 1/2000 |
| 6,797,474 | B2 * | 9/2004 | Lizardi ..................... 435/6 | WO | WO 00/15779 | 3/2000 |
| 6,811,986 | B2 | 11/2004 | Bandaru et al. | WO | WO 00/36141 | 6/2000 |
| 6,830,884 | B1 | 12/2004 | Hafner et al. | WO | WO 00/71562 A | 11/2000 |
| 6,861,222 | B2 | 3/2005 | Ward et al. | WO | WO 01/40516 | 6/2001 |
| 6,921,642 | B2 * | 7/2005 | Kingsmore et al. ........... 435/6 | WO | WO 01/61037 | 8/2001 |
| 6,977,153 | B2 | 12/2005 | Kumar et al. | WO | WO 01/64952 | 9/2001 |
| 7,041,480 | B2 | 5/2006 | Abarzua | WO | WO 01/77390 | 10/2001 |
| 2001/0041340 | A1 | 11/2001 | Kingsmore et al. | WO | WO 01/79420 | 10/2001 |
| 2002/0009716 | A1 | 1/2002 | Abarzua | WO | WO 01/88190 | 11/2001 |
| 2002/0119465 | A1 | 8/2002 | Zhao et al. | WO | WO 01/97616 | 12/2001 |
| 2002/0120409 | A1 | 8/2002 | Cao et al. | WO | WO 02/00934 | 1/2002 |
| 2002/0192649 | A1 | 12/2002 | Lizardi | WO | WO 02/02792 | 1/2002 |
| 2002/0192658 | A1 | 12/2002 | Ward et al. | WO | WO 02/053780 | 7/2002 |
| 2002/0197694 | A1 | 12/2002 | Shao | WO | WO 02/077256 | 10/2002 |
| 2003/0008313 | A1 | 1/2003 | Whitshire | WO | WO 02/103058 | 12/2002 |
| 2003/0022167 | A1 | 1/2003 | Alsmadi et al. | WO | WO 03/008538 | 1/2003 |
| 2003/0032024 | A1 | 2/2003 | Lizardi | WO | WO 2004/061119 | 7/2004 |
| 2003/0044794 | A1 | 3/2003 | Bandaru et al. | | | |
| 2003/0108902 | A1 | 6/2003 | Abarzua | | | |
| 2003/0143613 | A1 | 7/2003 | Kingsmore et al. | | | |
| 2003/0152932 | A1 | 8/2003 | Kumar et al. | | | |
| 2003/0165948 | A1 | 9/2003 | Alsmadi et al. | | | |
| 2003/0175788 | A1 | 9/2003 | Alsmadi et al. | | | |
| 2003/0207267 | A1 | 11/2003 | Lasken et al. | | | |
| 2003/0207323 | A1 | 11/2003 | Bandaru et al. | | | |
| 2003/0235849 | A1 | 12/2003 | Lizardi | | | |
| 2004/0091857 | A1 | 5/2004 | Nallur et al. | | | |
| 2004/0121338 | A1 | 6/2004 | Alsmadi et al. | | | |
| 2004/0126770 | A1 | 7/2004 | Kumar et al. | | | |
| 2004/0191784 | A1 | 9/2004 | Abarzua et al. | | | |
| 2004/0248103 | A1 | 12/2004 | Feaver et al. | | | |
| 2004/0265897 | A1 | 12/2004 | Lizardi | | | |
| 2005/0079523 | A1 | 4/2005 | Hafner et al. | | | |
| 2006/0166227 | A1 | 7/2006 | Kingsmore et al. | | | |
| 2006/0188892 | A1 | 8/2006 | Kumar et al. | | | |

FOREIGN PATENT DOCUMENTS

| | | |
|---|---|---|
| AU | 714486 | 4/2000 |
| EP | 0 070 685 B1 | 7/1982 |
| EP | 0 128 332 | 12/1984 |
| EP | 0 356 021 | 2/1990 |
| EP | 0 379 369 | 7/1990 |
| EP | 0 439 182 | 7/1991 |
| EP | 0 466 520 | 1/1992 |
| EP | 0 505 012 | 9/1992 |
| EP | 0 667 393 | 8/1995 |
| EP | 0 678 582 | 10/1995 |
| EP | 0 745 690 A | 12/1996 |
| EP | 0 756 009 A2 | 1/1997 |
| GB | 2332516 | 6/1999 |
| JP | 4262799 | 9/1992 |
| JP | 4304900 | 10/1992 |
| JP | 5146299 | 6/1993 |
| WO | WO 91/08307 | 6/1991 |

OTHER PUBLICATIONS

AAAI Board of Directors. Measurement of specific and nonspecific IgG$_4$ levels as diagnostic and prognostic tests for clinical allergy. *J. Allergy Clin. Immunol.* 95:652-654 (1995).

Aliotta et al. Thermostable *Bst* DNA polymerase I lacks a 3'→ 5' proofreading exonuclease activity. *Genet. Anal* (Netherlands) 12:185-195 (1996).

Anderson and Seilhamer. A comparison of selected mRNA and protein abundances in human liver. *Electrophoresis* 18:533-537.

Beaucage et al. Deoxynucleoside Phosphoramidites-A New Class of Key Intermediates For Deoxypolynucleotide Synthesis. *Tetrahedron Lett.* 22:1850 (1981).

Boehmer and Lehman. Herpes Simplex Virus Type 1 ICP8: Helix-Destabilizing Properties. *J. Virol.* 67(2)711-715 (1993).

Brush. Dye Hard: Protein Gel Staining Products. *The Scientist* 12:16-22 (1998).

Chang. The pharmacological basis of anti-IgE therapy. *Nat. Biotech.* 18:157-162 (2000).

Chatterjee et al. Cloning and overexpression of the gene encoding bacteriophage T5 DNA polymerase. *Gene* 97:13-19 (1991).

Ekins. Ligand assays: from electrophoresis to miniaturized microarrays. *Clin. Chem.* 44(9):4015-2030 (1998).

Englisch et al. Chemically Modified Olinucleotides as probes and Inhibitors. *Angewandte Chemie*, International Edition 30(6):613-722 (1991).

Ernst et al. Cyanine Dye Labeling Reagents for Sulfhydryl Groups. *Cytometry* 10:3-10 (1989).

Fields et al. How many genes in the human genome. *Nat. Genet.* 7:345-346 (1994).

Fire and Xu. Rolling replication of short DNA circles. *Proc. Natl. Acad. Sci. USA* 92:4641-4645 (1995).

Fleischmann et al. Whole-Genome Random Sequencing and Assembly of *Haemophilus influenzae* Rd. *Science* 269:469 (1995).

Guo et al. Direct fluorescence analysis of genetic polymorphisms by hybridization with oligonucleotides arrays on glass support. *Nucl. Acids Res.* 22(24):5456-5465 (1994).

Gygi et al. Correlation between Protein and mRNA Abunance in Yeast. *Mol. Cell. Biol.* 19(3):1720-1730 (1999).

Hall et al., Nucleotide. Part XLI. Mixed Anhydrides an Intermediates in the Synthesis of Dinucleotide Phosphates. *J. Chem. Soc.* 3291-3296 (1957).

Hendrickson et al. High sensitivity multianalyte immunoassay using covalent DNA-labeled antibodies and polymerase chain reaction. *Nucl. Acids Res.* 23(3):522-529 (1995).

Henegariu et al. Custom flouscent-nucleotide synthesis as an alternative method foe nucleic acid labeling. *Nat. Biotech.* 18:345-348 (2000).

Hoy and Schimke. Bromodeoxyuridine/DNA analysis of replication in CHO cells after exposure to UV light. *Mutation Res.* 290:217-230 (1993).

Humphrey-Smith and Blackstock. Proteome Analysis: Genomics via the Output Rather Than the Input Code. *J. Protein. Chem.* 16(5):537-544 (1997).

Itakura et al. Synthesis and Using of Synthetic Oligonucleotides. *Ann. Rev. Biochem.* 53:323-356 (1984).

Iyer et al. 3-$H$-1,2-Benzodithiole-3-one 1, 1-Dioxide as an Improved Sulfuring Reagent in the Soild-Phase Synthesis of Oligodeoyribonucleoside Phosphorothioates. *J. Am. Chem Soc.* 112:1253-1254 (1990).

Jacobsen et al. The N-Terminal Amino-Acid Sequences of DNA Polymerase I from *Escherichia coli* and of the large and the Small Fragments Obtained by a Llimited Proteolysis. *Eur. J. Biochem.* 45:623-627 (1974).

Johnstone and Thorpe. *Immunochemistry In Practice* (Blackwell Scientific Publications) Oxford, England pp. 209-216 and 241-242 (1987).

Jung et al. Bacteriophage PRD1 DNA Polymerase: Evolution of DNA polymerases. *Proc. Natl. Acad. Sci. USA* 84:8287 (1987).

Kaboord and Bankovic. Accesory proteins function as matchmakers in the assembly of the T4 DNA polymerase holoenzyme. *Curr. Biol.* 5(2):149-157 (1995).

Kerkhof. A comparison of Substrates for Quantifying the Signal from a Nonradiolabeled DNA Probe. *Anal. Biochem.* 205:359-364 (1992).

Khrapko et al. Hybridization of DNA with Oligonucleotides Immobilized in Gel: A Convenient Method for detecting Single Base Substitutions. *Mol. Biol.* (Mosk) (USSR) 25:718-730 (1991).

Kong et al. Characterization of a DNA Polymerase from the Hyperthermophile Archaea *Thermococcus litoralis. J. Biol. Chem.* 268(3):1965-1975 (1993).

Langer et al. Enzymatic synthesis of biotin-labeled polynucleotides: Novel nucleic acid affinity probes. *Proc. Natl. Acad. Sci. USA* 78(11):6633-6637 (1981).

Lesnick and Freier. Relative Thermodynamic Stability of DNA, RNA, and DNA:RNA Hybrid Duplexes: Relationship with Base Composition and Structure. *Biochemistry* 34:10807-10815 (1995).

Letsinger et al. Use of a Stilbenedicarboxamide Bridge in Stabilizing, Monitoring, and Photochemically Altering Folded Conformations of Oligonucleotides. *J. Am. Chem. Soc.* 9:3655 (1976).

Lizardi et al. Mutation detection and single-molecule counting using isothermal rolling-circle amplification. *Nat. Genet.* 19:225-232 (1998).

Matsumoto et al. Primary structure of bacteriophage M2 DNA polymerasee: consevsed segments within protein briming DNA polymerases and DNA polymerase I of *Escherichia coli*, Gene 84:247 (1989).

Matteucci et al. Synthesis of Deoxyoligonucleotides on a Polymer Support. *J. Am. Chem. Soc.* 103:3185 (1981).

McGraw et al. Sequence-Dependent Oligonucleotide-Target Duplex Stabilities: Rules from Empirical Studies with a Set of Twenty-Mers. *Biotechniques* 8(6):674-678 (1990).

Mujumdar et al. Cyanine Dye Labeling Reagents Containing Isothiocyanate Groups. *Cytometry* 10:11-19 (1989).

Narang et al. Chemical Synthesis of Deoxyoligonucleatides by the Modified Triester Method. *Meth. Enzymol.* 65:610-620 (1980).

Neilsen et al. Peptide Nucleic Acid (PNA). A DNA Mimic with a Peptide Backbone. *Bioconjug. Chem.* 5:3-7 (1994).

Neilsen. Sequence-Selective Recognition of DNA by Strand Displacement with a Thymine-Substituted Polymide. *Science* 254:1497-1500 (1991).

Oda et al. Accurate quantitation of protein expression and site-specific phosphorylation. *Proc. Natl. Acad. Sci. USA* 96:6591-6596 (1999).

Patton et al. Components of the Protein Synthesis and Folding Machinery Are Induced in Vascular Smooth Muscle Cells by Hypertrophic and Hyperplastic Agents. *J. Biol. Chem.* 270(36):21404-21410 (1995).

Patton. Proteome analysis II. Protein subcellular redistribution: linking physiology to genomics via the proteome and separationtechnologies involved. *J. Chromatogr.* 722:203-223 (1999).

Patton. Making Blind Robots See: The Synergy Between Flourescent Dyes and Imaging Devices in Automated Proteomics. *Biotechniques* 28:944-957 (2000).

Pease et al. Light-generate oligonucleotide arrays for rapid DNA sequence analysis. *Proc. Natl. Acad. Sci. USA* 91(11):5022-5026 (1994).

Pless et al. Solid support synthesis of oligothymidylates using phosphorochlorides and 1-alkylimidazoles. *Nucl. Acids Res.* 2(6):773-786 (1975).

Rigler and Ramano. Differences in the Mechanism of Mechanism of Stimulation of T7 DNA Polymease by Two Binding Modes of *Eschericha coli* Single-stranded DNA-binding Protein. *J. Biol. Chem.* 270(15):8910-8919 (1995).

Rychlik et al. Optimization of the annealing temperature for DNA amplification in vivo. *Nucl. Acids Res.* 18(21):6409-6412 (1990).

Sambrook et al. *Molecular Cloning: A Laboratory Manual*, 2nd Ed. (Cold Spring Harbor Laboratory Press. Cold spring Harbor, N.Y.) Chapter 5-6 (1989).

Sanghvi. Heterocyclic Base Modifications in Nucleic Acids and Their Applications in Antisense Oligonucleotides. Antisense Research and Applications. (Crooke and Lebleu ed CRC Press) Chap. 15-16 pp. 273-301 (1993).

Sano et al. Detection of heavy methylation in human repetitive DNA subsets by a monoclonal antibody against 5- methylcytosine. *Biochim. Biophys. Acta.* 951:157-165 (1988).

Schena and Davis, Genes, genomes, and chipe. DNA Microarrays: A Practical Approach. Oxford University Press, New York pp. 1-16 (1999).

Siegel et al. A Novel DNA Helicase from Calf Thymus. *J. Biol. Chem.* 267(19):13629-13635 (1992).

Skaliter and Lehman. Rolling circle DNA replication in vitro by a complex of herpes simplex virus type 1-encoded enzymes. *Proc. Natl. Sci. USA* 91(22):10665-10669 (1994).

Speicher et al. Karyotying human chromosomes by combinatorial multi-flour FISH. *Nature Genet.* 12:368-375 (1996).

Stimpson et al. Real-time detection of DNA hybridization and melting on oligonucleotide arrays by using optical wave guides. *Proc. Natl. Acad. Sci. USA* 92:6379-6383 (1995).

Tsurumi et al. Functional Interaction between Epstein-Barr Virus DNA Polymerase Catalytic Subunit and Its Accessory Subunit in Vitro. *J. Virol.* 67(12)7648-7653 (1993).

Tyagi and Kramer. Molecular Beacons: Probes that Flouresce upon Hybridization. *Nat. Biotech.* 14:303-308 (1996).

Villemain and Giedroc. The N-Terminal B-Domain of T4 Gene 32 Protein Modulates the Lifetime of Cooperatively Bound Gp32-ss Nucleic Acid Complexes. *Biochemistry* 35:14395-14404 (1996).

Waggoner. Covalent Labeling of Proteins and Nucleic Acids with Fluorophores. *Meth. Enzymol.* 246:362-373 (1995).

Walker and Lin. Detection of Mycobacterium tuberculosis DNA with thermophilic strand displacement amplication and Fluorescence polarization. *Clin. Chem.* 42(10):1604-1608 (1996).

Wang et al. Large-Scale Identification, Mapping, and Genotyping of Single-Nucleotide Polymorphisms in the Human Genome. *Science* 280:1077 (1998).

Wansick et al. Fluorescent Labeling of Nascent RNA Reveals Transcription by RNA Polymerase II in Domains Scattered Throughout the Nucleus. *J. Cell. Biol.* 122(2):283-293 (1993).

Wirth and Romano. Stainig methods in gel electrophoresis, including the use of multiple detection methods. *J. Chromatogr* 698:123-143 (1995).

Yu et al. Cyanine dye dUTP analogs for enzymatic labeling of DNA probes. *Nucl. Acids Res.* 22(15):3226-3232 (1994).

Zhu and Ito. Purification and characterization of PRD1 DNA polymerase. *Biochim. Biophys. Acta.* 1219:267-276 (1994).
Zijderveld and van der Vliet. Helix-Destabilizing Properties of the Adenovirus DNA-Binding Protein. *J. Virol.* 68(2):1158-1164 (1994).
Loakes et al. "5-Nitroidole as a universal base analogue" Nucleic Acids Res. 1994, 22(20):45039-4043.
Baner et al. Signal Amplification of Padlock Probes by Rolling Circle Replication *Nucleic Acids Research, Oxford University Press*, Surrey, GB 26(22):5073-5078 (1998), XP002112357.
Gusev et al., Rolling Circle Amplfiication: A New Approach to Increase Sensitivity for Immunohistochemistry and Flow Cytometry *American Journal of Pathology* 159(1): 63-69 (Jul. 2001).
Mullenix et al. Allergen-specific IgE Detection on Microarrays Using Rolling Circle Amplification: Correlation with in Vitro Assays for Serum IGE *Clinical Chemistry* 47(10):1926-1929 (2001).
Nuovo et al. In Situ Amplification Using Universal Energy Transfer-Labeled Primers *Journal of Histochemistry and Cytochemistry, Histochemical Society*, New York, New York 43(3):273-279 (1999), XP008002684.
Schweitzer et al. Multiplexed Protein Profiling on Microarrays by Rolling-Circle Amplification *Nature Biotechnology* 20:359-365 (2002).
Schweitzer et al. Immunoassays with Rolling Circle DNA Amplification: A Versatile Platform for Ultrasensitive Antigen Detection *PNAS* 97(18):10113-10119 (2000).
Tyagia et al. Molecular Beacons: Probes that Fluoresce upon Hybridization, *Nature Biotechnology*, 14:303-308 (Mar. 1996), XP000196024.
Alves et al. Dot blot detection of point mutations with adjacently hybridising synthetic oligonucleotide probes. *Nucleic Acids Res.* 16(17):8723 (1988).
Arnold et al. Assay formats involving acridinium-ester-labeled DNA probes. *Clin Chem.* 35(8):1588-1594 (1989).
Ausubel et al. *Current Protocols in Molecular Biology*. John Wiley & Sons. 1:1.6.1-1.6.6 (1988).
Barany. Genetic disease detection and DNA amplification using cloned thermostable ligase. *Proc Natl Acad Sci USA.* 88:189-193 (1991).
Barbato et al. Solid Phase Syntheses of Cyclic Oligodeoxyribonucleotides. *Tetrahedron Letters.* 28(46):5727-2728 (1987).
Bertina et al. Mutation in blood coagulation factor V associated with resistance to activated protein C. *Nature.* 369:64-67 (1994).
Birkenmeyer et al. DNA probe amplification methods. *Journal of Virological Methods.* 35:117-126 (1991).
Blanco et al. Characterization and purification of a phage $\Phi$29-encoded DNA polymerase required for the initiation of replication. *Proc Natl Acad Sci USA.* 81:5325-5329 (1984).
Blanco et al. Highly efficient DNA synthesis by the phage $\Phi$29 DNA polymerase. *Journal of Biological Chemistry.* 264(15):8935-8940 (1989).
Blanco et al. Terminal protein-primed DNA amplification. *Proc Natl Acad Sci USA.* 91:12198-12202 (1994).
Bonnet et al. Thermodynamic basis of the enhanced specificity of structured DNA probes. *Proc Natl Acad Sci USA.* 96(11):6171-6176 (1999).
Broude et al. Enhanced DNA sequencing by hybridization. *Proc Natl Acad Sci USA.* 91:3072-3076 (1994).
Bryant et al. Phosphorothioate substrates for T4 RNA ligase. *Biochemistry.* 21(23):5877-5885 (1982).
Burgess et al. A new photolabile protecting group for nucleotides. *Abstracts of Papers, Part 2.; 211th ACS National Meeting, American Chemical Society.* New Orleans, LA, Mar. 24-28, 1996.
Butler et al. Bacteriophage SP6-specific RNA polymerase. *Journal of Biological Chemistry.* 257(10):5772-5778 (1982).
Capobianco et al. One pot solution synthesis of cyclic oligodeoxyribonucleotides. *Nucleic Acids Research.* 18(9):2661-2669 (1990).
Chetverina et al. Cloning of RNA molecules in vitro. *Nucleic Acids Research.* 21(10):2349-2353 (1993).

Christian et al. Detection of DNA point mutations and mRNA expression levels by rolling circle amplification in individual cells. *Proc Natl Acad Sci USA.* 98(25):14238-14243. Epub Nov. 27, 2001 (Dec. 4, 2001).
Colantuoni et al., Gene expression profiling in postmortem Rett Syndrome brain: differential gene expression and patient classification. *Neurobiol. Dis.* 8(5):847-865 (2001).
Colantuoni et al., High throughout analysis of gene expression in the human brain. *J. Neurosci. Res.* 59(1):1-10 (2000).
Craxton et al. Linear Amplicifcation Sequencing, a Powerful Method for Sequencing DNA. *Meth. Compan. Meth. Enzymol.* 3(1):20-26 (Aug. 1991).
Crooke et al. Pharmacokinetic properties of several novel oligonucleotides analogs in mice. *J Pharmacol Exp Ther.* 277(2):923-937 (1996).
Cummins et al. Biochemical and physicochemical properties of phosphorodithioate DNA. *Biochemistry.* 35(26):8734-8741 (1996).
Daubendiek et al. Generation of catalytic RNAs by rolling transcription of synthetic DNA nanocircles. *Nature Biotechnology.* 15(3):273-277 (1997).
Daubendiek et al. Rolling-circle RNA synthesis: circular oligonucleotides as efficient substrates for T7 RNA polymerase. *J Am Chem Soc.* 117:7818-7819 (1995).
Davanloo et al. Cloning and expression of the gene for bacteriophage T7 RNA polymerase. *Proc Natl Acad Sci USA.* 81:2035-2039 (1984).
de Vroom et al. Syntheses of cyclic oligonucleotides by a modified phosphotriester approach. *Nucleic Acids Research.* 16(10):4607-4620 (1988).
Dean et al. Rapid Amplification of Plasmid and Phage DNA Using Phi29 DNA Polymerase and Multiply-Primed Rolling Circle Amplification. *Genome Res.* 11:1095-1099 (2001).
Diegelman et al. Generation of circular RNAs and trans-cleaving catalytic RNAs by rolling transcription of circular DNA oligoncleotides encoding hairpin ribozymes. *Nucleic Acids Res.* 26(13):3235-3241 (1998).
Doherty et al. Structural and mechanistic conservation in DNA ligases. Survey and Summary. *Nucleic Acids Res.* 28(21):4051-4058 (2000).
Dolinnaya et al. Oligonucleotide circularization by template-directed chemical ligation. *Nucleic Acids Res.* 21(23):5403-5407 (1993).
Dynal Technical Handbook. 2nd. Edition. Biomagnetic Techniques in Molecular Biology. 1. Solid-phase DNA sequencing. 9-34. (Dynal A.S., 1995).
Eckstein et al. Phosphorothioates in molecular biology. *Trends in Bioch Sci.* 14:97-100 (1989).
Erie et al. Melting Behavior of a Covalently Closed, Single-Stranded, Circular DNA. *Biochemistry.* 28:268-273 (1989).
Faruqi et al. High-throughput genotyping of single nucleotide polymorphisms with rolling circle amplification. *BMC Genomics* 2(4) (2001).
Gait. Oligonucleotides. *Antisense Research and Applications.* (Crooke et al, ed., CRC Press) Chapter 16; pp. 289-301 (1993).
Gasparro et al. Site-specific targeting of psoralen photoadducts with a triple helix-forming oligonucleotide: characterization of psoralen monoadduct and crosslink formation. *Nucleic Acids Research.* 22(14):2845-2852 (1994).
Gerdes et al. Dynamic changes in the higher-level chromatin organization of specific sequences revealed by in situ hybridization in nuclear halos. J Cell Biol. 126(2):289-304 (1994).
Gryaznov et al. Template controlled coupling and recombination of oligonucleotide blocks containing thiophosphoryl groups. *Nucleic Acids Res.* 21(6):1403-1408 (1993).
Guatelli et al. Isothermal, in vitro amplification of nucleic acids by a multienzyme reaction molded after retroviral replication. Proc. Natl. Acad. Sci. USA 87:1874-1878 (1990).
Gunji et al. Correlation between the serum level of hepatitis C virus RNA and disease activities in acute and chronic hepatitis C. *Int J Cancer.* 52(5):726-730 (1992).
Guo et al. Enhanced discrimination of single nucleotide polymorphisms by artificial mismatch hybridization. *Nature Biotechnology.* 15:331-335 (1997).
Gupta et al. Expression of HIV-1 RNA in plasma correlates with the development of AIDS: a multicenter AIDS cohort study (MACS).

*Ninth International Conference on AIDS/Fourth STD World Congress.* Jun. 6-11, 1993, Berlin, Germany.

Hacia et al. Detection of heterozygous mutations in BRCA1 using high density oligonucleotide arrays and two-color fluorescence anaylsis. *Nature Genetics*. 14:441-447 (1996).

Haff et al. Single-nucleotide polymorphism identification assays using a thermostable DNA polymerase and delayed extraction MALDI-TOF mass spectrometry. *Genome Res*. 7(4):378-388 (1997).

Hagiwara et al. Quantitation of hepatitis C virus RNA in serum of asymptomatic blood donors and patients with type C chronic liver disease. *Hepatology*. 17(4)545-550 (1993).

Hall et al. Sensitive detection of DNA polymorphisms by the serial invasive signal amplification reaction. *Proc. Natl. Acad. Sci. USA* 97.(15):8272-8277 (Jul. 2000).

Hanvey et al. Antisense and antigene properties of peptide nucleic acids. *Science*. 258:1481-1485 (1992).

Hata et al. Structure of the human ornithine transcarbamylase gene. *J Biochem*. 103:302-308 (1988).

Heinonen et al. Simple triple-label detection of seven cystic fibrosis mutations by time-resolved fluorometry. *Clin Chem*. 43(7):1142-1150 (1997).

Hermanson et al., ed. *Immobilized Affinity Ligands*. (Academic Press, NY, 1992).

Hoeltke et al. Multiple nucleic acid labeling and rainbow detection. *Anal. Biochem*. 207:24-31 (1992).

Holland et al., Detection of Specific Polymerase Chain Reaction Product by Utilizing the 5' →3' Exonuclease Activity of *Thermus aquaticus* DNA Polymerase. *Proc. Natl. Acad. Sci. USA* 88:7276-7280 (Aug. 1991).

Holloway et al. An exonuclease-amplification coupled capture technique improves detection of PCR product. *Nucleic Acids Research*. 21(16):3905-3906 (1993).

Hsuih et al. Quantitative detection of HCV RNA using novel ligation-dependent polymerase chain reaction (LD-PCR). *American Association for the Study of Liver Diseases*. (Chicago, IL, Nov. 3-7, 1995). [poster abstract].

Ishikawa et al. Sequence-based typing of HLA-A2 alleles using a primer with an extra base mismatch. *Hum Immunol*. 42(4):315-318 (1995).

James et al. Surprising fidelity of template-directed chemical ligation of oligonucleotides. *Chemistry & Biology*. 4:595-605 (1997).

Jiang et al. An efficient method for generation and subcloning of tandemly repeated DNA sequences with defined length, orientation and spacing. *Nucl. Acids Res*. 24(16):3278-3279 (1996).

Johnstone et al. Immunochemistry in Practice. (Blackwell Scientific Publications, Oxford, England, 1987) pp. 209-216 and 241-242.

Jonsson et al. Sequence of the DNA ligase-encoding gene from *Thermus scotoductus* and conserved motifs in DNA ligases. *Gene*. 151:177-180 (1995).

Kabanov et al. A new class of antivirals: antisense oligonucleotides combined with a hydrophobic substituent effectively inhibit influenze virus reproduction and synthesis of virus-specific proteins in MDCK cells. *FEBS Lett*. 259(2):327-330 (1990).

Kalin et al. Evaluation of the ligase chain reaction (LCR) for the detection of point mutations. *Mutation Research*. 283(2):119-123 (1992).

Kanaya et al. Template-Directed Polymerization of Oligoadenylates Using Cyanogen Bromide. *Biochemistry*. 25:7423-7430 (1986).

Kaplan et al. Rapid photolytic release of adenosine 5'-triphosphate from a protected analogue: utilization by the Na:K pump of human red blood cell ghosts. *Biochem*. 17:1929-1935 (1978).

Kellogg et al. TaqStart Antibody™: "Hot Start" PCR facilitated by a neutralizing monoclonal antibody directed against Taq DNA polymerase. *BioTechniques*. 16(6):1134-1137 (1994).

Kessler. The digoxigenin: anti-dioxgenin (DIG) technology—a survey on the concept and realization of a novel bioanalytical indictator system. *Mol Cell Probes*. 5:161-205 (1991).

Kimpton et al. Automated DNA profiling employing multiplex amplification of short tandem repeat loci. *PCR Methods and Applications*. 3(1):13-22 (1993).

King et al., Bridging the gap. Joining of nonhomologous ends by DNA polymerases. *Journal of Biological Chemistry*. 269(18):13061-13064 (1994).

Kinoshita et al. Strand Ligation in a double-stranded DNA by T4 RNA Ligase. *Chemistry Letters*. 797-798 (1996).

Kool. Circular oligonucleotides: new concepts in olignucleotide design. *Annual Rev Biomol Struct*. 25:1-28 (1996).

Kricka. Ultrasensitive immunoassay techniques. *Clin Biochem*. 26(5):325-331 (1993).

Kunkel et al. Rapid and efficient site-specific mutagenesis without phenotypic selection. *Methods in Enzymology*. 154:367-382 (1987).

Kwoh et al. Transcription-based amplification system and detection of amplified human immunodeficiency virus type 1 with a bead-based sandwich hybridization format. Proc. Natl. Acad. Sci. USA 86:1173-1177 (1989).

Lamture et al. Direct detection of nucleic acid hybridization on the surface of a charge coupled device. *Nucleic Acids Research*. 22(11):2121-2125 (1994).

Landegren et al. A ligase-mediated gene detection techique. *Science*. 241:1017-1080 (1988).

Landegren. Molecular mechanics of nucleic acid sequence amplification. *Trends Genetics*. 9(6):199-202 (1993).

Lawyer et al. High-level expression, purification, and enzymatic characterization of full-length *Thermus aquaticus* DNA polymerase and a truncated form deficient in 5' and 3' exonuclease activity. *PCR Methods Applications*. 2(4):275-287 (1993).

LeFrere et al. Towards a new predictor of AIDS progression through the quantitation of HIV-1 DNA copies by PCR in HIV-infected individuals. *British Journals of Haematology*. 82(2):467-471 (1992).

Letsinger et al. Cholesteryl-conjugated oligonucleotides: synthesis, properties, and activity as inhibitors of replication of human immunodeficiency virus in cell culture. *Proc Natl Acad Sci USA*. 86:6553-6556 (1989).

Letsinger et al. Synthesis of thymidine olignculeotides by phosphite triester intermediates. *J Am Chem Soc*. 98(12):3655-3661 (Jun. 9, 1976).

Lichter et al. High-resolution mapping of human chromosome 11 by in situ hybridization with cosmid clones. *Science*. 247:64-69 (1990).

Little, Strand Displacement Amplification and Homogeneous Real-Time Detection Incorporated in a Second-Generation DNA Probe System, BDProbeTecET. *Clin. Chem*. 45:777-784 (1999).

Liu et al. Rolling Cycle DNA Synthesis: Small Circular Oligonucleotides as Efficient Templates for DNA Polymerases. *J. Am. Chem. Soc*. 118:1587-1594 (1996).

Lizardi et al. Cascade rolling circle amplification, a homogeneous fluorescence detection system for DNA diagnostics. *Clinical Chemistry* 43(11):2219-2220 (1997).

Lockhart et al. Expression monitoring by hybridization to high-density oligonucleotide arrays. *Nature Biotechnology*. 14:1675-1680. (1996).

Lu et al. High concentration of peripherial blood mononuclear cells harboring infectious virus correlates with rapid progression of human immunodeficiency virus Type1-related diseases. *JID* 168(5):1165-1168 (1993).

Lukyanov et al. Molecule by molecule PCR amplification of complex DNA mixtures for direct sequencing: an approach to in vitro cloning. *Nucleic Acids Research*. 24(11):2194-2195 (1996).

Luo et al. Improving the fidelity of *Thermus thermophilus* DNA ligase. *Nucl Acids Res*. 24(14):3071-3078 (1996).

Lyons et al. Immunosuppressant FK506 promotes neurite outgrowth in cultures of PC12 cells and sensory ganglia. *Proc Natl Acad Sci U S A*. 91(8):3191-3195 (1994).

Manoharan et al. Chemical modifications to improve uptake and bioavailability of antisense oligonucleotides. *Ann NY Acad Sci*. 660:306-309 (1992).

Manoharan et al. Cholic acid-oligonucleotide conjugates for antisense applications. *Bioorg Med Chem Let*. 4(8):1053-1060 (1994).

Manoharan et al. Introduction of a lipophilic thioether tether in the minor groove of nucleic acids for antisense applications. *Biorg Med Chem Let*. 3(12):2765-2770 (1993).

Manoharan et al. Lipidic nucleic acids. *Tetra Lett*. 36(21):3651-3654 (1995).

Manoharan et al. Oligonucleotide conjugates: alteration of the pharmakokinetic properties of antisense agents. *Nucleoside & Nucleotides*. 14:969-973 (1995).

Marshall et al. A biopolymer by an other name would bind as well: a comparison of the ligand-binding pockets of nucleic acids and proteins. *Structure.* 5(6):729-734. (1997).

Marshall et al. Detection of HCV RNA by the asymmetric gap ligase chain reaction. *PCR Methods and Applications.* 4:80-84 (1994).

Maskos et al. Oligonucleotide hybridizations on glass supports: a novel linker for oligonucleotide synthesized in situ. *Nucleic Acids Research.* 20(7):1679-1684 (1992).

McCray et al. A new approach to time-resolved studies of ATP-requiring biological systems: laser flash photolysis of caged ATP. *Proc Natl Acad Sci USA.* 77(12):7237-7241 (1980).

Melton et al. Efficient in vitro synthesis of biologically active RNA and RNA hybridization probes from plasmids containing a bacteriophage SP6 promoter. *Nucleic Acids Research.* 12(18):7035-7056 (1984).

Mendoza et al. High-Throughput Microarray-Based Enzyme-Linked Immunosorbent Assay (ELISA). *BioTechniques.* vol. 27(4):778-788 (1999).

Metzker et al. Termination of DNA synthesis of novel 3'-modified-deoxyribonucleoside 5'-triphosphates. *Nucleic Acids Research.* 22(20):4259-4267 (1994).

Nallur et al., Signal amplification by rolling circle amplification on DNA microarrays. *Nucl. Acids Res.* 29:E118 (2001).

Navarro et al. A general strategy for cloning viroids and other small circular RNAs that uses nminimal amounts of template and does not require prior knowledge of its sequence. *J Virol Meth.* 56:59-66 (1996).

Nazerenko et al. A closed tube format for amplification and detection of DNA based on energy transfer. *Nucl. Acids Res.* 25:2516-2521 (Jun. 1997).

Newton et al. Analysis of any point mutation in DNA. The amplification refractory mutation system (ARMS). *Nucl. Acids Res.* 17(7):2503-2516 (1989).

Nichols et al. A universal nucleosides for use at ambiguous sites in DNA primers. *Nature.* 369(6480):492-493 (1984).

Nielsen et al. Peptide nucleic acids (PNAs): potential anti-sense and anti-gene agents. *Anti-Cancer Drug Design.* 8:53-63 (1993).

Nikiforov et al. Genetic bit analysis: a solid phase method for typing single nucleotide polymorphisms. *Nucleic Acids Research.* 22(20):4167-4175 (1994).

Nikiforov et al. The use of phosphorothioate primers and exonuclease hydrolysis for the preparation of single-stranded PCR products and their detection by solid-phase hybridization. *PCR Methods and Applications.* 3:285-291 (1994).

Nilsson et al. Padlock probes reveal single-nucleotide differences, parent of origin and in situ distribution of centromeric sequences in human chromosomes 13 and 21. *Nature Genet.* 16:252-255 (1997).

Nilsson et al. Padlock probes: circularizing oligonucleotides for localized DNA detection. *Science.* 265:2085-2088 (1994).

Nilsson et al. Real-time monitoring of rolling-circle amplification using a modified molecular beacon design. *Nucleic Acids Res.* 30(14):e66 (2002).

Oberhauser et al. Effective incorporation of 2'-o-methyl-oligoribonculeotides into liposomes and enhanced cell association through modification with thiocholesterol. *Nucl Acids Res.* 20(3):533-538 (1992).

Ørum et al. Single base pair mutation analysis by PNA directed PCR clamping. *Nucleic Acids Research.* 21(23):5332-5336 (1993).

Panasenko et al. A simple, three-step procedure for the large scale purification of DNA ligase from a hybrid λ lysogen construction in vitro. *Journal Biological Chemistry.* 253(13):4590-4592 (1978).

Parker et al. Targeted gene walking polymerase chain reaction. *Nucl Acids Res.* 19:3055-3060 (1991).

Piatak et al. High levels of HIV-1 in plasma during all stages of infection determined by competitive PCR. *Science.* 259:1749-1754 (1993).

Pillai. Photoremovable protecting groups in organic synthesis. *Synthesis.* 1-26 (1980).

Pokrovskaya et al. In vitro transcription: preparative RNA yields in analytical scale reactions. *Analytical Biochemistry.* 220:420-423 (1994).

Porstmann et al. Quantitation of 5-bromo-2-deoxyuridine incorporation into DNA: an enzyme immunoassay for the assessment of the lymphoid cell proliferative response. *J Immunol Meth.* 82:169-179 (1985).

Prakash et al. Molecular Recongition by Circular Olignucletides. Strong Binding of Single-Stranded DNA and RNA. *J Chem Soc, Chem Commun.* 1161-1163 (1991).

Prakash et al. Structural effects in the recognition of DNA by circular oligonucleotides. *J Amer Chem Soc.* 114:3253-3527 (1992).

Prober et al. A system for rapid DNA sequencing with fluorescent chain-terminating dideoxynucleotides. *Science.* 238:336-341 (1987).

*Protein immobilization: fundamentals and applications*, Richard F. Taylor, ed. (M. Dekker, New York, 1991).

Ramsing et al. Helix-coil transition of parallel-stranded DNA. Thermodynamics of hairpin and linear duplex oligonucleotides. *Biochem.* 28:9528-9535 (1989).

Reese et al. The *H*-phosphonate approach to the solution phase synthesis of linear and cyclic oligoribonucleotides. *Nucleic Acids Research.* 27(4):963-971 (1999).

Richards et al. Conditional mutator phenotypes in hMSH2-deficient tumor cell lines. *Science.* 277-1523-1526 (1997).

Ried et al. Simultaneous visualization of seven different DNA probes by in situ hybridization using combinational fluoroscence and digital imaging microscopy. *Proc Natl Acad Sci USA.* 89(4):1388-1392 (1982).

Rossi et al. Functional characterization of the T4DNA ligase: a new insight into the mechanism of action. *Nucleic Acids Res.* 25(11):2106-2113 (1997).

Rubin et al. Convergent DNA synthesis: a non-enzymatic diverization approach to circular oligodeoxynucleotides. *Nucleic Acids Res.* 23(17):3547-3553 (1995).

Rys et al. Preventing false positives: quantitative evaluation of three protocols for inactivation of polymerase chain reaction amplification products. *Journal of Clinical Microbiology.* 31(9):2356-2360 (1993).

Saiki et al. Enzymatic Amplification of β-Globin Genomic Sequences and Restriction Site Analysis for Diagnosis of Sickle Cell Anemia. *Science.* 230:1350-1354 (1985).

Saiki et al. Primer-Directed Enzymatic Amplification of DNA with a Thermostable DNA Polymerase. *Science* 239:487-491 (Jan. 29, 1988).

Saison-Behmoaras et al. Short modified antisense oligonucleotides directed against Ha-*ras* point mutation induce selective cleavage of the mRNA and inhibit T24 cells proliferation. *EMBO J.* 10(5):1111-1118 (1991).

Saksela et al. Human immunodeficiency virus type 1 mRNA expression in peripheral blood cells predicts disease progression independently of the numbers of CD4+ lymphocytes. *Proc Natl Acad Sci USA.* 91(3):1104-1108 (1994).

Saris et al. Blotting of RNA onto ion exchange paper allowing subsequent characterization by in situ translation in addition to blot hybridization. *Nucleic Acids Res.* 10(16):4831-4843 (1982).

Schena et al. DNA Microarrays: A Practical Approach. (Oxford University Press, New York, 1999) 1-16.

Schena et al. Parallel human genome analysis: microarray-based expression monitoring of 1000 genes. *Proc Natl Acad Sci USA.* 93:10614-10619 (1994).

Schena et al. Quantitative monitoring of gene expression patterns with a complementary DNA microarray. *Science.* 270:467-470 (1995).

Schenborn et al. A novel transcription property of SP6 and T7 RNA polymerases: dependence on template structure. *Nucleic Acids Research.* 13(17):6223-6236 (1985).

Schenk et al. The accessibility of thiophosphorylated groups in DNA fragments to the enzymatic activity of ligases and restriction endonclease Bbs 1. *Biochem Mol Biol Int.* 36(5):1037-1043 (1995) Abstract.

Schwartz et al. Improved yields of long PCR products using gene 32 protein. *Nucl Acids Res.* 18(4):1079 (1990).

Schweitzer and Kingsmore. Combining nucleic acid amplification and detection. *Curr. Opin. Biotech.* 12(1):21-27 (Feb. 2001).

Shea et al. Synthesis, hybridization properties and antiviral activity of lipid-oligodeoxynucleotide conjugates. *Nucl Acids Res.* 18(13):3777-3783 (1990).

Shumaker et al. Mutation detection by solid phase primer extension. *Human Mutation.* 7(4):346-354 (1996).

Silzel et al. Mass-sensing, Multianalyte Microarray Immunoassay with Imaging Detection. Clin. Chem. 44: 2036-2043 (1998).

Simpson. The natural somatic mutation frequency and human carcinogenesis. *Adv Cancer Res.* 71:209-240 (1997).

Skerra. Phosphorothioate primers improve the amplification of DNA sequences by DNA polymerases with proofreading activity. *Nucleic Acids Res.* 20(14):3551-3554 (1992).

Stratagene Catalog, p. 39 (1988).

Stratagene Catalog, p. 76 (1992).

Strauss et al. Quantitative measurement of calretinin and β-actin mRNA in rat brain micropunches without prior isolation of RNA. *Mol Brain Res.* 20:229-239 (1993).

Strong et al. Marked improvement of PAC and BAC cloning is achieved using electroelution of pulsed-field gel-separated partial digests of genomic DNA. *Nucleic Acids Res.* 25(19):3959-3961 (1997).

Studier et al. Use of T7 RNA polymerase to direct expression of cloned genes. *Methods in Enzymology.* 185:60-89 (1990).

Stump et al., The use of modified primers to eliminate cycle sequencing artifacts. *Nucl. Acids Res.* 27:4642-4648 (1999).

Svinarchuk et al. Inhibition of HIV proliferation in MT-4 cells by antisense oligonucleotide conjugated to lipophilic groups. *Biochimie.* 75:49-54 (1993).

Syvanen et al. Fast quantification of nucleic acid hybrids by affinity-based hybrid collection. *Nucleic Acids Research.* 14(12):5037-5048 (1986).

Tabor et al. Selective inactivation of the exonuclease activity of bacteriohage T7 DNA polymerase by in Vitro Mutagenesis. *J Biol Chem.* 264(11):6447-6458 (1989).

Tabor et al. Selective oxidation of the exonuclease domain of bacteriophage T7 DNA polymerase. *J Biol Chem.* 262:15330-15333 (1987).

Thelwell et al. Mode of action and application of Scorpion primers to mutation detection. *Nucl. Acids Res.* 28(19):3752-3761 (2000).

Thomas et al. Cascade rolling circle amplification, a homogenous fluorescence detection system for DNA diagnostics. *Clin Chem.* 43:2119, Abs. 38 (1997).

Thorbjarnardottir et al. Cloning and sequence analysis of the DNA lligase-encoding gene of *Rhodothermus marinus*, and overproduction, purification and characterization of two thermophilic DNA ligases. *Gene* 161:1-6 (1995).

Tyagi et al. Extremely sensitive, background-free gene detection using binary probes and Qβ replicase. Proc. Natl Acda. Sci. USA 93:5395-5400 (1996).

Uemori et al. Cloning fo the DNA polymerase gene of *Bacillus caldotenax* and characterization of the gene product. *J. Biochem.* 113(3):401-410 (Mar. 1993).

Unrau et al. Non-cloning amplification of specific DNA fragments from whole genomic DNA digests using DNA 'indexers'. *Gene.* .145(2):163-169 (1994).

Velculescu et al. Serial analysis of gene expression. *Science.* 270:484-487 (1995).

Vogelstein et al. Supercoiled loops and eucaryotic DNA replication. *Cell.* 22:79-85 (1980).

Voisey et al. Interrogation of multimeric DNA amplification products by competitive primer extension using bst DNA polymerase (large fragment). *Biotechniques.* 31(5):1122-1129 (2001).

Walker et al. Isothermal in vitro amplification of DNA by a restriction enzyme/DNA polymerase system. *Proc Natl Acad Sci USA.* 89:392-396 (1992).

Walker et al. Strand displacement amplification—an isothermal, in vitro DNA amplification technique. *Nucleic Acids Research.* 20(7):1691-1696 (1992).

Walter et al. Strand displacement amplification as an in vitro model for rolling-circle replication: deletion formation and evolution during serial transfer. *Proc Natl Acad Sci USA.* 91:7937-7941 (1994).

Wang et al. Circular RNA oligonucleotides. Synthesis, nucleic acid binding properties, and a comparison with circular DNAs. Nucl. Acids Res. 22(12):2326-2333 (1994).

Welford et al. Detection of differentially expressed genes in primary tumor tissues using representational differences analysis coupled to microarray hybridization. *Nucleic Acids Res.* 26(12):3059-3065 (1998).

Wemmer et al. Preparation and melting of single strand circular DNA loops. *Nucleic Acids Res.* 13(23):8611-8621 (1985).

White et al. Concatemer chain reaction: a Taq DNA polymerase-mediated mechanism for generating long tandemly repetitive DNA sequences. *Anal Biochem.* 199(2):184-190 (1991).

Wiedmann et al. Ligase chain reaction (LCR)—overview and applications. *PCR Methods and Applications.* (Cold Spring Harbor Laboratory Press, Cold Spring Harbor, NY, 1994) [pp. S51-S64].

Wilson et al. Enzyme complex amplification-a signal amplification method for use in enzyme immunoassays. *Anal Biochem.* 209(1):183-187 (1993).

Winn-Deen et al. Non-radioactive detection of *Mycobacterium tuberculosis* LCR products in a microtitre plate format. *Molecular and Cellular Probes.* (England) 7(3):179-186 (1993).

Xu et al. Nonenzymatic autoligation in direct three-color detection of RNA and DNA point mutations. *Nature Biotechnology.* 19:148-152 (2001).

Yang et al. Combining SSH and cDNA microarrays for rapid identification of differentially expressed genes. *Nucleic Acids Res.* 27(6):1517-1523 (1999).

Young et al. Quantitative analysis of solution hybridization. *Nucleic Acid Hybridisation: A Practical Approach.* (IRL Press, 1985) pp. 47-71.

Zehavi et al. Light sensitive glycosides. II. 2-Nitrobenzyl 6-Deoxy-α-L-mannopyranoside and 2-Nitrobenzyl 6-Deoxy-β-L-galactophyranoside. *J Organic Chem.* 37(14):2285-2285 (1972).

Zehavi et al. Light-Sensitive Glycosides. I. 6-nitroveratryl β-D-glucopyranoside and 2-nitrobenzyl β-D-glucopyranoside. *J Organic Chem.* 37(14):2281-2285 (1972).

Zhang et al. Amplification of target-specific, ligation-dependent circular probe. *Gene* 211:277-285 (1990).

Zhang et al. Whole genome amplification from a single cell: Implications for genetic analysis. *Proc. Natl. Acad. Sci. USA* 89:5847-5851 (Jul. 1992).

Zhu et al. Global Analysis of Protein Activities Using Proteome Chips. *Science* 293(5537):2101-2105 (2001).

Aliotta et al. Thermostable *Bst* DNA polymerase I lacks a 3'→ =' proofreading exonuclease activity. *Genet. Anal* (Netherlands) 12:185-195 (1996).

Anderson and Seilhamer. A comparison of selected mRNA and protein abundances in human liver. *Electrophoresis* 18:533-537, (1997).

Beaucage et al. Deoxynucleoside Phosphoramidites-A New Class of Key Intermediates For Deoxypolycleotide Synthesis. *Tetrahedron Lett.* 22:1850 (1981).

Chatterjee et al. Cloning and overexpression of the gene encoding bacteriophage T5 DNA polymerase. *Gene* 97:13-19 (1991).

Abravaya et al. Detection of point mutations with a modified ligase chain reaction (Gap-LCR). *Nucleic Acids Res.* 23(4):675-682 (1995).

U.S. Appl. No. 09/803,713, Alsmadi et al., filed Mar. 9, 2001, Issue Notification, May 14, 2003.

U.S. Appl. No. 09/803,713, Alsmadi et al., filed Mar. 9, 2001, Notice of Allowance, Feb. 4, 2003.

U.S. Appl. No. 09/803,713, Alsmadi et al., filed Mar. 9, 2001, Supplemental Response, Jan. 23, 2003.

U.S. Appl. No. 09/803,713, Alsmadi et al., filed Mar. 9, 2001, Response after Non-Final Action, Nov. 5, 2002.

U.S. Appl. No. 09/803,713, Alsmadi et al., filed Mar. 9, 2001, Non-Final Rejection, Jun. 5, 2002.

U.S. Appl. No. 09/803,713, Alsmadi et al., filed Mar. 9, 2001, Response to Election / Restriction Filed, Mar. 29, 2002.

U.S. Appl. No. 09/803,713, Alsmadi et al., filed Mar. 9, 2001, Restriction Requirement, Feb. 21, 2002.

U.S. Appl. No. 10/325,490, Alsmadi et al., filed Dec. 19, 2002, Abandonment for Failure to Respond to Office Action, Mar. 8, 2007.

U.S. Appl. No. 10/325,490, Alsmadi et al., filed Dec. 19, 2002, Non-Final Rejection, Aug. 9, 2006.

U.S. Appl. No. 10/325,490, Alsmadi et al., filed Dec. 19, 2002, Response after Non-Final Action, May 25, 2006.
U.S. Appl. No. 10/325,490, Alsmadi et al., filed Dec. 19, 2002, Non-Final Rejection, Jan. 24, 2006.
U.S. Appl. No. 10/325,490, Alsmadi et al., filed Dec. 19, 2002, Response to Election / Restriction Filed, Oct. 21, 2005.
U.S. Appl. No. 10/325,490, Alsmadi et al., filed Dec. 19, 2002, Restriction Requirement, Sep. 16, 2005.
U.S. Appl. No. 10/404,944, Alsmadi et al., filed Mar. 31, 2003, Abandonment for Failure to Respond to Office Action, Nov. 27, 2006.
U.S. Appl. No. 10/404,944, Alsmadi et al., filed Mar. 31, 2003, Non-Final Rejection, May 9, 2006.
U.S. Appl. No. 10/404,944, Alsmadi et al., filed Mar. 31, 2003, Response after Non-Final Action, Mar. 6, 2006.
U.S. Appl. No. 10/404,944, Alsmadi et al., filed Mar. 31, 2003, Non-Final Rejection, Dec. 5, 2005.
U.S. Appl. No. 09/547,757, Faruqi, filed Apr. 12, 2000, Issue Notification, Mar. 21, 2002.
U.S. Appl. No. 09/547,757, Faruqi, filed Apr. 12, 2000, Notice of Allowance, Aug. 31, 2001.
U.S. Appl. No. 09/597,836, Kingsmore et al., filed Jun. 20, 2000, Issue Notification, Feb. 20, 2003.
U.S. Appl. No. 09/597,836, Kingsmore et al., filed Jun. 20, 2000, Notice of Allowance, Nov. 17, 2002.
U.S. Appl. No. 09/597,836, Kingsmore et al., filed Jun. 20, 2000, RCE with Response to Office Action, Sep. 18, 2002.
U.S. Appl. No. 09/597,836, Kingsmore et al., filed Jun. 20, 2000, Final Rejection, Mar. 19, 2002.
U.S. Appl. No. 09/597,836, Kingsmore et al., filed Jun. 20, 2000, Response after Non-Final Action, Feb. 6, 2002.
U.S. Appl. No. 09/597,836, Kingsmore et al., filed Jun. 20, 2000, Non-Final Rejection, Nov. 5, 2001.
U.S. Appl. No. 09/597,836, Kingsmore et al., filed Jun. 20, 2000, Response after Non-Final Action, Sep. 20, 2001.
U.S. Appl. No. 09/597,836, Kingsmore et al., filed Jun. 20, 2000, Non-Final Rejection, Mar. 20, 2001.
U.S. Appl. No. 09/597,836, Kingsmore et al., filed Jun. 20, 2000, Preliminary Amendment, Oct. 26, 2000.
U.S. Appl. No. 10/341,287, Kingsmore et al., filed Jan. 13, 2003, Post Issue Communication - Certificate of Correction, Sep. 7, 2005.
U.S. Appl. No. 10/341,287, Kingsmore et al., filed Jan. 13, 2003, Request for Certificate of Correction, Aug. 25, 2005.
U.S. Appl. No. 10/341,287, Kingsmore et al., filed Jan. 13, 2003, Issue Notification, Jul. 6, 2005.
U.S. Appl. No. 10/341,287, Kingsmore et al., filed Jan. 13, 2003, Notice of Allowance, Mar. 15, 2005.
U.S. Appl. No. 10/341,287, Kingsmore et al., filed Jan. 13, 2003, Response after Non-Final Action, Jan. 4, 2005.
U.S. Appl. No. 10/341,287, Kingsmore et al., filed Jan. 13, 2003, Terminal Disclaimer Filed, Jan. 4, 2005.
U.S. Appl. No. 10/341,287, Kingsmore et al., filed Jan. 13, 2003, Non-Final Rejection, Oct. 22, 2004.
U.S. Appl. No. 11/187,537, Kingsmore et al., filed Jul. 22, 2005, Miscellaneous Communication to Applicant Notice of Defective Declaration, Oct. 4, 2007.
U.S. Appl. No. 11/187,537, Kingsmore et al., filed Jul. 22, 2005, Petition Decision - Granted, Mar. 2, 2006.
U.S. Appl. No. 11/187,537, Kingsmore et al., filed Jul. 22, 2005, Petition Entered, Dec. 23, 2005.
U.S. Appl. No. 09/897,259, Ward et al., filed Jul. 2, 2001, Issue Notification, Jan. 15, 2004.
U.S. Appl. No. 09/897,259, Ward et al., filed Jul. 2, 2001, Examiner's Amendment, Dec. 8, 2003.
U.S. Appl. No. 09/897,259, Ward et al., filed Jul. 2, 2001, Notice of Allowance, Jul. 1, 2003.
U.S. Appl. No. 09/897,259, Ward et al., filed Jul. 2, 2001, Response after Non-Final Action, Apr. 18, 2003.
U.S. Appl. No. 09/897,259, Ward et al., filed Jul. 2, 2001, Non-Final Rejection, Jan. 17, 2003.
U.S. Appl. No. 09/897,259, Ward et al., filed Jul. 2, 2001, Response to Election / Restriction Filed, Nov. 4, 2002.
U.S. Appl. No. 09/897,259, Ward et al., filed Jul. 2, 2001, Restriction Requirement, Sep. 30, 2002.
U.S. Appl. No. 09/910,383, Nailur et al., filed Jul. 20, 2001, Abandonment for Failure to Respond to Office Action, Nov. 14, 2007.
U.S. Appl. No. 09/910,383, Nailur et al., filed Jul. 20, 2001, Advisory Action, May 1, 2007.
U.S. Appl. No. 09/910,383, Nallur et al., filed Jul. 20, 2001, Amendment/Argument after Notice of Appeal, Apr. 18, 2007.
U.S. Appl. No. 09/910,383, Nallur et al., filed Jul. 20, 2001, Notice of Appeal Filed, Apr. 18, 2007.
U.S. Appl. No. 09/910,383, Nallur et al., filed Jul. 20, 2001, Examiner Interview Summary, Apr. 9, 2007.
U.S. Appl. No. 09/910,383, Nallur et al., filed Jul. 20, 2001, Final Rejection, Dec. 13, 2006.
U.S. Appl. No. 09/910,383, Nallur et al., filed Jul. 20, 2001, Response after Non-Final Action, Oct. 2, 2006.
U.S. Appl. No. 09/910,383, Nallur et al., filed Jul. 20, 2001, Non-Final Rejection, Jun. 15, 2006.
U.S. Appl. No. 09/910,383, Nallur et al., filed Jul. 20, 2001, Withdrawal of Informal Amendment Notice, Apr. 7, 2006.
U.S. Appl. No. 09/910,383, Nallur et al., filed Jul. 20, 2001, Response after Non-Final Action, Mar. 22, 2006.
U.S. Appl. No. 09/910,383, Nallur et al., filed Jul. 20, 2001, Notice of Informal or Non-Responsive RCE Amendment, Mar. 27, 2006.
U.S. Appl. No. 09/910,383, Nallur et al., filed Jul. 20, 2001, Advisory Action, Dec. 13, 2005.
U.S. Appl. No. 09/910,383, Nallur et al., filed Jul. 20, 2001, Amendment after Final Rejection, Nov. 23, 2005.
U.S. Appl. No. 09/910,383, Nallur et al., filed Jul. 20, 2001, Examiner Interview Summary Record, Oct. 12, 2005.
U.S. Appl. No. 09/910,383, Nallur et al., filed Jul. 20, 2001, Advisory Action, Sep. 14, 2005.
U.S. Appl. No. 09/910,383, Nallur et al., filed Jul. 20, 2001, Amendment after Final Rejection, Aug. 26, 2005.
U.S. Appl. No. 09/910,383, Nallur et al., filed Jul. 20, 2001, Final Rejection, May 23, 2005.
U.S. Appl. No. 09/910,383, Nallur et al., filed Jul. 20, 2001, Response after Non-Final Action, Mar. 14, 2005.
U.S. Appl. No. 09/910,383, Nallur et al., filed Jul. 20, 2001, Non-Final Rejection, Jan. 27, 2005.
U.S. Appl. No. 09/910,383, Nallur et al., filed Jul. 20, 2001, Response after Non-Final Action, Nov. 22, 2004.
U.S. Appl. No. 09/910,383, Nallur et al., filed Jul. 20, 2001, Non-Final Rejection, Jun. 23, 2004.
U.S. Appl. No. 09/977,868, Dean et al., filed Oct. 15, 2001, Issue Notification, Nov. 30, 2005.
U.S. Appl. No. 09/977,868, Dean et al., filed Oct. 15, 2001,Notice of Allowance, Feb. 22, 2005.
U.S. Appl. No. 09/977,868, Dean et al., filed Oct. 15, 2001, Examiner's Amendment, Feb. 22, 2005.
U.S. Appl. No. 09/977,868, Dean et al., filed Oct. 15, 2001, Response after Non-Final Action, Jan. 4, 2005.
U.S. Appl. No. 09/977,868, Dean et al., filed Oct. 15, 2001, Non-Final Rejection, Sep. 9, 2004.
U.S. Appl. No. 09/977,868, Dean et al., filed Oct. 15, 2001, Preliminary Amendment, Apr. 11, 2002.
U.S. Appl. No. 09/982,212, Dean et al., filed Oct. 18, 2001, Issue Notification, Aug. 21, 2003.
U.S. Appl. No. 09/982,212, Dean et al., filed Oct. 18, 2001, Notice of Allowance, May 20, 2003.
U.S. Appl. No. 09/982,212, Dean et al., filed Oct. 18, 2001, Response after Non-Final Action, May 7, 2003.
U.S. Appl. No. 09/982,212, Dean et al., filed Oct. 18, 2001, Non-Final Rejection, Apr. 18, 2003.
U.S. Appl. No. 09/982,212, Dean et al., filed Oct. 18, 2001, Preliminary Amendment, Jan. 24, 2002.
U.S. Appl. No. 09/982,212, Dean et al., filed Oct. 18, 2001, Preliminary Amendment, Oct. 8, 2001.
U.S. Appl. No. 10/272,465, Dean et al., filed Oct. 15, 2002, Decision on Petition to Revive, May 22, 2006.
U.S. Appl. No. 10/275,465, Dean et al., filed Oct. 15, 2002, Petition to Revive Application, Mar. 16, 2006.
U.S. Appl. No. 10/272,465, Dean et al., filed Oct. 15, 2002, Issue Notification, Jun. 21, 2006.

U.S. Appl. No. 10/272,465, Dean et al., filed Oct. 15, 2002, Notice of Allowance, Dec. 13, 2005.
U.S. Appl. No. 10/272,465, Dean et al., filed Oct. 15, 2002, Examiner's Amendment, Dec. 13, 2005.
U.S. Appl. No. 10/272,465, Dean et al., filed Oct. 15, 2002, Terminal Disclaimer Filed, Sep. 6, 2005.
U.S. Appl. No. 10/272,465, Dean et al., filed Oct. 15, 2002, Response after Non-Final Action, Sep. 6, 2005.
U.S. Appl. No. 10/272,465, Dean et al., filed Oct. 15, 2002, Non-Final Rejection, Aug. 5, 2005.
U.S. Appl. No. 10/429,229, Bomarth et al., filed May 2, 2003, Issue Notification, Oct. 31, 2007.
U.S. Appl. No. 10/429,229, Bomarth et al., filed May 2, 2003, Issue Fee Payment Received, Sep. 17, 2007.
U.S. Appl. No. 10/429,229, Bomarth et al., filed May 2, 2003, Supplemental Notice of Allowance, Jul. 31, 2007.
U.S. Appl. No. 10/429,229, Bomarth et al., filed May 2, 2003, Notice of Allowance, Jun. 18, 2007.
U.S. Appl. No. 10/429,229, Bomarth et al., filed May 2, 2003, Examiner Interview Summary, Jun. 18, 2007.
U.S. Appl. No. 10/429,229, Bomarth et al., filed May 2, 2003, Examiner's Amendment, Jun. 18, 2007.
U.S. Appl. No. 10/429,229, Bomarth et al., filed May 2, 2003, Amendment after Final Rejection, Jun. 5, 2007.
U.S. Appl. No. 10/429,229, Bomarth et al., filed May 2, 2003, Final Rejection, Feb. 28, 2007.
U.S. Appl. No. 10/429,229, Bomarth et al., filed May 2, 2003, Response after Non-Final Action & Terminal Disclaimer, Dec. 18, 2006.
U.S. Appl. No. 10/429,229, Bomarth et al., filed May 2, 2003, Non-Final Rejection, Jun. 20, 2006.
U.S. Appl. No. 10/429,229, Bomarth et al., filed May 2, 2003, Response to Election / Restriction Filed, Apr. 21, 2006.
U.S. Appl. No. 10/429,229, Bomarth et al., filed May 2, 2003, Restriction Requirement, Feb. 16, 2006.
U.S. Appl. No. 11/871,707, Bomarth et al., filed Oct. 12, 2007, Notice of Publication, Jun. 5, 2008.
U.S. Appl. No. 11/871,707, Bornarth et al., filed Oct. 12, 2007, Preliminary Amendment, Jan. 31, 2008.
U.S. Appl. No. 08/754,681, Lizardi et al., filed Nov. 21, 1996, Issue Notification, Oct. 20, 2000.
U.S. Appl. No. 08/754,681, Lizardi et al., filed Nov. 21, 1996, Issue Fee Payment Verified, Jun. 23, 2000.
U.S. Appl. No. 08/754,681, Lizardi et al., filed Nov. 21, 1996, Notice of Allowance, Mar. 28, 2000.
U.S. Appl. No. 08/754,681, Lizardi et al., filed Nov. 21, 1996, Notice of Appeal Filed, Feb. 7, 2000.
U.S. Appl. No. 08/754,681, Lizardi et al., filed Nov. 21, 1996, Amendment after Final Rejection & Terminal Disclaimer Filed, Dec. 30, 1999.
U.S. Appl. No. 08/754,681, Lizardi et al., filed Nov. 21, 1996, Final Rejection, Aug. 4, 1999.
U.S. Appl. No. 08/754,681, Lizardi et al., filed Nov. 21, 1996, Supplemental Response, Apr. 16, 1999.
U.S. Appl. No. 08/754,681, Lizardi et al., filed Nov. 21, 1996, Response after Non-Final Action, Apr. 6, 1999.
U.S. Appl. No. 08/754,681, Lizardi et al., filed Nov. 21, 1996, Non-Final Rejection, Oct. 1, 1998.
U.S. Appl. No. 08/754,681, Lizardi et al., filed Nov. 21, 1996, Response after Non-Final Action, Jul. 9, 1998.
U.S. Appl. No. 08/754,681, Lizardi et al., filed Nov. 21, 1996, Non-Final Rejection, Jan. 6, 1998.
U.S. Appl. No. 08/754,681, filed Nov. 21, 1996, Response after Non-Final Action, Oct. 24, 1997.
U.S. Appl. No. 09/602,428, Lizardi et al., filed Jun. 23, 2000, Issue Notification, Nov. 21, 2001.
U.S. Appl. No. 09/602,428, Lizardi et al., filed Jun. 23, 2000, Notice of Allowance, Jun. 28, 2001.
U.S. Appl. No. 09/602,428, Lizardi et al., filed Jun. 23, 2000, Terminal Disclaimer Filed, Apr. 12, 2001.
U.S. Appl. No. 09/602,428, Lizardi et al., filed Jun. 23, 2000, Response after Non-Final Action, Apr. 12, 2001.
U.S. Appl. No. 09/602,428, Lizardi et al., filed Jun. 23, 2000, Non-Final Rejection, Nov. 22, 2000.
U.S. Appl. No. 09/602,428, Lizardi et al., filed Jun. 23, 2000, Preliminary Amendment, Jun. 23, 2000.
U.S. Appl. No. 09/841,513, Lizardi, filed Apr. 24, 2001, Issue Notification, Sep. 25, 2003.
U.S. Appl. No. 09/841,513, Lizardi, filed Apr. 24, 2001, Terminal Disclaimer Filed, May 7, 2003.
U.S. Appl. No. 09/841,513, Lizardi, filed Apr. 24, 2001, Notice of Allowance, Jan. 16, 2003.
U.S. Appl. No. 09/841,513, Lizardi, filed Apr. 24, 2001, Terminal Disclaimer Filed, Oct. 24, 2002.
U.S. Appl. No. 09/841,513, Lizardi, filed Apr. 24, 2001, Response after Non-Final Action, Oct. 24, 2002.
U.S. Appl. No. 09/841,513, Lizardi, filed Apr. 24, 2001, Non-Final Rejection, Apr. 30, 2002.
U.S. Appl. No. 09/841,513, Lizardi, filed Apr. 24, 2001, Preliminary Amendment, Apr. 24, 2001.
U.S. Appl. No. 10/413,041, Lizardi et al., filed Apr. 10, 2003, Abandonment for Failure to Respond to Office Action, Apr. 5, 2006.
U.S. Appl. No. 10/413,041, Lizardi et al., filed Apr. 10, 2003, Restriction Requirement, Sep. 22, 2005.
U.S. Appl. No. 09/460,078, Hafner et al., filed Dec. 14, 1999, Issue Notification, Nov. 25, 2004.
U.S. Appl. No. 09/460,078, Hafner et al., filed Dec. 14, 1999, Notice of Allowance, Jul. 14, 2004.
U.S. Appl. No. 09/460,078, Hafner et al., filed Dec. 14, 1999, Amendment after Final Rejection, Jun. 17, 2004.
U.S. Appl. No. 09/460,078, Hafner et al., filed Dec. 14, 1999, Examiner Interview Summary, May 25, 2004.
U.S. Appl. No. 09/460,078, Hafner et al., filed Dec. 14, 1999, Final Rejection, Feb. 13, 2004.
U.S. Appl. No. 09/460,078, Hafner et al., filed Dec. 14, 1999, Response after Non-Final Action, Nov. 24, 2003.
U.S. Appl. No. 09/460,078, Hafner et al., filed Dec. 14, 1999, Non-Final Rejection, May 19, 2003.
U.S. Appl. No. 09/460,078, Hafner et al., filed Dec. 14, 1999, Response after Non-Final Action, Jan. 14, 2003.
U.S. Appl. No. 09/460,078, Hafner et al., filed Dec. 14, 1999, Non-Final Rejection, Sep. 4, 2002.
U.S. Appl. No. 09/460,078, Hafner et al., filed Dec. 14, 1999, Request for Continued Examination (RCE), Jun. 17, 2002.
U.S. Appl. No. 09/460,078, Hafner et al., filed Dec. 14, 1999, Notice of Appeal Filed, Jan. 25, 2002.
U.S. Appl. No. 09/460,078, Hafner et al., filed Dec. 14, 1999, Final Rejection, Jul. 17, 2001.
U.S. Appl. No. 09/460,078, Hafner et al., filed Dec. 14, 1999, Response after Non-Final Action, May 23, 2001.
U.S. Appl. No. 09/460,078, Hafner et al., filed Dec. 14, 1999, Non-Final Rejection, Nov. 20, 2000.
U.S. Appl. No. 09/460,078, Hafner et al., filed Dec. 14, 1999, Response to Election / Restriction Filed, Oct. 3, 2000.
U.S. Appl. No. 09/460,078, Hafner et al., filed Dec. 14, 1999, Notice of Restarted Response Period, Jun. 30, 2000.
U.S. Appl. No. 09/460,078, Hafner et al., filed Dec. 14, 1999, Restriction Requirement, May 23, 2000.
U.S. Appl. No. 10/917,580, Hafner et al., filed Aug. 13, 2004, Issue Notification, Mar. 26, 2008.
U.S. Appl. No. 10/917,580, Hafner et al., filed Aug. 13, 2004, Notice of Allowance, Nov. 30, 2007.
U.S. Appl. No. 10/917,580, Hafner et al., filed Aug. 13, 2004, Examiner's Amendment Communication, Nov. 30, 2007.
U.S. Appl. No. 10/917,580, Hafner et al., filed Aug. 13, 2004, Terminal Disclaimer Filed, Oct. 1, 2007.
U.S. Appl. No. 10/917,580, Hafner et al., filed Aug. 13, 2004, Response after Non-Final Action, Oct. 1, 2007.
U.S. Appl. No. 10/917,580, Hafner et al., filed Aug. 13, 2004, Non-Final Rejection, Jun. 25, 2007.
U.S. Appl. No. 10/917,580, Hafner et al., filed Aug. 13, 2004, Response to Election / Restriction Filed, May 10, 2007.
U.S. Appl. No. 10/917,580, Hafner et al., filed Aug. 13, 2004, Restriction Requirement, Jan. 11, 2007.

U.S. Appl. No. 10/917,580, Hafner et al., filed Aug. 13, 2004, Preliminary Amendment, Nov. 19, 2004.
U.S. Appl. No. 10/325,665, Alsmadi et al., filed Dec. 19, 2002, Non-Final Rejection, Apr. 17, 2008.
U.S. Appl. No. 10/325,665, Alsmadi et al., filed Dec. 19, 2002, Examiner Interview Summary, Apr. 17, 2008.
U.S. Appl. No. 10/325,665, Alsmadi et al., filed Dec. 19, 2002, Non-Final Rejection, Oct. 25, 2007.
U.S. Appl. No. 10/325,665, Alsmadi et al., filed Dec. 19, 2002, Amendment / Argument after Notice of Appeal, Sep. 25, 2007.
U.S. Appl. No. 10/325,665, Alsmadi et al., filed Dec. 19, 2002, Final Rejection, Mar. 26, 2007.
U.S. Appl. No. 10/325,665, Alsmadi et al., filed Dec. 19, 2002, Response after Non-Final Action, Dec. 22, 2006.
U.S. Appl. No. 10/325,665, Alsmadi et al., filed Dec. 19, 2002, Non-Final Rejection, Aug. 3, 2006.
U.S. Appl. No. 10/325,665, Alsmadi et al., filed Dec. 19, 2002, Response after Non-Final Action & Terminal Disclaimer, Apr. 18, 2006.
U.S. Appl. No. 10/325,665, Alsmadi et al., filed Dec. 19, 2002, Non-Final Rejection, Dec. 30, 2005.
U.S. Appl. No. 10/325,665, Alsmadi et al., filed Dec. 19, 2002, Response to Electron / Restriction Filed, Sep. 21, 2005.
U.S. Appl. No. 10/325,665, Alsmadi et al., filed Dec. 19, 2002, Restriction Requirement, Apr. 21, 2005.
U.S. Appl. No. 10/335,573, Kumar et al., filed Dec. 31, 2002, Issue Notification, Nov. 30, 2005.
U.S. Appl. No. 10/335,573, Kumar et al., filed Dec. 31, 2002, Notice of Allowance, Mar. 29, 2005.
U.S. Appl. No. 10/335,573, Kumar et al., filed Dec. 31, 2002, Response after Non-Final Action, Dec. 1, 2004.
U.S. Appl. No. 10/335,573, Kumar et al., filed Dec. 31, 2002, Non-Final Rejection, Jul. 29, 2004.
U.S. Appl. No. 11/201,339, Kumar et al., filed Aug. 10, 2005, Restriction Requirement, Sep. 25, 2007.
U.S. Appl. No. 10/327,602, Lasken, filed Dec. 20, 2002, Final Rejection, Aug. 12, 2008.
U.S. Appl. No. 10/327,602, Lasken, filed Dec. 20, 2002, Response after Final Rejection, May 15, 2008.
U.S. Appl. No. 10/327,602, Lasken, filed Dec. 20, 2002, Non-Final Rejection, Jan. 17, 2008.
U.S. Appl. No. 10/327,602, Lasken, filed Dec. 20, 2002, Request for Continued Examination, Oct. 25, 2007.
U.S. Appl. No. 10/327,602, Lasken, filed Dec. 20, 2002, Examiner Interview Summary, Oct. 16, 2007.
U.S. Appl. No. 10/327,602, Lasken, filed Dec. 20, 2002, Amendment after Final, Oct. 1, 2007.
U.S. Appl. No. 10/327,602, Lasken, filed Dec. 20, 2002, Final Rejection, May 23, 2007.
U.S. Appl. No. 10/327,602, Lasken, filed Dec. 20, 2002, Response after Non-Final Rejection, Mar. 15, 2007.
U.S. Appl. No. 10/327,602, Lasken, filed Dec. 20, 2002, Non-Final Rejection, Nov. 14, 2006.
U.S. Appl. No. 10/327,602, Lasken, filed Dec. 20, 2002, Response after Non-Final Rejection, Aug. 28, 2006.
U.S. Appl. No. 10/327,602, Lasken, filed Dec. 20, 2002, Restriction Requirement, Jun. 26, 2006.
U.S. Appl. No. 10/405,822, Abarzua et al., filed Mar. 31, 2003, Final Rejection, Sep. 11, 2008.
U.S. Appl. No. 10/405,822, Abarzua et al., filed Mar. 31, 2003, Request for Continued Examination, Dec. 28, 2007.
U.S. Appl. No. 10/405,822, Abarzua et al., filed Mar. 31, 2003, Mail Advisory Action, Nov. 9, 2007.
U.S. Appl. No. 10/405,822, Abarzua et al., filed Mar. 31, 2003, Amendment/Argument after Notice of Appeal, Oct. 30, 2007.
U.S. Appl. No. 10/405,822, Abarzua et al., filed Mar. 31, 2003, Notice of Appeal Filed, Oct. 30, 2007.
U.S. Appl. No. 10/405,822, Abarzua et al., filed Mar. 31, 2003, Mail Final Rejection, Apr. 30, 2007.
U.S. Appl. No. 10/405,822, Abarzua et al., filed Mar. 31, 2003, Response after Non-Final Action, Jan. 25, 2007.
U.S. Appl. No. 10/405,822, Abarzua et al., filed Mar. 31, 2003, Mail Non-Final Rejection, Aug. 2, 2006.
U.S. Appl. No. 10/405,822, Abarzua et al., filed Mar. 31, 2003, Response to Election / Restriction Filed, Jun. 6, 2006.
U.S. Appl. No. 10/405,822, Abarzua et al., filed Mar. 31, 2003, Mail Restriction Requirement, Dec. 13, 2005.
U.S. Appl. No. 10/454,946, Feaver et al., filed Jun. 4, 2003, Request for Continued Examination, Aug. 29, 2008.
U.S. Appl. No. 10/454,946, Feaver et al., filed Jun. 4, 2003, Advisory Action, Mar. 25, 2008.
U.S. Appl. No. 10/454,946, Feaver et al., filed Jun. 4, 2003, Amendment after Final, Mar. 25, 2008.
U.S. Appl. No. 10/454,946, Feaver et al., filed Jun. 4, 2003, Notice of Appeal Filed, Mar. 17, 2008.
U.S. Appl. No. 10/454,946, Feaver et al., filed Jun. 4, 2003, Amendment after Final, Feb. 8, 2008.
U.S. Appl. No. 10/454,946, Feaver et al., filed Jun. 4, 2003, Examiner Interview Summary Record, Jan. 29, 2008.
U.S. Appl. No. 10/454,946, Feaver et al., filed Jun. 4, 2003, Final Rejection, Sep. 18, 2007.
U.S. Appl. No. 10/454,946, Feaver et al., filed Jun. 4, 2003, Response after Non-Final Action, Jul. 5, 2007.
U.S. Appl. No. 10/454,946, Feaver et al., filed Jun. 4, 2003, Non-Final Rejection, Feb. 9, 2007.
U.S. Appl. No. 10/454,946, Feaver et al., filed Jun. 4, 2003, Response after Non-Final Action, Nov. 20, 2006.
U.S. Appl. No. 10/454,946, Feaver et al., filed Jun. 4, 2003, Non-Final Rejection, Jul. 26, 2006.
U.S. Appl. No. 10/454,946, Feaver et al., filed Jun. 4, 2003, Response to Election / Restriction Filed, May 4, 2006.
U.S. Appl. No. 10/454,946, Feaver et al., filed Jun. 4, 2003, Restriction Requirement, Feb. 6, 2006.
U.S. Appl. No. 09/920,571, Lasken et al., filed Jul. 31, 2001, Response to Election/Restriction Filed, May 7, 2007.
U.S. Appl. No. 09/920,571, Lasken et al., filed Jul. 31, 2001, Mail Restriction Requirement, Mar. 6, 2007.
U.S. Appl. No. 09/920,571, Lasken et al., filed Jul. 31, 2001, Request for Continued Examination (RCE) & Response to Office Action, Dec. 11, 2006.
U.S. Appl. No. 09/920,571, Lasken et al., filed Jul. 31, 2001, Mail Final Rejection, Jun. 12, 2006.
U.S. Appl. No. 09/920,571, Lasken et al., filed Jul. 31, 2001, Response after Non-Final Rejection, Mar. 29, 2006.
U.S. Appl. No. 09/920,571, Lasken et al., filed Jul. 31, 2001, Mail Non-Final Rejection, Nov. 1, 2005.
U.S. Appl. No. 09/920,571, Lasken et al., filed Jul. 31, 2001, Request for Continued Examination (RCE) & Response to Office Action, Aug. 19, 2005.
U.S. Appl. No. 09/920,571, Lasken et al., filed Jul. 31, 2001, Mail Advisory Action, Jun. 20, 2005.
U.S. Appl. No. 09/920,571, Lasken et al., filed Jul. 31, 2001, Amendment/Argument after Notice of Appeal, Jun. 2, 2005.
U.S. Appl. No. 09/920,571, Lasken et al., filed Jul. 31, 2001, Notice of Appeal Filed, Jun. 2, 2005.
U.S. Appl. No. 09/920,571, Lasken et al., filed Jul. 31, 2001, Mail final Rejection, Feb. 14, 2005.
U.S. Appl. No. 09/920,571, Lasken et al., filed Jul. 31, 2001, Response after Non-Final Action, Nov. 24, 2004.
U.S. Appl. No. 09/920,571, Lasken et al., filed Jul. 31, 2001, Mail Non-Final Rejection, Aug. 25, 2004.
U.S. Appl. No. 09/920,571, Lasken et al., filed Jul. 31, 2001, Request for Continued Examination (RCE), Jul. 12, 2004.
U.S. Appl. No. 09/920,571, Lasken et al., filed Jul. 31, 2001, Mail Advisory Action, Jun. 23, 2004.
U.S. Appl. No. 09/920,571, Lasken et al., filed Jul. 31, 2001, Amendment /Argument after Notice of Appeal, Jun. 1, 2004.
U.S. Appl. No. 09/920,571, Lasken et al., filed Jul. 31, 2001, Notice of Appeal Filed., Jun. 1, 2004.
U.S. Appl. No. 09/920,571, Lasken et al., filed Jul. 31, 2001, Mail Final Rejection, Feb. 18, 2004.
U.S. Appl. No. 09/920,571, Lasken et al., filed Jul. 31, 2001, Response after Non-Final Action, Oct. 17, 2003.
U.S. Appl. No. 09/920,571, Lasken et al., filed Jul. 31, 2001, Mail Non-Final Rejection, Dec. 20, 2002.

U.S. Appl. No. 09/920,571, Lasken et al., filed Jul. 31, 2001, Supplemental Response, Oct. 3, 2002.
U.S. Appl. No. 09/920,571, Lasken et al., filed Jul. 31, 2001, Supplemental Response, Sep. 20, 2002.
U.S. Appl. No. 09/920,571, Lasken et al., filed Jul. 31, 2001, Mail Notice of Informal or Non-Responsive Amendment, Aug. 27, 2002.
U.S. Appl. No. 09/920,571, Lasken et al., filed Jul. 31, 2001, Mail Non-Final Rejection, Dec. 12, 2001.
U.S. Appl. No. 09/577,444, Kingsmore et al., filed Jul. 31, 2001, Issue Notification, Aug. 30, 2001.
U.S. Appl. No. 09/577,444, Kingsmore et al., filed May 24, 2000, Notice of Allowance, Mar. 29, 2001.
U.S. Appl. No. 09/577,444, Kingsmore et al., filed May 24, 2000, Examiner Interview Summary Record, Mar. 22, 2001.
U.S. Appl. No. 09/897,665, Kingsmore et al., filed Jul. 2, 2001, Issue Notification, Dec. 11, 2003.
U.S. Appl. No. 09/897,665, Kingsmore et al., filed Jul. 2, 2001, Notice of Allowance, Jul. 30, 2003.
U.S. Appl. No. 09/897,665, Kingsmore et al., filed Jul. 2, 2001, Notice of Appeal Filed, Jun. 2, 2003.
U.S. Appl. No. 09/897,665, Kingsmore et al., filed Jul. 2, 2001, Terminal Disclaimer Filed, Jun. 2, 2003.
U.S. Appl. No. 09/897,665, Kingsmore et al., filed Jul. 2, 2001, Final Rejection, Feb. 25, 2003.
U.S. Appl. No. 09/897,665, Kingsmore et al., filed Jul. 2, 2001, Response after Non-Final Action, Dec. 10, 2002.
U.S. Appl. No. 09/897,665, Kingsmore et al., filed Jul. 2, 2001, Non-Final Rejection., Jul. 19, 2002.
U.S. Appl. No. 09/910,372, Bandaru et al., filed Jul. 20, 2001, Issue Notification, Oct. 2, 2003.
U.S. Appl. No. 09/910,372, Bandaru et al., filed Jul. 20, 2001, Notice of Allowance, Apr. 8, 2003.
U.S. Appl. No. 09/910,372, Bandaru et al., filed Jul. 20, 2001, Response after Non-Final Action, Mar. 20, 2003.
U.S. Appl. No. 09/910,372, Bandaru et al., filed Jul. 20, 2001, Response after Non-Final Action, Jan. 22, 2003.
U.S. Appl. No. 09/910,372, Bandaru et al., filed Jul. 20, 2001, Non-Final Rejection, Nov. 13, 2002.
U.S. Appl. No. 09/910,372, Bandaru et al., filed Jul. 20, 2001, Response to Election / Restriction Filed, Oct. 4, 2002.
U.S. Appl. No. 09/910,372, Bandaru et al., filed Jul. 20, 2001, Restriction Requirement, Sep. 17, 2002.
U.S. Appl. No. 10/465,759, Bandaru et al., filed Jun. 19, 2003, Issue Notification, Oct. 14, 2004.
U.S. Appl. No. 10/465,759, Bandaru et al., filed Jun. 19, 2003, Notice of Allowance, May 4, 2004.
U.S. Appl. No. 10/465,759, Bandaru et al., filed Jun. 19, 2003, Response after Non-Final Action, Apr. 12, 2004.
U.S. Appl. No. 10/465,759, Bandaru et al., Non-Final Rejection, Jan. 8, 2004.
U.S. Appl. No. 09/723,685, Abarzua, filed Nov. 28, 2000, Issue Notification, Dec. 5, 2002.
U.S. Appl. No. 09/723,685, Abarzua, filed Nov. 28, 2000, Notice of Allowance, Apr. 17, 2002.
U.S. Appl. No. 09/723,685, Abarzua, filed Nov. 28, 2000, Response after Non-Final Action, Dec. 10, 2001.
U.S. Appl. No. 09/723,685, Abarzua, filed Nov, 28, 2000, Non-Final Rejection, Aug. 28, 2001.
U.S. Appl. No. 09/723,685, Abarzua, filed Nov. 11, 2000, Response after Non-Final Action, Jun. 15, 2001.
U.S. Appl. No. 09/723,685, Abarzua, filed Nov. 28, 2000, Non-Final Rejection, Mar. 13, 2001.
U.S. Appl. No. 10/196,539, Abarzua, filed Jul. 16, 2002, Issue Notification, Apr. 19, 2006.
U.S. Appl. No. 10/196,539, Abarzua, filed Jul. 16, 2002, Notice of Allowance, Nov. 15, 2005.
U.S. Appl. No. 10/196,539, Abarzua, filed Jul. 16, 2002, Terminal Disclaimer Filed, Aug. 12, 2005.
U.S. Appl. No. 10/196,539, Abarzua, filed Jul. 16, 2002, Response after Non-Final Action, Aug. 12, 2005.
U.S. Appl. No. 10/196,539, Abarzua, filed Jul. 16, 2002, Non-Final Rejection, Mar. 10, 2005.
U.S. Appl. No. 11/429,549, Abarzua, filed May 5, 2006, Examiner Interview Summary, Oct. 15, 2008.
U.S. Appl. No. 11/429,549, Abarzua, filed May 5, 2006, Abandonment, Oct. 15, 2008.
U.S. Appl. No. 11/429,549, Abarzua, filed May 5, 2006, Non-Final Rejection, Mar. 26, 2008.
U.S. Appl. No. 11/429,549, Abarzua, filed May 5, 2006, Notice of Publication, Jan. 18, 2007.
U.S. Appl. No. 11/429,549, Abarzua, filed May 5, 2006, Preliminary Amendment, May 5, 2006.
U.S. Appl. No. 09/827,289, Abarzua, filed Apr. 5, 2001, Issue Notification, Jul. 29, 2004.
U.S. Appl. No. 09/827,289, Abarzua, filed Apr. 5, 2001, Notice of Allowance, Apr. 1, 2004.
U.S. Appl. No. 09/827,289, Abarzua, filed Apr. 5, 2001, Supplemental Response, Feb. 17, 2004.
U.S. Appl. No. 09/827,289, Abarzua, filed Apr. 5, 2001, Notice of Informal of Non-Responsive Amendment, Feb. 2, 2004.
U.S. Appl. No. 09/827,289, Abarzua, filed Apr. 5, 2001, Response after Non-Final Action, Jan. 22, 2004.
U.S. Appl. No. 09/827,289, Abarzua, filed Apr. 5, 2001, Non-Final Rejection, Sep. 29, 2003.
U.S. Appl. No. 09/827,289, Abarzua, filed Apr. 5, 2001, Request for Continued Examination (RCE), Aug. 6, 2003.
U.S. Appl. No. 09/827,289, Abarzua, filed Apr. 5, 2001, Advisory Action, Jun. 2, 2003.
U.S. Appl. No. 09/827,289, Abarzua, filed Apr. 5, 2001, Amendment after Final Rejection, May 15, 2003.
U.S. Appl. No. 09/827,289, Abarzua, filed Apr. 5, 2001, Final Rejection, Feb. 10, 2003.
U.S. Appl. No. 09/827,289, Abarzua, filed Apr. 5, 2001, Response after Non-Final Action, Jan. 21, 2003.
U.S. Appl. No. 09/827,289, Abarzua, filed Apr. 5, 2001, Non-Final Rejection, Jul. 29, 2002.
U.S. Appl. No. 09/827,289, Abarzua, filed Apr. 5, 2001, Response to Election / Restriction Filed, Jun. 24, 2002.
U.S. Appl. No. 09/827,289, Abarzua, filed Apr. 5, 2001, Restriction Requirement, Jun. 11, 2002.
U.S. Appl. No. 10/177,629, Wiltshire, filed Jun. 19, 2002, Examiner Interview Summary, Sep. 20, 2007.
U.S. Appl. No. 10/177,629, Wiltshire, filed Jun. 19, 2002, Abandonment for failure to respond to office action, Sep. 15, 2007.
U.S. Appl. No. 10/177,629, Wiltshire, filed Jun. 19, 2002, Final Rejection, Aug. 21, 2006.
U.S. Appl. No. 10/177,629, Wiltshire, filed Jun. 19, 2002, Response after Non-Final Action & Terminal Disclaimer, Jun. 12, 2006.
U.S. Appl. No. 10/177,629, Wiltshire, filed Jun. 19, 2002, Non-Final Rejection, Jan. 10, 2006.
U.S. Appl. No. 10/177,629, Wiltshire, filed Jun. 19, 2002, Response to Election / Restriction Filed, Oct. 27, 2005.
U.S. Appl. No. 10/177,629, Wiltshire, filed Jun. 19, 2002, Notice of Informal or Non-Responsive Amendment, Sep. 30, 2005.
U.S. Appl. No. 10/177,629, Wiltshire, filed Jun. 19, 2002, Response to Election / Restriction Filed, Sep. 19, 2005.
U.S. Appl. No. 09/831,736, Shao, filed Aug. 17, 2001, Issue Notification, Feb. 9, 2005.
U.S. Appl. No. 09/931,736, Shao, filed Aug. 17, 2001, Notice of Allowance, Nov. 18, 2004.
U.S. Appl. No. 09/931,736, Shao, filed Aug. 17, 2001, Appeal Brief Filed, Aug. 27, 2004.
U.S. Appl. No. 09/931,736, Shao, filed Aug. 17, 2001, Advisory Action, May 4, 2004.
U.S. Appl. No. 09/931,736, Shao, filed Aug. 17, 2001, Amendment/Argument after Notice of Appeal, Mar. 1, 2004.
U.S. Appl. No. 09/931,736, Shao, filed Aug. 17, 2001, Notice of Appeal Filed, Mar. 1, 2004.
U.S. Appl. No. 09/931,736, Shao, filed Aug. 17, 2001, Final Rejection, Dec. 3, 2003.
U.S. Appl. No. 09/931,736, Shao, filed Aug. 17, 2001, Response after Non-Final Action, Sep. 22, 2003.
U.S. Appl. No. 09/931,736, Shao, filed Aug. 17, 2001, Non-Final Rejection, Jun. 30, 2003.

U.S. Appl. No. 09/931,736, Shao, filed Aug. 17, 2001, Response to Election / Restriction Filed, May 16, 2003.

U.S. Appl. No. 09/931,736, Shao, filed Aug. 17, 2001, Restriction Requirement, Apr. 15, 2003.

U.S. Appl. No. 10/931,015, Shao, filed Aug. 31, 2004, Abandonment for Failure to Respond to Office Action, Aug. 8, 2006.

U.S. Appl. No. 10/177,629, Wiltshire, filed Jun. 19, 2002, Restriction Requirement, Mar. 17, 2005.

U.S. Appl. No. 10/931,015, Shao, filed Aug. 31, 2004, Final Rejection, Jan. 9, 2006.

U.S. Appl. No. 10/931,015, Shao, filed Aug. 31, 2004, Response after Non-Final Action, Aug. 26, 2005.

U.S. Appl. No. 10/931,015, Shao, filed Aug. 31, 2004, Non-Final Rejection, May 24, 2005.

U.S. Appl. No. 10/931,015, Shao, filed Aug. 31, 2004, Response to Election / Restriction Filed, Feb. 28, 2005.

U.S. Appl. No. 10/931,015, Shao, filed Aug. 31, 2004, Restriction Requirement, Jan. 24, 2005.

U.S. Appl. No. 11/744,553, Korfhage et al., filed May 4, 2007, Non-Final Rejection, Aug. 19, 2008.

U.S. Appl. No. 11/744,553, Korfhage et al., filed May 4, 2007, Response to Restriction Requiement, Jun. 5, 2008.

U.S. Appl. No. 11/744,553, Korfhage et al., filed May 4, 2007, Requirement for Restriction, May 16, 2008.

U.S. Appl. No. 11/744,553, Korfhage et al., filed May 4, 2007, Notice of Publication, Mar. 6, 2008.

U.S. Appl. No. 11/887,678, Korfhage, No Transaction History Generated.

U.S. Appl. No. 11/991,435, Korfhage, Preliminary Amendment, Mar. 3, 2008.

U.S. Appl. No. 08/563,912, Lizardi, filed Nov. 21, 1995, Issue Notification, Nov. 23, 1998.

U.S. Appl. No. 08/563,912, Lizardi, filed Nov. 21, 1995, Notice of Allowance, Aug. 14, 1998.

U.S. Appl. No. 08/563,912, Lizardi, filed Nov. 21, 1995, Examiner Interview Summary Record, Aug. 10, 1998.

U.S. Appl. No. 08/563,912, Lizardi, filed Nov. 21, 1995, Amendment/Argument after Notice of Appeal, Aug. 6, 1998.

U.S. Appl. No. 08/563,912, Lizardi, filed Nov. 21, 1995, Notice of Appeal Filed, Jun. 15, 1998.

U.S. Appl. No. 08/563,912, Lizardi, filed Nov. 21, 1995, Final Rejection, Dec. 9, 1997.

U.S. Appl. No. 08/563,912, Lizardi, filed Nov. 21, 1995, Response after Non-Final Action, Sep. 2, 1997.

U.S. Appl. No. 08/563,912, Lizardi, filed Nov. 21, 1995, Notice of Restarted Response Period, Feb. 28, 1997.

U.S. Appl. No. 08/563,912, Lizardi, filed Nov. 21, 1995, Non-Final Rejection, Feb. 7, 1997.

U.S. Appl. No. 08/563,912, Lizardi, filed Nov. 21, 1995, Response to Election / Restriction Filed, Oct. 31, 1996.

U.S. Appl. No. 08/563,912, Lizardi, filed Nov. 21, 1995, Restriction Requirement, Sep. 24, 1996.

U.S. Appl. No. 09/132,553, Lizardi, filed Aug. 11, 1998, Issue Notification, Mar. 15, 2001.

U.S. Appl. No. 09/132,553, Lizardi, filed Aug. 11, 1998, Notice of Allowance, Nov. 7, 2000.

U.S. Appl. No. 09/132,553, Lizardi, filed Aug. 11, 1998, Preliminary Amendment, Aug. 17, 2000.

U.S. Appl. No. 09/132,553, Lizardi, filed Aug. 11, 1998, Non-Final Rejection, Apr. 11, 2000.

U.S. Appl. No. 09/132,553, Lizardi, filed Aug. 11, 1998, Response after Non-Final Action & Terminal Disclaimer Filed, Jan. 19, 2000.

U.S. Appl. No. 09/132,553, Lizardi, filed Aug. 11, 1998, Non-Final Rejection, Sep. 13, 1999.

U.S. Appl. No. 09/644,723, Lizardi, filed Aug. 23, 2000, Issue Notification, Jan. 18, 2002.

U.S. Appl. No. 09/644,723, Lizardi, filed Aug. 23, 2000, Issue Notification, Oct. 1, 2001.

U.S. Appl. No. 09/644,723, Lizardi, filed Aug. 23, 2000, Response after Non-Final Action & Terminal Disclaimer Filed, Jul. 16, 2001.

U.S. Appl. No. 09/644,723, Lizardi, filed Aug. 23, 2000, Non-Final Rejection, Mar. 13, 2001.

U.S. Appl. No. 09/132,552, Lizardi, filed Aug. 11, 1998, Issue Notification, Jan. 19, 2001.

U.S. Appl. No. 09/132,552, Lizardi, filed Aug. 11, 1998, Notice of Allowance, Jul. 12, 2000.

U.S. Appl. No. 09/132,552, filed Aug. 11, 1998, Amendment after Final Rejection, Jun. 19, 2000.

U.S. Appl. No. 09/132,552, Lizardi, filed Aug. 11, 1998, Final Rejection, Apr. 6, 2000.

U.S. Appl. No. 09/132,552, Lizardi, filed Aug. 11, 1998, Response after Non-Final Action & Terminal Disclaimer Filed, Jan. 19, 2000.

U.S. Appl. No. 09/132,552, Lizardi, filed Aug. 11, 1998, Non-Final Rejection, Sep. 13, 1999.

U.S. Appl. No. 10/038,718, Lizardi, filed Jan. 2, 2002, Issue Notification, Sep. 9, 2004.

U.S. Appl. No. 10/038,718, Lizardi, filed Jan. 2, 2002, Notice of Allowance, Apr. 21, 2004.

U.S. Appl. No. 10/038,718, Lizardi, filed Jan. 2, 2002, Response after Non-Final Action & Terminal Disclaimer Filed, Jan. 20, 2004.

U.S. Appl. No. 10/038,718, Lizardi, filed Jan. 2, 2002, Non-Final Rejection, Oct. 22, 2003.

U.S. Appl. No. 10/038,718, Lizardi, filed Jan. 2, 2002, Response to Election / Restriction Filed, Jul. 16, 2003.

U.S. Appl. No. 10/038,718, Lizardi, filed Jan. 2, 2002, Restriction Requirement, Mar. 13, 2003.

U.S. Appl. No. 10/896,513, Lizardi, filed Jul. 22, 2004, Request for Continued Examination, Aug. 29, 2008.

U.S. Appl. No. 10/896,513, Lizardi, filed Jul. 22, 2004, Advisory Action, Jul. 23, 2008.

U.S. Appl. No. 10/896,513, Lizardi, filed Jul. 22, 2004, Amendment After Final Rejection, Jun. 16, 2008.

U.S. Appl. No. 10/896,513, Lizardi, filed Jul. 22, 2004, Final Rejection, Mar. 18, 2008.

U.S. Appl. No. 10/896,513, Lizardi, filed Jul. 22, 2004, Amendment After Non-Final Rejection, Dec. 11, 2007.

U.S. Appl. No. 10/896,513, Lizardi, filed Jul. 22, 2004, Non-Final Rejection, Jun. 11, 2007.

U.S. Appl. No. 10/896,513, Lizardi, filed Jul. 22, 2004, Response to Election / Restriction Filed, Mar. 29, 2007.

U.S. Appl. No. 10/896,513, Lizardi, filed Jul. 22, 2004, Restriction Requirement, Jan. 19, 2007.

U.S. Appl. No. 08/946,732, Lizardi, filed Oct. 8, 1997, Issue Notification, Sep. 8, 2000.

U.S. Appl. No. 08/946,732, Lizardi, filed Oct. 8, 1997, Notice of Allowance, Jun. 22, 1999.

U.S. Appl. No. 08/946,732, Lizardi, filed Oct. 8, 1997, Examiner Interview Summary Record, Jun. 9, 1999.

U.S. Appl. No. 08/946,732, Lizardi, filed Oct. 8, 1997, Response after Non-Final Action, Apr. 5, 1999.

U.S. Appl. No. 08/946,732, Lizardi, filed Oct. 8, 1997, Non-Final Rejection, Sep. 28, 1998.

U.S. Appl. No. 09/397,915, Lizardi, filed Sep. 17, 1999, Petition Decision - Accept Late Payment of Maintenance Fees - Granted, Oct. 31, 2005.

U.S. Appl. No. 09/397,915, Lizardi, filed Sep. 17, 1999, Petition to Accept Late Payment of Maintenance Fee Payment Filed, Oct. 13, 2005.

U.S. Appl. No. 09/397,915, Lizardi, filed Sep. 17, 1999, Expire Patent, Sep. 28, 2005.

U.S. Appl. No. 09/397,915, filed Sep. 17, 1999, Issue Notification, Aug. 9, 2001.

U.S. Appl. No. 09/397,915, Lizardi, filed Sep. 17, 1999, Notice of Allowance, Apr. 9, 2001.

U.S. Appl. No. 09/397,915, Lizardi, filed Sep. 17, 1999, Examiner Interview Summary Record, Apr. 4, 2001.

U.S. Appl. No. 09/397,915, Lizardi, filed Sep. 17, 1999, Terminal Disclaimer Filed, Jan. 29, 2001.

U.S. Appl. No. 09/397,915, Lizardi, filed Sep. 17, 1999, Response after Non-Final Action, Jan. 22, 2001.

U.S. Appl. No. 09/397,915, Lizardi, filed Sep. 17, 1999, Non-Final Rejection, Aug. 14, 2000.

U.S. Appl. No. 09/911,226, Lizardi, filed Jul. 23, 2001, Issue Notification, Oct. 16, 2003.

U.S. Appl. No. 09/911,226, Lizardi, filed Jul. 23, 2001, Notice of Allowance, Jun. 3, 2003.
U.S. Appl. No. 09/911,226, Lizardi, filed Jul. 23, 2001, Response after Non-Final Action & Terminal Disclaimer Filed, Mar. 19, 2003.
U.S. Appl. No. 09/911,226, Lizardi, filed Jul. 23, 2001, Non-Final Rejection, Dec. 18, 2002.
U.S. Appl. No. 10/700,018, Lizardi, filed Nov. 3, 2003, Final Rejection, Sep. 15, 2008.
U.S. Appl. No. 10/700,018, Lizardi, filed Nov. 3, 2003, Amendment after Non-Final Rejection, Jun. 12, 2008.
U.S. Appl. No. 10/700,018, Lizardi, filed Nov. 3, 2003, Non-Final Rejection, Jan. 24, 2008.
U.S. Appl. No. 10/700,018, Lizardi, filed Nov. 3, 2003, Response after Non-Final Action, Oct. 31, 2007.
U.S. Appl. No. 10/700,018, Lizardi, filed Nov. 3, 2003, Non-Final Rejection, Aug. 8, 2007.
U.S. Appl. No. 10/700,018, Lizardi, filed Nov. 3, 2003, Response after Non-Final Action, May 14, 2007.
U.S. Appl. No. 10/700,018, Lizardi, filed Nov. 3, 2003, Non-Final Rejection, Nov. 14, 2006.
U.S. Appl. No. 10/700,018, Lizardi, filed Nov. 3, 2003, Response after Non-Final Action, Aug. 28, 2006.
U.S. Appl. No. 10/700,018, Lizardi, filed Nov. 3, 2003, Request for Extension fo Time - Granted, Aug. 28, 2006.
U.S. Appl. No. 10/700,018, Lizardi, filed Nov. 3, 2003, Non-Final Rejection, May 18, 2006.
U.S. Appl. No. 10/700,018, Lizardi, filed Nov. 3, 2003, Preliminary Amendment, Nov. 3, 2003.
U.S. Appl. No. 09/357,487, Lizardi, filed Jul. 20, 1999, Issue Notification, Oct. 25, 2001.
U.S. Appl. No. 09/357,487, Lizardi, filed Jul. 20, 1999, Notice of Allowance, Jun. 5, 2001.
U.S. Appl. No. 09/357,487, Lizardi, filed Jul. 20, 1999, Examiner Interview Summary Record, May 30, 2001.
U.S. Appl. No. 09/357,487, Lizardi, filed Jul. 20, 1999, Examiner Interview Summary Record, May 28, 2001.
U.S. Appl. No. 09/357,487, Lizardi, filed Jul. 20, 1999, Amendment after Final Rejection, May 21, 2001.
U.S. Appl. No. 09/357,487, Lizardi, filed Jul. 20, 1999, Final Rejection, Feb. 13, 2001.
U.S. Appl. No. 09/357,487, Lizardi, filed Jul. 20, 1999, Response after Non-Final Action, Jan. 29, 2001.
U.S. Appl. No. 09/357,487, Lizardi, filed Jul. 20, 1999, Non-Final Rejection, Oct. 25, 2000.
U.S. Appl. No. 09/357,487, Lizardi, filed Jul. 20, 1999, Response after Non-Final Action, Sep. 18, 2000.
U.S. Appl. No. 09/357,487, Lizardi, filed Jul. 20, 1999, Non-Final Rejection, May 12, 2000.
PCT/US02/02601, filed Jan. 30, 2002, Molecular Staging, Inc., International Preliminary Examination Report, Mar. 29, 2004.
PCT/US02/02601, filed Jan. 30, 2002, Molecular Staging, Inc., International Search Report, Oct. 3, 2002.
01928481.9, filed Apr. 12, 2001, Molecular Staging, Inc., Communication under Rule 51(4) EPC, Sep. 11, 2007.
01928481.9, filed Apr. 12, 2001, Molecular Staging, Inc., Response to Examination Report, Nov. 27, 2006.
01928481.9, filed Apr. 12, 2001, Molecular Staging, Inc., Response to Examination Report, Mar. 6, 2006.
01928481.9, filed Apr. 12, 2001, Molecular Staging, Inc., Examination Report, May 25, 2005.
PCT/US01/11947, filed Apr. 12, 2001, Molecular Staging, Inc., International Preliminary Examination Report, Apr. 30, 2003.
PCT/US01/11947, filed Apr. 12, 2001, Molecular Staging, Inc., International Search Report, Mar. 20, 2003.
PCT/US01/19657, filed Jun. 20, 2001, Molecular Staging, Inc., International Preliminary Examination Report, Feb. 5, 2003.
PCT/US01/19657, filed Jun. 20, 2001, Molecular Staging, Inc., International Search Report, Dec. 27, 2001.
200207285-8, filed Jun. 20, 2001, Molecular Staging, Inc., Issue Notification, Dec. 16, 2002.
PCT/US01/20933, filed Jul. 2, 2001, Molecular Staging, Inc., Yale University, International Preliminary Examination Report, Dec. 30, 2002.
PCT/US01/20933, filed Jul. 2, 2001, Molecular Staging, Inc., Yale University, International Search Report, Jan. 10, 2002.
PCT/US02/15045, filed May 10, 2002, Molecular Staging, Inc., International Preliminary Examination Report, Oct. 26, 2004.
PCT/US02/15045, filed May 10, 2002, Molecular Staging, Inc., International Search Report, Apr. 10, 2003.
EP 00950759.9, filed Jul. 2, 2001, Molecular Staging, Inc., European Search Report, Jul. 12, 2004.
02801776.2, filed Oct. 15, 2002, Molecular Staging, Inc., European Search Report, Nov. 4, 2007.
02801776.2, filed Oct. 15, 2002, Molecular Staging, Inc., European Search Report, Nov. 7, 2006.
PCT/US02/33244, filed Oct. 15, 2002, Molecular Staging, Inc., International Preliminary Examination Report, Jul. 13, 2004.
PCT/US02/33244, filed Oct. 15, 2002, Molecular Staging, Inc., International Search Report, Apr. 29, 2004.
PCT/US96/18812, filed Nov. 21, 1996, Yale University, International Preliminary Examination Report, Jan. 28, 1998.
PCT/US96/18812, filed Nov. 21, 1996, Yale University, International Search Report, Jun. 3, 1997.
PCT/US96/18812, filed Nov. 21, 1996, Yale University, Written Opinion, Aug. 21, 1997.
PCT/US96/18812, filed Nov. 21, 1996, Yale University, International Search Report, Nov. 21, 1995.
PCT/US03/00678, filed Jan. 9, 2003, Molecular Staging, Inc., International Search Report, Aug. 14, 2003.
99969209.8, filed Dec. 14, 1999, Molecular Staging, Inc., European Search Report, Feb. 21, 2003.
PCT/AU99/01110, filed Dec. 14, 1999, Diatech Pty. Ltd., International Search Report, Jun. 22, 2000.
03796961.5, filed Dec. 11, 2003, Qiagen GMBH, European Search Report, Jan. 16, 2007.
PCT/US03/39430, filed Dec. 11, 2003, Qiagen GMBH, International Search Report, Nov. 11, 2004.
PCT/US01/20217, filed Jun. 27, 2001, Molecular Staging, Inc., International Preliminary Examination Report, Dec. 6, 2004.
PCT/US01/20217, filed Jun. 27, 2001, Molecular Staging, Inc., International Search Report, Apr. 3, 2003.
PCT/US00/16130, filed Jun. 12, 2000, Molecular Staging, Inc., International Preliminary Examination Report, Dec. 28, 2004.
PCT/US00/16130, filed Jun. 12, 2000, Molecular Staging, Inc., International Search Report, Nov. 22, 2001.
PCT/US02/00005, filed Jan. 4, 2002, Molecular Staging, Inc., International Preliminary Examination Report, Jul. 5, 2003.
PCT/US02/00005, filed Jan. 4, 2002, Molecular Staging, Inc., International Search Report, May 22, 2003.
PCT/US00/32370, filed Nov. 28, 2000, Molecular Staging, Inc., International Search Report, Jul. 11, 2002.
PCT/US01/11151, filed Apr. 5, 2001, Molecular Staging, Inc., International Preliminary Examination Report, Oct. 15, 2004.
PCT/US01/11151, filed Apr. 5, 2001, Molecular Staging, Inc., International Search Report, Oct. 18, 2002.
PCT/US02/19443, filed Jun. 19, 2002, Molecular Staging, Inc., International Preliminary Examination Report, Feb. 16, 2006.
PCT/US02/19443, filed Jun. 19, 2002, Molecular Staging, Inc., International Search Report, Oct. 10, 2003.
PCT/US02/27097, filed Aug. 14, 2002, Molecular Staging, Inc., International Preliminary Examination Report, Oct. 12, 2004.
PCT/US02/27097, filed Aug. 14, 2002, Molecular Staging, Inc., International Search Report, Jan. 29, 2003.
7118804.9, filed Oct. 18, 2007, Qiagen GMBH, European Search Report, Feb. 15, 2008.
PCT/US98/21177, filed Oct. 8, 1998, Yale University, International Preliminary Examination Report, Oct. 12, 1999.
PCT/US98/21177, filed Oct. 8, 1998, Yale University, International Search Report, Apr. 15, 1999.
PCT/US99/16373, filed Jul. 20, 1999, Yale University, International Search Report, Nov. 9, 2000.

* cited by examiner

DETECTION METHOD USING DISSOCIATED ROLLING CIRCLE AMPLIFICATION

FIELD OF THE INVENTION

The disclosed invention is generally in the area of detection of analytes, and specifically in the area of detection of analytes using rolling circle amplification.

BACKGROUND OF THE INVENTION

The information content of the genome is carried as deoxyribonucleic acid (DNA). The size and composition of a given genomic sequence determines the form and function of the resultant organism. In general, genomic complexity is proportional to the complexity of the organism. Relatively simple organisms such as bacteria have genomes of about 1-5 million megabases while mammalian genomes are approximately 3000 megabases. The genome is generally divided into distinct segments known as chromosomes. The bacterium *Escherichia coli* (*E. coli*) contains a single circular chromosome, whereas the human genome consists of 24 chromosomes.

Genomic DNA exists as a double-stranded polymer containing four DNA bases (A, G, C, and T) tethered to a sugar-phosphate backbone. The order of the bases along the DNA is the primary sequence of the DNA. The genome of an organism contains both protein coding and non-coding regions, including exons and introns, promoter and gene regulatory regions, and non-functional DNA. Genome analysis can provide a quantitative measure of gene copy number and chromosome number, as well as the presence of single base differences in the primary sequence of the DNA. Single base changes that are inherited are referred to as polymorphisms, whereas those that are acquired during the life of an organism are known as mutations. Genomic analysis at the DNA level does not provide a measure of gene expression (that is, the process by which RNA and protein copies of the coding sequences are synthesized).

All of the cells from a given organism are assumed to contain identical genomes, while genomes from different individuals of the same species are typically about 99.9% identical. The 0.1% polymorphism rate among individuals (Wang et al., *Science* 280: 1077 (1998)) is significant in that approximately three million polymorphisms are expected to be found upon complete sequencing of any two human genomes. If single base changes occur in protein coding segments, polymorphisms can alter the protein sequence and therefore change the biochemical activity of the protein.

The DNA genome consists of discrete functional regions known as genes. Genomes of simple organisms such as bacteria contain approximately 1000 genes (Fleischmann et al., *Science* 269: 496 (1995)), whereas the human genome is estimated to contain about 100,000 genes (Fields et al., *Nature Genet.* 7: 345 (1994)). Genomic analysis at the mRNA level can be used as a measure of gene expression. Expression levels for each gene are determined by a combination of genetic and environmental factors. The genetic factors include the precise DNA sequence of gene regulatory regions such as promoters, enhancers, and splice sites. Polymorphisms in the DNA are thus expected to contribute some of the differences in gene expression among individuals of the same species. Expression levels are also affected by environmental factors, including temperature, stress, light, and signals that lead to changes in the levels of hormones and other signaling substances. For this reason, RNA analysis provides information not only about the genetic potential of an organism, but also about changes in functional state (M. Schena and R. W. Davis, *DNA Microarrays: A Practical Approach.* (Oxford University Press, New York, 1999) 1-16.)

The second step in gene expression is the synthesis of protein from mRNA. A unique protein is encoded by each mRNA, such that every three nucleotides of mRNA encodes one amino acid of the polypeptide chain, with the linear order of the nucleotides represented as a linear sequence of amino acids. Once synthesized, the protein assumes a unique three-dimensional conformation that is determined largely by the primary amino acid sequence. Proteins impart the functional instructions of the genome by performing a wide range of biochemical activities including roles in gene regulation, metabolism, cell structure, and DNA replication.

Individuals in a population may have differences in protein activity due to polymorphisms that either alter the primary amino acid sequence of the proteins or perturb steady state protein levels by altering gene expression. Similar to mRNA levels, protein levels can also change in response to changes in the environment; moreover, protein levels are also subject to translational and post-translational control which do not effect mRNA levels directly (Schena and David, 1999). Proteomics analysis provides data on when or if a predicted gene product is actually translated, the level and type of post-translational modification it may undergo and its relative concentration compared with other proteins (Humphrey-Smith and Blackstock, *J. Protein. Chem.* 16: 537-544 (1997)). After DNA is transcribed into mRNA, the exons may be spliced in different ways before being translated into proteins. Following the translation of mRNA by ribosomes, proteins are usually post-translationally modified by the addition of different chemical groups such as carbohydrate, lipid and phosphate groups, as well as through the proteolytic cleavage of specific peptide bonds. These chemical modifications are crucial to modulating protein function but are not directly coded for by genes. Furthermore, both mRNA and protein are continually being synthesized and degraded, and thus final levels of protein are not easily obtainable by measuring mRNA levels (Patton, *J. Chromatogr.* 722: 203-223, (1999); Patton et al., *J. Biol. Chem.* 270: 21404-21410 (1995)). So while mRNA levels are often extrapolated to indicate the levels of expressed proteins, it is not surprising that there is little correlation between the abundance of mRNA species and the actual amounts of proteins that they code for (Anderson and Seilhamer, *Electrophoresis* 18: 533-537; Gygi et al., *Mol. Cell. Biol.* 19: 1720-1730 (1999)).

A growing body of evidence suggests that changes in gene and protein expression may correlate with the onset of a given human disease (Schena and Davis, 1999). Proteomic analysis of disease tissues should allow the identification of proteins whose expression is altered in a given illness. Many small molecules may also alter protein expression at a global level. Combining information about altered expression in a disease state with the changes that result from treatment with a small molecule would provide valuable information about classes of molecules that may be effective in combating a given disease. Proteomics thus has a role in processes such as lead compound screening and optimization, toxicity, pharmacodynamics, and drug efficacy.

A pivotal component of proteomics is its ability to accurately quantify vast numbers of proteins accurately and reproducibly. Typically, proteomics entails the simultaneous separation of proteins from a biological sample, and the quantitation of the relative abundance of the proteins resolved during the separation. Proteomics currently relies heavily on two-dimensional (2-D) gel electrophoresis. However, obtaining information concerning global protein expression using 2-D gels is technically difficult, and semiautomated procedures to carry out this process are in their infancy (Patton, *Biotechniques* 28: 944-957 (2000)). Furthermore, the commonly used stains for evaluating protein expression in 2-D gels (such as Coomassie Blue, colloidal gold and silver stain) do not provide the requisite dynamic range to be effective in this capacity. These stains are linear over only a 10- to 40-fold range, whereas the abundance of individual proteins differs by as much as four orders of magnitude (Brush, *The Scientist* 12:16-22, 1998; Wirth and Romano, *J. Chromatogr* 698: 123-143 (1995)). In addition, low abundance proteins, such as transcription factors and kinases that are present in 1-2000 copies per cell, often represent species that perform important regulatory functions. The accurate detection of such low-abundance proteins is an important challenge to proteomics. Methods have recently been introduced to directly quantify the relative abundance of proteins in two different samples by mass spectrometry. However, the linear dynamic range of these methods has been demonstrated over only a four- to ten-fold range (Gygi et al. 1999; Oda et al., *Proc. Natl. Acad. Sci USA* 96: 6591-6596 (1999)).

It has been noted that developing microarray technologies would make possible the simultaneous, ultra-sensitive measurement of hundreds or even thousands of substances in a small sample (Ekins, *Clin. Chem.* 44: 2015-2030 (1998)). This approach has been difficult to put into practice, however, because the extremely small volumes (about 0.5-5 nl) of sample used to create spots on these microarrays makes it necessary to utilize methods of analyte detection that are extremely sensitive. Rolling Circle Amplification (RCA) driven by DNA polymerase can replicate circular oligonucleotide probes with either linear or geometric kinetics under isothermal conditions (Lizardi et al., *Nature Genet.* 19: 225-232 (1998)). If a single primer is used, RCA generates in a few minutes a linear chain of hundreds or thousands of tandemly-linked DNA copies of a target which is covalently linked to that target. Generation of a linear amplification product permits both spatial resolution and accurate quantitation of a target. DNA generated by RCA can be labeled with fluorescent oligonucleotide tags that hybridize at multiple sites in the tandem DNA sequences. RCA can be used with fluorophore combinations designed for multiparametric color coding (Speicher et al., *Nature Genet.* 12:368-375 (1996)), thereby markedly increasing the number of targets that can be analyzed simultaneously. RCA technologies can be used in solution, in situ and in microarrays. In solid phase formats, detection and quantitation can be achieved at the level of single molecules (Lizardi et al., 1998).

BRIEF SUMMARY OF THE INVENTION

Disclosed are compositions and methods for detecting small quantities of analytes such as proteins and peptides. The method involves associating a DNA circle with the analyte and subsequent release and rolling circle replication of the circular DNA molecule. Thus, the disclosed method produces an amplified signal, via rolling circle amplification, from any analyte of interest. The amplification is isothermic and can result in the production of a large amount of nucleic acid from each primer.

The disclosed method is preferably used to detect and analyze proteins and peptides. In some embodiments, multiple proteins can be analyzed using solid supports, such as microtiter dishes, with which multiple different proteins or analytes are directly or indirectly associated (if they are present in the sample being tested). An amplification target circle is then associated with the various proteins using a conjugate of the circle and a specific binding molecule, such as an antibody, that is specific for the protein to be detected. Amplification target circles not associated with the proteins are removed, the amplification target circles that are associated with the proteins are decoupled from the specific binding molecule and replicated. Rolling circle replication primed by rolling circle replication primers results in production of a large amount of DNA. Use of exponential rolling circle amplification (ERCA), where the strand replicated from the amplification target circle is replicated using a second primer and both replicated strands generate further replicated strands, is preferred. Amplification products can be detected in real time using, for example, Amplifluor™ primers. The amplified DNA serves as a readily detectable signal for the proteins. Different proteins can be distinguished in several ways. For example, each different protein can be associated with a different amplification target circle which in turn is replicated to produce amplified DNA. The result is distinctive amplified DNA for each different protein. The different amplified DNAs can be distinguished using any suitable sequence-based nucleic acid detection technique. In this form of the method, many proteins can be detected in the same amplification reaction. Alternatively, the location of the amplified DNA on a solid support can indicate the protein involved if different proteins are immobilized at predetermined locations on the support.

Another embodiment of the disclosed method involves comparison of the proteins expressed in two or more different samples. The information generated is analogous to the type of information gathered in nucleic acid expression profiles. The disclosed method allows sensitive and accurate detection and quantitation of proteins expressed in any cell or tissue. The disclosed method also allows the same analyte(s) from different samples to be detected simultaneously in the same assay.

It is an object of the present invention to provide a method for detecting small quantities and concentrations of analytes.

It is a further object of the present invention to provide a method for detecting small quantities and concentrations of multiple analytes in samples.

It is a further object of the present invention to provide a method for amplifying the signal of an analyte to be detected.

It is a further object of the present invention to provide an automated method for detecting small quantities and concentrations of multiple analytes in samples.

It is a further object of the present invention to provide a method for profiling the presence of multiple analytes in a sample.

It is a further object of the present invention to provide a method for comparing profiles of the presence of multiple analytes in different samples.

It is a further object of the present invention to provide a method for assessing the interaction of compounds with molecules of interest.

It is a further object of the present invention to provide a method for detecting small quantities and concentrations of proteins and peptides.

It is a further object of the present invention to provide a method for detecting small quantities and concentrations of multiple proteins and peptides in samples.

It is a further object of the present invention to provide a method for amplifying the signal of a protein or peptide to be detected.

It is a further object of the present invention to provide an automated method for detecting small quantities and concentrations of multiple proteins and peptides in samples.

It is a further object of the present invention to provide a method for profiling the presence of multiple proteins and peptides in a sample.

It is a further object of the present invention to provide a method for comparing profiles of the presence of multiple proteins and peptides in different samples.

It is a further object of the present invention to provide a method for assessing the interaction of compounds with proteins and peptides of interest.

It is a further object of the present invention to provide compositions for detecting small quantities and concentrations of analytes.

It is a further object of the present invention to provide compositions for detecting small quantities and concentrations of proteins and peptides.

BRIEF DESCRIPTION OF THE DRAWINGS

In FIG. 1A, a reporter binding molecule (anti-human IgG with circle) is associated with a protein (HIV P24 protein) via an anti-HIV P24 antibody. The protein that is attached to Micro Amp tubes. The specific binding molecule of the reporter binding molecule is an anti-human IgG. In FIG. 1B, a reporter binding molecule (anti-biotin antibody with circle) is associated with a protein (HIV P24 protein) that is associated with an anti-HIV P24 antibody. The anti-HIV P24 antibodies are attached to Micro Amp tubes, thus associating the protein with the Micro Amp tubes. The specific binding molecule of the reporter binding molecule is an anti-biotin antibody. The amplification target circle of the reporter binding molecule is associated with the specific binding molecule via a circle capture probe.

DETAILED DESCRIPTION OF THE INVENTION

Figure 1A:
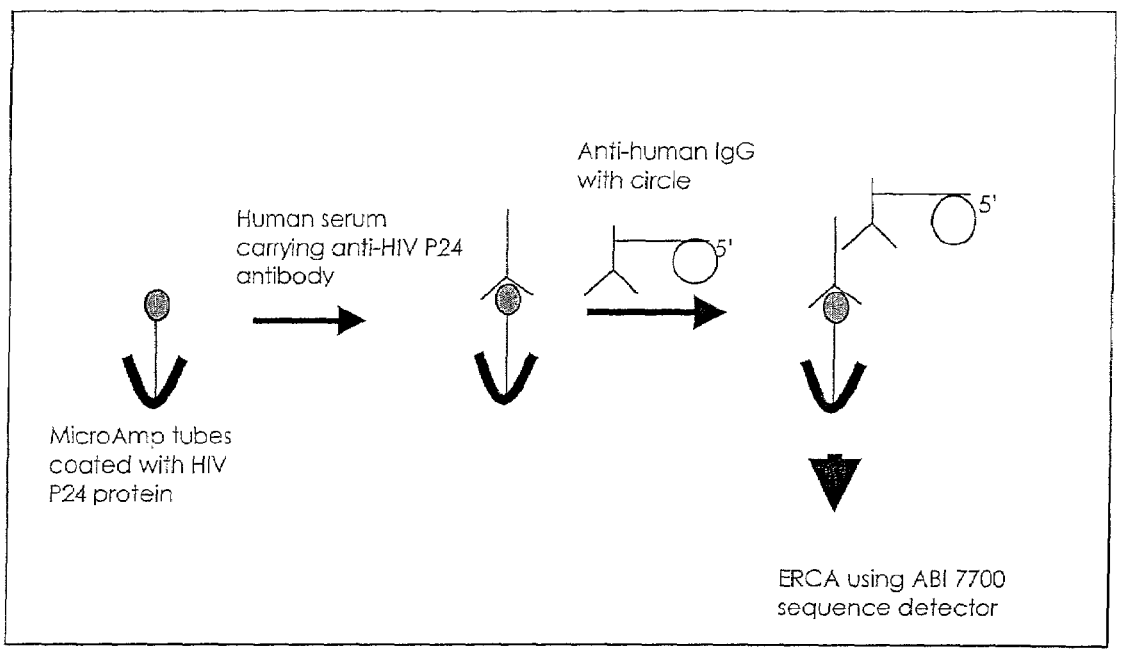
FIGS. 1A and 1B are diagrams of examples of two forms of the disclosed method.
Figure 1B:
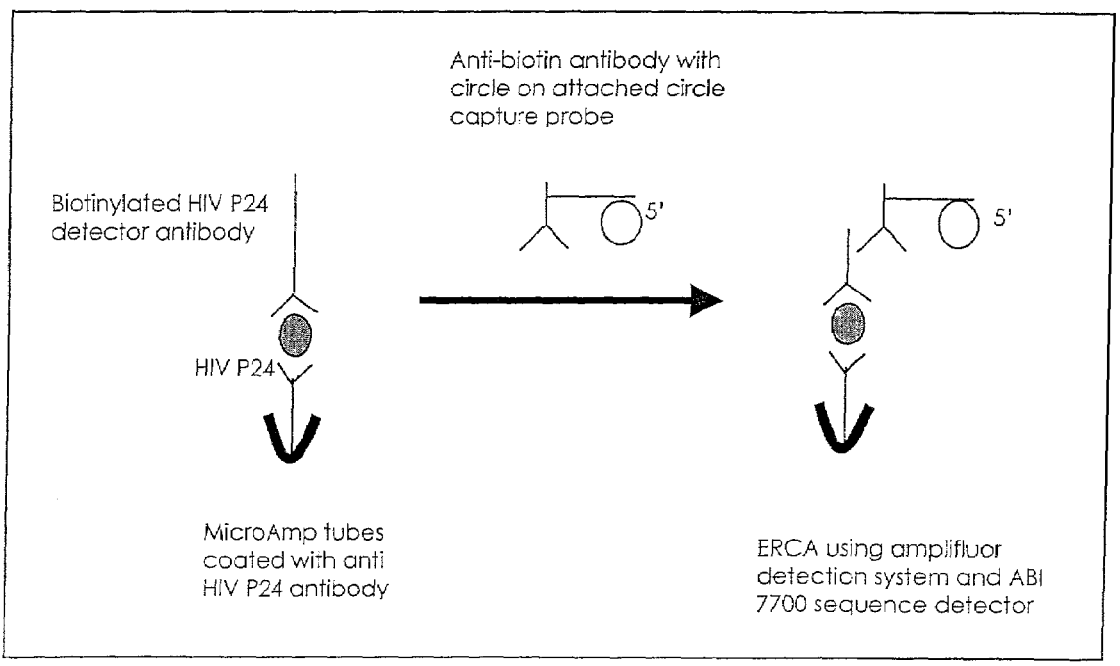

Disclosed are compositions and methods for detecting small quantities of analytes such as proteins and peptides. The method applies the power of nucleic acid signal amplification to the detection of non-nucleic acid analytes. Detection of such analytes—for which there are no amplification techniques comparable to nucleic acid amplification techniques—has generally depended on detection of sufficient quantities of the analyte or the use of extremely sensitive labels. The use of such labels is both cumbersome and limited. The disclosed method provides a simple and sensitive way to produce an amplified signal for any desired analyte.

The disclosed method is a form of rolling circle amplification (RCA) where a reporter binding molecule provides the amplification target circle for amplification. The disclosed method allows RCA to produce an amplified signal (that is, tandem sequence DNA (TS-DNA)) based on association of the reporter binding molecule with a target molecule (also referred to as an analyte). The specific amplification target circle that is a part of the reporter binding molecule provides the link between the specific interaction of the reporter binding molecule to an analyte (via the affinity portion of the reporter binding molecule) and RCA. Once the reporter binding molecule is associated with an analyte, a rolling circle replication primer is hybridized to the amplification target circle (ATC) of the reporter binding molecule, followed by amplification of the ATC by RCA (a secondary DNA strand displacement primer is also used if exponential RCA is performed). The disclosed method can be performed using any analyte. Preferred analytes are proteins, peptides, nucleic acids, including amplified nucleic acids such as TS-DNA and amplification target circles, antigens and ligands. Target molecules for the disclosed method are generally referred to herein as analytes.

The amplification target circle is released from the reporter binding molecule prior to or during amplification. Such release, referred to herein as decoupling, can be accomplished in any suitable manner. In general, the manner in which the amplification target circle is associated with, or linked or coupled to, the reporter binding molecule determines the form of decoupling. For example, where the amplification target circle is base paired to a circle capture probe in the reporter binding molecule, the amplification target circle can be decoupled from the reporter binding molecule by disrupting the base pairing. Where the amplification target circle is covalently coupled to the reporter binding molecule via circle linker having a cleavable bond, the amplification target circle can be decoupled from the reporter binding molecule by cleaving the cleavable bond. To identify analytes using the amplification target circles, reporter binding molecules that are not associated with analytes should be removed prior to decoupling.

Following decoupling, the amplification target circle can be replicated by rolling circle amplification. Exponential rolling circle amplification (ERCA) is the preferred form of RCA for this purpose. If multiple different analytes are to be detected, the amplification products of amplification target circles associated with different analytes should be distinguishable. This can be accomplished in any suitable manner. For example, the amplification target circles can be in separate locations prior to decoupling and remain separated following decoupling. The separate locations could be determined, for example, by the location of the analytes with which the amplification target circles are associated. In this case, some or all of the amplification target circles can be the same (thus producing the same amplification product). The different locations of the amplification products identifies the analyte involved. As another example, some or all of the amplification target circles that are associated with different analytes can be different (thus producing different amplification products). The different amplification products identify the analytes involved. Even if the amplification target circles are mixed together and/or amplified in the same reaction, the different amplification target circles (and thus the different corresponding analytes) can be detected and distinguished based on the differences in the amplification products.

The amplification products of RCA can be detected using any suitable technique. Real time detection, that is, detection during the RCA reaction is a preferred mode of detection with the disclosed method. Real time detection can be facilitated by use of Amplifluor™ primers. Amplifluor™ primers produce a fluorescent signal when they become incorporated into a replicated strand and are based paired with a complementary strand.

Although RCA reactions can be carried out with either linear or geometric kinetics (Lizardi et al., 1998), the disclosed method preferably uses geometric RCA. This latter form of RCA is referred to as exponential rolling circle amplification (ERCA). In exponential RCA, a secondary DNA strand displacement primer primes replication of TS-DNA to form a complementary strand referred to as secondary tandem sequence DNA or TS-DNA-2. As a secondary DNA strand displacement primer is elongated, the DNA polymerase will run into the 5' end of the next hybridized secondary DNA strand displacement molecule and will displace its 5' end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. A tertiary DNA strand displacement primer strand (which is complementary to the TS-DNA-2 strand and which can be the rolling circle replication primer) can then hybridize to, and prime replication of, TS-DNA-2 to form TS-DNA-3 (which is equivalent to the original TS-DNA). Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. The additional forms of tandem sequence DNA beyond secondary tandem sequence DNA are collectively referred to herein as higher order tandem sequence DNA. Higher order tandem sequence DNA encompasses TS-DNA-3, TS-DNA-4, and any other tandem sequence DNA produced from replication of secondary tandem sequence DNA or the products of such replication. In a preferred mode of ERCA, the rolling circle replication primer serves as the tertiary DNA strand displacement primer, thus eliminating the need for a separate primer.

The disclosed method is preferably used to detect and analyze proteins and peptides. In preferred embodiments, multiple proteins can be analyzed using solid supports to which the various proteins are immobilized (if they are present in the sample being tested). An amplification target circle is then associated with the various proteins using a conjugate of the circle and a specific binding molecule, such as an antibody, that is specific for the protein to be detected. Rolling circle replication of the amplification target circles results in production of a large amount of DNA. The amplified DNA serves as a readily detectable signal for the proteins. Different proteins can be distinguished in several ways. For example, each different protein can be associated with a different amplification target circle that in turn is replicated to produce amplified DNA. The result is distinctive amplified DNA for each different protein. The different amplified DNAs can be distinguished using any suitable sequence-based nucleic acid detection technique. In this form of the method, many proteins can be detected in the same amplification reaction. Different amplification target circles associated with different proteins produce distinguishable amplified DNA which identifies the corresponding proteins (that is, the proteins with which the reporter binding molecules had been associated). Alternatively, the location of the amplified DNA can indicate the protein involved if different proteins are immobilized at predetermined locations on a solid support.

Another embodiment of the disclosed method involves comparison of the proteins expressed in two or more different samples. The information generated is analogous to the type of information gathered in nucleic acid expression profiles. For example, the same analyte(s) from different samples can be associated with different amplification target circles which are replicated to produce different amplified DNAs. In this way, an analyte from one sample will produce a different amplified DNA from the same analyte in a different sample. This sample-specific detection can be achieved even when the samples are mixed together following association of the amplification target circles with the analytes (a preferred mode of the method). For example, different analyte capture agents can be mixed with first and second samples, respectively. This associates a different hapten with the same type of analyte in the different samples. In preferred embodiments, the samples are mixed together. The analytes can be captured on substrate, reporter binding molecules can be associated with the analyte capture agents, and DNA from the amplification target circles. Even if analytes from different samples are captured at the same location on the substrate (a preferred mode of the method), the source and amount of each analyte present at that location can be determined by virtue of the different amplified DNAs that will be produced.

The source of an analyte (that is, the sample from which the analyte came) can be determined, for example, by using different labels for different amplified DNAs (which resulted from amplification target circles keyed to the different samples). By using labels that can be distinguished when detected simultaneously with other labels (such as fluorescent labels with distinct emission spectra), all of the samples can be mixed together and analyzed together. The detected label identifies the source of the analyte indirectly through the chain of components: label to amplified DNA to circular DNA to analyte.

In another form of the disclosed method, referred to as ImmunoRCA, the amplification target circle is attached to an antibody. In one preferred form of the disclosed method, the antibody is directed against a hapten. In another preferred form of the disclosed method, the antibody is directed against the analyte itself. In the presence of a primer (referred to as a rolling circle replication primer), DNA polymerase, and nucleotides, the rolling circle reaction results in a DNA molecule consisting of multiple copies of the circle DNA sequence (referred to as tandem sequence DNA). A secondary DNA strand displacement primer is also used if exponential RCA is performed. The amplified DNA can be detected in a variety of ways, including direct incorporation of hapten- or fluorescently-labeled nucleotides, or by hybridization of fluor or enzymatically labeled complementary oligonucleotide probes.

In another aspect, the disclosed method involves immobilization of analytes present in complex biological samples and determining and quantitating their presence in the samples. For example, antigens present in biological extracts and fluids can be identified by first selectively immobilizing them on solid supports. An immunoRCA assay can then be employed for detection and quantitation.

In another aspect, the disclosed method involves multiplexed detection and quantitation of more than one analyte in a sample. For example, a solid support can be incubated with sample containing a mixture of protein analytes to be detected, where the solid support contains immobilized capture antibodies (analyte capture agents). The solid support next can be incubated with a mixture containing at least one biotinylated antibody for each analyte. An immunoRCA microarray assay then can be employed for detection and quantitation.

In another aspect, an immunoRCA assay can be performed in microwell-glass slides, where each well is separated by a Teflon mask, or microtiter dishes. Each of the wells can be used to assay different analytes and/or different samples, and controls. Multiwell slides also can be printed with arrays of anti-IgE capture antibodies in the wells. Semi-automation of immunoRCA assays in such multiwell formats can be implemented, for example, on inexpensive liquid handling robots.

ImmunoRCA assay can be applied to other multiplexed antibody assays. For example, certain immunological reactions are caused by specific $IgG_4$ rather than IgE (AAAI Board of Directors, *J Allergy Clin Immunol.* 95:652-654 (1995)). The use of an anti-human $IgG_4$ conjugated to a DNA circle that is different in sequence from the DNA circle conjugated to an anti-IgE would allow the simultaneous measurement of allergen-specific $IgG_4$ and IgE. Such an assay can be used during allergen desensitisation therapy or for monitoring response to anti-IgE therapy (Chang *Nature Biotech.* 18:157-162 (2000)).

The enormous multiplexing capabilities of immunoRCA, such as the ability to detect and differentiate multiple analytes based on the sequence of amplified DNA, can be used for clinical diagnostic tests involving detection of multiple specific antibodies, such as autoantibodies in suspected systemic autoimmune disorders, inflammatory arthritis, organ-specific autoimmune disorders or, indeed, in histocompatibility testing. Additional applications include infectious disease diagnostics with measurement of strain- and species-specific IgM and IgG, as well as in vitro testing of functional antibody responses in patients with suspected primary and secondary immunodeficiency diseases. Finally, the multiplexing, automation and ultrasensitivity of this format can be applied to other immunoassays besides those involving antibody detection. RCA-powered sandwich immunoassays can provide a 8- to 9-log gain in sensitivity (signal) over conventional assays for analytes such as prostate serum antigen. Thus, the disclosed method produces a huge gain in diagnostic and prognostic power made possible by the simultaneous testing of multiple analytes for the molecular staging of disease.

Nucleic acids are ideal molecular labels for multiple analyte detection because different specific sequences can be arbitrarily associated with each individual analyte. Direct covalent coupling of nucleic acid (as a circle capture probe) to antibody permits an unlimited number of antibody-nucleic acid adducts to be prepared and used in any combination, provided that each nucleic acid is unique (Hendrickson et al., *Nucleic Acids Res.* 23: 522-529 (1995)).

Materials

A. Analytes

The disclosed method involves the detection of analytes. In general, any compound, moiety, or component of a compound or complex can be an analyte. Preferred analytes are peptides, proteins, and other macromolecules such as lipids, complex carbohydrates, proteolipids, membrane fragments, and nucleic acids. Analytes can also be smaller molecules such as cofactors, metabolites, enzyme substrates, metal ions, and metal chelates. Analytes preferably range in size from 100 daltons to 1,000,000 daltons.

Analytes may contain modifications, both naturally occurring or induced in vitro or in vivo. Induced modifications include adduct formation such as hapten attachment, multimerization, complex formation by interaction with other chemical moieties, digestion or cleavage (by, for example, protease), and metal ion attachment or removal. The disclosed method can be used to detect differences in the modification state of an analyte, such as the phosphorylation or glycosylation state of proteins.

Analytes can be associated directly or indirectly with substrates (solid supports), preferably solid supports with multiple reaction chamers. Most preferred are microtiter dishes. Analytes can be captured and/or immobilized using analyte capture agents. Immobilized analytes can be used to capture other components used in the disclosed method such as analyte capture agents and reporter binding molecules.

B. Reporter Binding Molecules

A reporter binding molecule comprises a specific binding molecule coupled or tethered to, or associated with, an amplification target circle. A reporter binding molecule can also comprise a circle capture probe, a circle linker, or both. The specific binding molecule is referred to as the affinity portion of the reporter binding molecule and the amplification target circle is referred to as the nucleic acid portion of the reporter binding molecule. The sequence of the amplification target circle sequence can be arbitrarily chosen. In a multiplex assay using multiple reporter binding molecules, it is preferred that the amplification target circle sequence for each reporter binding molecule be substantially different to limit the possibility of non-specific target detection. Alternatively, it may be desirable in some multiplex assays, to use amplification target circle sequences with related sequences. Such assays can use one or a few ATCs to detect a larger number of analytes.

Amplification target circles can be coupled or tethered to, or associated with, a specific binding molecules in any manner that allows release (decoupling) of the amplification target circles from the reporter binding molecules. For example, the amplification target circle can be base paired to a circle capture probe in the reporter binding molecule or covalently coupled to the reporter binding molecule via circle linker having a cleavable bond. As used herein, decoupling refers to physical disunion of one molecule or component from another (as for example, decoupling of an amplification target circle from a reporter binding molecule). It is specifically contemplated that decoupling refers to the physical disunion both of molecules or components that are covalent couple to each other and molecules or components that are non-covalently associated with each other. In the former case, decoupling will generally involve cleavage of one of more covalent bonds. In the latter case, decoupling will generally involve dissociation. In the case of an amplification target molecule that is tethered to a specific binding molecule, decoupling can involve dissociation, cleavage of one or more covalent bonds, or both.

A circle capture probe is an oligomer, such as an oligonucleotide, that can base pair with an amplification target circle. The region of the circle capture probe that base pairs with the amplification target circle can be any length that supports specific and stable hybridization between the circle capture probe and the amplification target circle. Generally this is 12 to 100 nucleotides long, but is preferably 20 to 45 nucleotides long. The amplification target circle can be decoupled from the reporter binding molecule by disrupting the base pairing. In general, the circle capture probe should be incapable of priming nucleic acid synthesis. This can be accomplished in any suitable manner. For example, the circle capture probe can be coupled to the specific binding molecule via the 3' end of the circle capture probe, thus making it unavailable for extension. The 3' end of the circle capture probe can also be blocked to prevent extension. This can be accomplished by, for example, modification of the 3' end nucleotide. For example, a chemical group or molecule can be added to the 3' end. The circle capture probe can also be composed of subunits that do not support priming.

A circle linker is a component of a reporter molecule that links the amplification target circle to the specific binding molecule in a reporter binding molecule. Circle linkers preferably have a cleavable bond. As used herein, a cleavable bond is a covalent bond that can be easily and/or specifically cleaved. A cleavable bond in a circle linker is used to decouple the amplification target molecule from the reporter binding molecule. The amplification target circle can be decoupled from the reporter binding molecule by cleaving the cleavable bond.

Examples of useful circle linkers include linkers comprising a disulfide bond or a dihydroxy bond. Useful examples of linkers comprising disulfide bonds include dithiobis succinimidyl propionate, dimethyl 3,3'-dithiobispropionimidate, dithio-bis-maleimidoethane, 3,3'-dithiobis sulfosuccinimidyl propionate, succinimidyl 6-[3-(2pyridyldithio)-propionamido]hexonate, or N-succinimidyl 3-[2-pyridyldithio] propionate. Useful examples of linkers comprising dihydroxy bonds include 1,4 bis-maleimidyl-2,3-dihydroxybutane, disuccinimidyl tartrate, or disulfosuccinimidyl tartrate. Disulfide bonds can be cleaved by, for example, treatment with a reducing agent such as β-mercaptoethanol or dithiothreitol. Dihydroxy bonds can be cleaved by, for example, treatment with periodate. Circle linkers can be attached to amplification target circles via a reactive group on the amplification target circle. Numerous reactive groups are known and can be used for this purpose. For example, the reactive group can be an allyl amino group.

Figure 3:
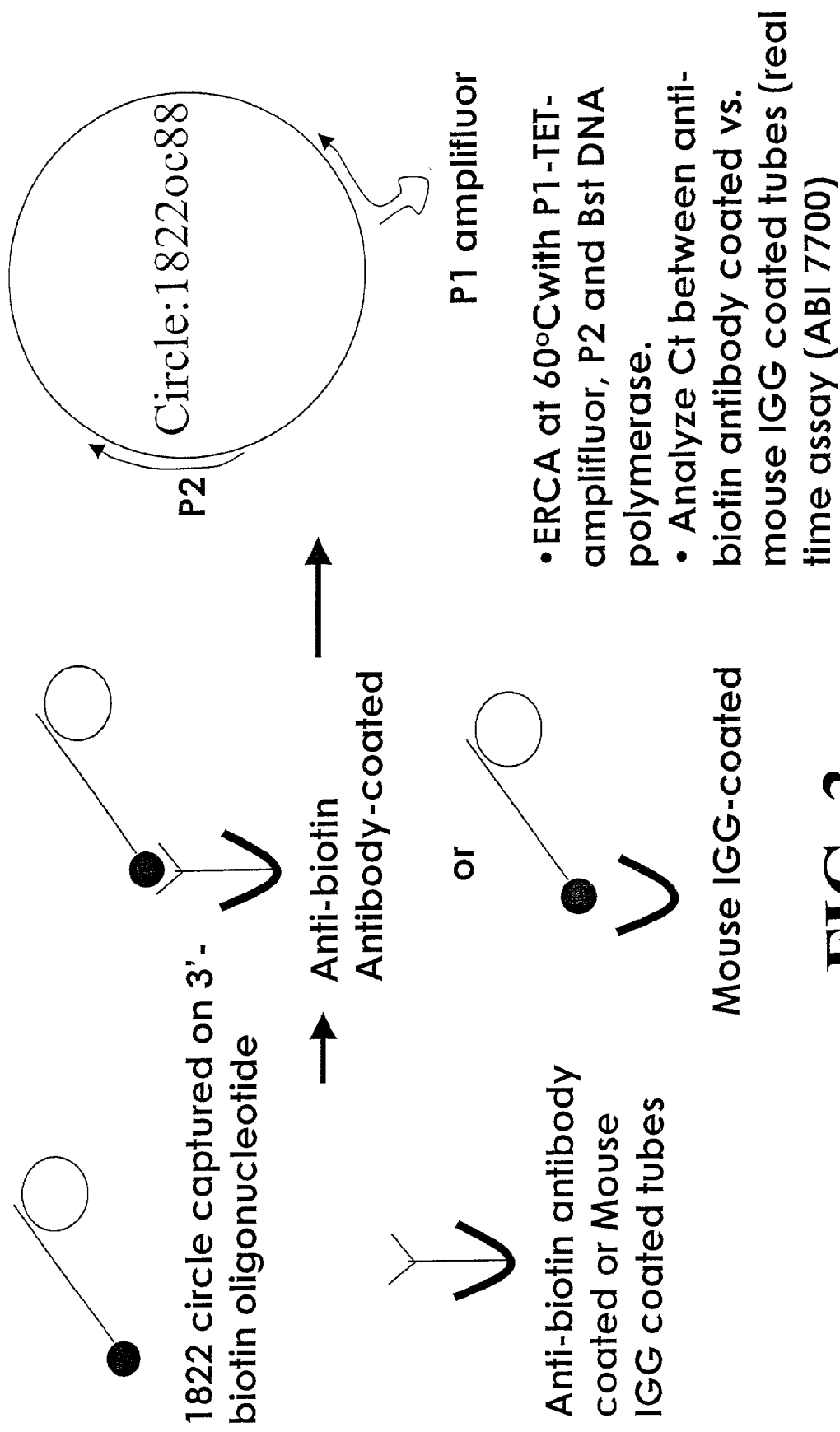
FIG. 3 is a diagram of a comparison of association of reporter binding molecules to cognate and non-cognate analytes. The "analytes" are anti-biotin antibodies (cognate) and mouse IgG (non-cognate). The non-cognate analyte serves as a control. The reporter binding molecules consists of biotin (the specific binding molecule), an oligonucleotide (the circle capture probe), and an 1822 circle (the amplification target circle) which is complementary to the oligonucleotide. The reporter binding molecule interacts only with the anti-biotin antibodies. Decoupled amplification target circles are amplified by ERCA using an Amplifluor™ primer (P1), a secondary DNA strand displacement primer (P2), and Bst DNA polymerase.
Figure 5:
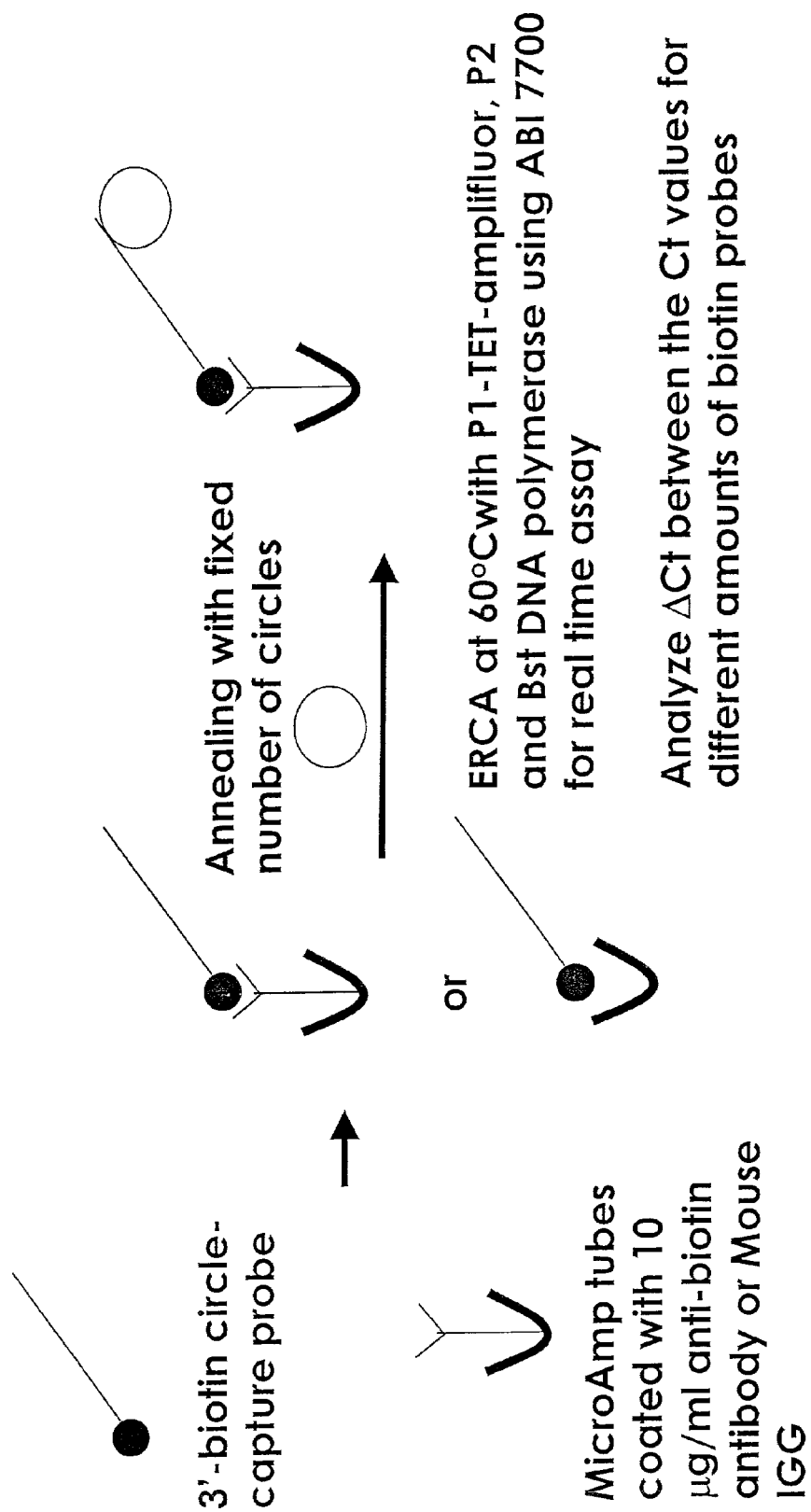
FIG. 5 is a diagram of a comparison of association of partial reporter binding molecules to cognate and non-cognate analytes. The "analytes" are anti-biotin antibodies (cognate) and mouse IgG (non-cognate). The non-cognate analyte serves as a control. The partial reporter binding molecules consists of biotin (the specific binding molecule), and an oligonucleotide (the circle capture probe). The partial reporter binding molecule interacts only with the anti-biotin antibodies. The amplification target circles, which are complementary to the oligonucleotide, are annealed to the circle capture probe after the partial reporter binding molecule is associated with the analyte. Decoupled amplification target circles are amplified by ERCA using an Amplifluor™ primer (P1), a secondary DNA strand displacement primer (P2), and Bst DNA polymerase.

Amplification target circles can be associated with or linked to specific binding molecules to form reporter binding agents before, during, or after association of the specific binding molecule with an analyte. For example, where a specific binding molecule is coupled to a circle capture probe, the amplification target circle can be base paired with the circle capture probe after the specific binding molecule is associated with the analyte. This is illustrated in FIG. 5 and Example 3. Alternatively, the amplification target circle is base paired with the circle capture probe before the specific binding molecule is associated with the analyte. This is illustrated in FIG. 3 and Example 2.

Generally, an amplification target circle will be linked to a specific binding molecule through covalent coupling. That is, the specific binding molecule is covalently coupled to the circle linker, and the circle linker is covalently coupled to the amplification target circle. However, amplification target circles can also be linked to a specific binding molecule by tethering. In such a case the circle linker is the tether and is referred to as a tether circle linker. An amplification target circle is tethered to a specific binding molecule when circle linker is looped through the amplification target circle and where both sides of the circle linker (preferably both ends) are covalently coupled to the specific binding molecule. Topologically, the amplification target circle can rotate through the looped circle linker. The tether circle linker can be any material that can form a loop and be coupled to a specific binding molecule. Linear polymers are a preferred material for tether circle linkers. When the cleavable bond in the circle linker is cleaved, the tether is broken and the amplification target circle is decoupled from the reporter binding molecule.

As used herein, a specific binding molecule is a molecule that interacts specifically with a particular molecule or moiety. The molecule or moiety that interacts specifically with a specific binding molecule can be an analyte or another molecule that serves as an intermediate in the interaction between the specific binding molecule and the analyte. A preferred example of such an intermediate is an analyte capture agent. It is to be understood that the term analyte refers to both separate molecules and to portions of molecules, such as an epitope of a protein, that interacts specifically with a specific binding molecule. Antibodies, either member of a receptor/ligand pair, and other molecules with specific binding affinities are examples of specific binding molecules, useful as the affinity portion of a reporter binding molecule. A reporter binding molecule with an affinity portion that is an antibody is also referred to herein as a reporter antibody. By coupling an amplification target circle to such specific binding molecules, binding of a specific binding molecule to its specific target can be detected by amplifying an ATC with rolling circle amplification. This amplification allows sensitive detection of a very small number of bound analytes.

A reporter binding molecule that interacts specifically with a particular analyte is said to be specific for that analyte. For example, a reporter binding molecule with an affinity portion that is an antibody that binds to a particular antigen is said to be specific for that antigen. The antigen is the analyte.

Antibodies useful as the affinity portion of reporter binding molecules, can be obtained commercially or produced using well established methods. For example, Johnstone and Thorpe, on pages 30-85, describe general methods useful for producing both polyclonal and monoclonal antibodies. The entire book describes many general techniques and principles for the use of antibodies in assay systems.

In use, the reporter binding molecules need not be absolutely pure. The reporter binding molecules preferably are at least 20% pure, more preferably at least 50% pure, more preferably at least 80% pure, and more preferably at least 90% pure.

C. Amplification Target Circles

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an amplification target circle. Detection tag portions, secondary target sequence portions, address tag portions, and promoter portions are optional. Generally, an amplification target circle is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and, if present on the amplification target circle, the detection tag portions, the secondary target sequence portions, the address tag portions, and the promoter portion. These sequences in the TS-DNA are referred to as primer sequences (which match the sequence of the rolling circle replication primer), spacer sequences (complementary to the spacer region), detection tags, secondary target sequences, address tags, and promoter sequences. Amplification target circles are useful as components of reporter binding molecules.

D. Rolling Circle Replication Primer

A rolling circle replication primer (RCRP) is an oligonucleotide having sequence complementary to the primer complement portion of an ATC. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the ATC. The complementary portion of a rolling circle replication primer can be any length that supports specific and stable hybridization between the primer and the primer complement portion. Generally this is 12 to 100 nucleotides long, but is preferably 20 to 45 nucleotides long.

It is preferred that rolling circle replication primers also contain additional sequence at the 5' end of the RCRP that is not complementary to any part of the ATC. This sequence is referred to as the non-complementary portion of the RCRP. The non-complementary portion of the RCRP, if present, serves to facilitate strand displacement during DNA replication. The non-complementary portion of a RCRP may be any length, but is generally 1 to 100 nucleotides long, and preferably 4 to 8 nucleotides long. A rolling circle replication primer can be used as the tertiary DNA strand displacement primer in exponential rolling circle amplification. For exponential rolling circle amplification, the sequence of the rolling circle replication primer can be chosen such that it is not significantly complementary to the sequence of the secondary DNA strand displacement primer.

In preferred embodiments, rolling circle replication primers (and other primers used in the method) can contain a spacer. The spacer can help to overcome steric factors from the surface when immobilized, aid in anchoring polymerase on primers, or provide other advantages, such as control or alteration of the hydrophobicity of elements attached to a solid support. Spacers useful for the disclosed method include nucleotide spacers such as poly dT or poly dA; aliphatic linkers such as C18, C12, or multimers thereof; aromatic spacers, or RNA, DNA, PNA or combinations thereof.

Rolling circle replication primers are preferably Amplifluor™ primers. Amplifluors™ are fluorescent moieties and quenchers incorporated into primers containing stem structures (usually in hairpin or stem and loop structures) such that the quencher moiety is in proximity with the fluorescent moiety. That is, the quencher and fluorescent are incorporated into opposite strands of the stem structure. In the structured state, the quencher prevents or limits fluorescence of the fluorescent moiety. When the stem of the primer is disrupted, the quencher and fluorescent moiety are no longer in proximity and the fluorescent moiety produces a fluorescent signal. In the disclosed method, use of Amplifluor™ primers in ERCA produces double stranded tandem sequence DNA where the primer stem is disrupted in favor of a complementary, replicated strand. From a reaction initially containing structured (that is, non-fluorescent) Amplifluor™ primers, fluorescence signal increases as amplification takes place, as more and more of the Amplifluor™ primers are incorporated into double stranded TS-DNA, as the Amplifluor™ stems are disrupted, and as the fluorescent moieties as consequently unquenched. Thus, use of Amplifluor™ primers is particularly suited for real-time detection of amplification in ERCA. Amplifluor™ primers are also referred to herein as fluorescent quenched primers. Thus, an Amplifluor™ rolling circle replication primer is also referred to as a fluorescent quenched rolling circle replication primer.

E. Analyte Capture Agents

An analyte capture agent is any compound that can interact with an analyte and allow the analyte to be immobilized or separated from other compounds and analytes. An analyte capture agent includes an analyte interaction portion. Analyte capture agents can also include a capture portion. Analyte capture agents without a capture portion preferably are immobilized on a solid support. The analyte interaction portion of an analyte capture agent is a molecule that interacts specifically with a particular molecule or moiety. The molecule or moiety that interacts specifically with an analyte interaction portion can be an analyte or another molecule that serves as an intermediate in the interaction between the analyte interaction portion and the analyte. It is to be understood that the term analyte refers to both separate molecules and to portions of molecules, such as an epitope of a protein, that interacts specifically with an analyte interaction portion. Antibodies, either member of a receptor/ligand pair, and other molecules with specific binding affinities are examples of molecules that can be used as an analyte interaction portion of an analyte capture agent. The analyte interaction portion of an analyte capture agent can also be any compound or composition with which an analyte can interact, such as peptides. An analyte capture agent that interacts specifically with a particular analyte is said to be specific for that analyte. For example, an analyte capture agent with an analyte interaction portion that is an antibody that binds to a particular antigen is said to be specific for that antigen. The antigen is the analyte.

Examples of molecules useful as the analyte interaction portion of analyte capture agents are antibodies, such as crude (serum) antibodies, purified antibodies, monoclonal antibodies, polyclonal antibodies, synthetic antibodies, antibody fragments (for example, Fab fragments); antibody interacting agents, such as protein A, carbohydrate binding proteins, and other interactants; protein interactants (for example avidin and its derivatives); peptides; and small chemical entities, such as enzyme substrates, cofactors, metal ions/chelates, and haptens. Antibodies may be modified or chemically treated to optimize binding to surfaces and/or targets.

Antibodies useful as the analyte interaction portion of analyte capture agents, can be obtained commercially or produced using well-established methods. For example, Johnstone and Thorpe, on pages 30-85, describe general methods useful for producing both polyclonal and monoclonal antibodies. The entire book describes many general techniques and principles for the use of antibodies in assay systems.

The capture portion of an analyte capture agent is any compound that can be associated with another compound. Preferably, a capture portion is a compound, such as a ligand or hapten, that binds to or interacts with another compound, such as ligand-binding molecule or an antibody. It is also preferred that such interaction between the capture portion and the capturing component be a specific interaction, such as between a hapten and an antibody or a ligand and a ligand-binding molecule. Examples of haptens include biotin, FITC, digoxigenin, and dinitrophenol. The capture portion can be used to separate compounds or complexes associated with the analyte capture agent from those that do not.

Capturing analytes or analyte capture agents on a substrate may be accomplished in several ways. In one embodiment, capture docks are adhered or coupled to the substrate. Capture docks are compounds or moieties that mediate adherence of an analyte by binding to, or interacting with, the capture portion on an analyte capture agent (with which the analyte is, or will be, associated). Capture docks immobilized on a substrate allow capture of the analyte on the substrate. Such capture provides a convenient means of washing away reaction components that might interfere with subsequent steps. Alternatively, analyte capture agents can be directly immobilized on a substrate. In this case, the analyte capture agent need not have a capture portion.

In one embodiment, the analyte capture agent or capture dock to be immobilized is an anti-hybrid antibody. Methods for immobilizing antibodies and other proteins to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is a heterobifunctional cross-linking agent such as N-[γ-maleimidobutyryloxy]succinimide ester (GMBS). These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209-216 and 241-242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino, carboxyl, or sulfur groups using glutaraldehyde, carbodiimides, or heterobifunctional agents such as GMBS as cross-linkers. In this method, aqueous solutions containing free antibodies are incubated with the solid support in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

One useful form of analyte capture agents are peptides. When various peptides are immobilized on a solid support, they can be used as "bait" for analytes. For example, a set of different peptides on a solid support can be used to access whether a sample has analytes that interact with any of the peptides. Comparisons of different samples can be made by, for example, noting differences in the peptides to which analytes in the different samples become associated. In another form of the disclosed method, a set of analyte capture agents specific for analytes of interest can be used to access the presence of a whole suite of analytes in a sample.

In use, the analyte capture agents need not be absolutely pure. The analyte capture agents preferably are at least 20% pure, more preferably at least 50% pure, more preferably at least 80% pure, and more preferably at least 90% pure.

F. Accessory Molecules

Accessory molecules are molecules that affect the interaction of analytes and specific binding molecules or analyte capture agents. For example, accessory molecules can be molecules that compete with the binding of an analyte with an analyte capture agent or specific binding molecule. One form of competitive accessory molecules are analogs of analytes. An analog is a molecule that is similar in structure but different in competition. In this context, the analyte analog should be sufficiently similar to interact with an analyte capture agent or specific binding molecule specific for that analyte. Accessory molecules can also be molecules that aid or are necessary for interaction of an analyte and a specific binding molecule or analyte capture agent. Such accessory molecules are referred to herein as analyte binding co-factors.

In one form of the disclosed method, accessory molecules can be compounds that are to be tested for their effect on analyte binding. For example, the disclosed method can be used to screen for competitors (or binding co-factors) of an analyte interaction with a specific binding molecule or analyte capture agent. If an accessory molecule affects interaction of the analyte, the results of RCA will change since the association of the reporter binding molecule to the analyte (or of the analyte capture agent to the analyte) will be lost or gained.

In use, the accessory molecules need not be absolutely pure. The accessory molecules preferably are at least 20% pure, more preferably at least 50% pure, more preferably at least 80% pure, and more preferably at least 90% pure.

G. Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—$CH_3$, Diamino Phenyl Oxydiazole (DAO), Dimethylamino-5-Sulphonic acid, Dipyrromethene boron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 mu; 778 nm), thus allowing their simultaneous detection. Other examples of fluorescein dyes include 6-carboxyfluorescein (6-FAM), 2',4',1,4,-tetrachlorofluorescein (TET), 2',4',5',7',1, 4-hexachlorofluorescein (HEX), 2',7'dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule. Such labels include "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

Another useful label, related to molecular beacon technology, are Amplifluors™. Amplifluors™ are fluorescent moieties and quenchers incorporated into primers containing stem structures (usually in hairpin or stem and loop structures) such that the quencher moiety is in proximity with the fluorescent moiety. That is, the quencher and fluorescent are incorporated into opposite strands of the stem structure. In the structured state, the quencher prevents or limits fluorescence of the fluorescent moiety. When the stem of the primer is disrupted, the quencher and fluorescent moiety are no longer in proximity and the fluorescent moiety produces a fluorescent signal. In the disclosed method, use of Amplifluor™ primers in ERCA produces double stranded tandem sequence DNA where the primer stem is disrupted in favor of a complementary, replicated strand. From a reaction initially containing structured (that is, non-fluorescent) Amplifluor™ primers, fluorescence signal increases as amplification takes place, as more and more of the Amplifluor™ primers are incorporated into double stranded TS-DNA, as the Amplifluor™ stems are disrupted, and as the fluorescent moieties as consequently unquenched. Thus, use of Amplifluor™ is particularly suited for real-time detection of amplification in ERCA.

Labeled nucleotides are a preferred form of detection label since they can be directly incorporated into the amplification products during synthesis. Examples of detection labels that can be incorporated into amplified nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951:157-165 (1988)), bromouridine (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226-3232 (1994 )). A preferred nucleotide analog detection label for DNA is BrdUrd (bromodeoxyuridine, BrdUrd, BrdU, BUdR, Sigma-Aldrich Co). Other useful nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A preferred nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Detection labels that are incorporated into amplified nucleic acid, such as biotin, can be subsequently detected using sensitive methods known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

H. Detection Probes

Detection probes are labeled oligonucleotides having sequence complementary to detection tags on TS-DNA. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnology* 14:303-308 (1996)). The use of such probes eliminates the need for removal of unhybridized probes prior to label detection because the unhybridized detection probes will not produce a signal. This is especially useful in multiplex assays. The TS-DNA can be collapsed as described in WO 97/19193 using collapsing detection probes. Collapsing TS-DNA is especially useful with combinatorial multicolor coding, which is described below.

I. DNA Strand Displacement Primers

Primers used for secondary DNA strand displacement (an example of which is exponential rolling circle amplification) are referred to herein as DNA strand displacement primers. One form of DNA strand displacement primer, referred to herein as a secondary DNA strand displacement primer, is an oligonucleotide having sequence matching part of the sequence of an ATC. This sequence is referred to as the matching portion of the secondary DNA strand displacement primer. This matching portion of a secondary DNA strand displacement primer is complementary to sequences in TS-DNA. The matching portion of a secondary DNA strand displacement primer may be complementary to any sequence in TS-DNA. The matching portion of a secondary DNA strand displacement primer can be any length that supports specific and stable hybridization between the primer and its complement. Generally this is 12 to 35 nucleotides long, but is preferably 18 to 25 nucleotides long. In general, the sequence of a secondary DNA strand displacement primer should be chosen such that it is not significantly complementary to the sequence of the rolling circle replication primer with which it is used. Secondary DNA strand displacement primers are used with tertiary strand displacement primers in exponential rolling circle amplification. In general, the sequence of a secondary DNA strand displacement primer should be chosen such that it is not significantly complementary to the sequence of the tertiary DNA strand displacement primer with which it is used.

Another form of DNA strand displacement primer, referred to herein as a tertiary DNA strand displacement primer, is an oligonucleotide having sequence complementary to part of the sequence of an ATC. This sequence is referred to as the complementary portion of the tertiary DNA strand displacement primer. This complementary portion of the tertiary DNA strand displacement primer matches sequences in TS-DNA. The complementary portion of a tertiary DNA strand displacement primer may be complementary to any sequence in the ATC. The complementary portion of a tertiary DNA strand displacement primer can be any length that supports specific and stable hybridization between the primer and its complement. Generally this is 12 to 35 nucleotides long, but is preferably 18 to 25 nucleotides long. In general, the sequence of a tertiary DNA strand displacement primer should be chosen such that it is not significantly complementary to the sequence of the secondary DNA strand displacement primer with which it is used. A preferred tertiary DNA strand displacement primer is a rolling circle replication primer. In this case, the sequence of the rolling circle replication primer should be chosen such that it is not significantly complementary to the sequence of the secondary DNA strand displacement primer with which it is used. DNA strand displacement primers and their use are described in more detail in U.S. Pat. No. 5,854,033 and WO 97/19193.

DNA strand displacement primers preferably are Amplifluor™ primers. In the disclosed method, use of Amplifluor™ primers in ERCA produces double stranded tandem sequence DNA where the primer stem is disrupted in favor of a complementary, replicated strand. From a reaction initially containing structured (that is, non-fluorescent) Amplifluor™ primers, fluorescence signal increases as amplification takes place, as more and more of the Amplifluor™ primers are incorporated into double stranded TS-DNA, as the Amplifluor™ stems are disrupted, and as the fluorescent moieties as consequently unquenched. Thus, use of Amplifluors™ is particularly suited for real-time detection of amplification in ERCA. If Amplifluor™ primers are used, only one of the primers in a RCA reaction need be an Amplifluor™ primer. However, any or all of the primers used can be Amplifluor™ primers, and any combination of Amplifluor™ and non-Amplifluor™ primers can be used. For example, the rolling circle replication primer can be non-Amplifluor™ while the secondary DNA strand displacement primer can be Amplifluor™, or the rolling circle replication primers can be a mixture of Amplifluor™ and non-Amplifluor™ primers. Amplifluor™ primers are also referred to herein as fluorescent quenched primers. Thus, an Amplifluor™ DNA strand displacement primer is also referred to as a fluorescent quenched DNA strand displacement primer.

J. Oligonucleotide Synthesis

Rolling circle replication primers, circle capture probes, circle linkers, detection probes, address probes, amplification target circles, DNA strand displacement primers, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989 ) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et a. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253-1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291-3296) or the phosphotriester method as described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994). Other forms of oligonucleotide synthesis are described in U.S. Pat. No. 6,294,664 and U.S. Pat. No. 6,291,669.

Many of the oligonucleotides described herein are designed to be complementary to certain portions of other oligonucleotides or nucleic acids such that stable hybrids can be formed between them via base pairing. The stability of these hybrids can be calculated using known methods such as those described in Lesnick and Freier, *Biochemistry* 34:10807-10815 (1995), McGraw et al., *Biotechniques* 8:674-678 (1990), and Rychlik et al., *Nucleic Acids Res.* 18:6409-6412 (1990).

Oligonucleotides can be synthesized, for example, on a Perseptive Biosystems 8909 Expedite Nucleic Acid Synthesis system using standard β-cyanoethyl phosphoramidite coupling chemistry on synthesis columns (Glen Research, Sterling, Va.). Oxidation of the newly formed phosphites can be carried out using, for example, the sulfurizing reagent 3H-1,2-benzothiole-3-one-1,1-idoxide (Glen Research) or the standard oxidizing reagent after the first and second phosphoramidite addition steps. The thio-phosphitylated oligonucleotides can be deprotected, for example, using 30% ammonium hydroxide (3.0 ml) in water at 55° C. for 16 hours, concentrated in an OP 120 Savant Oligo Prep deprotection unit for 2 hours, and desalted with PD10 Sephadex columns using the protocol provided by the manufacturer.

So long as their relevant function is maintained, rolling circle replication primers, circle capture probes, circle linkers, detection probes, address probes, amplification target circles, DNA strand displacement primers, and any other oligonucleotides can be made up of or include modified nucleotides (nucleotide analogs). Many modified nucleotides are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases.

Universal bases include 3-nitropyrrole and 5-nitroindole. Universal bases substitute for the normal bases but have no bias in base pairing. That is, universal bases can base pair with any other base. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH$_2$)n O]m CH$_3$, —O(CH$_2$)n OCH$_3$, —O(CH$_2$)n NH$_2$, —O(CH$_2$)n CH$_3$, —O(CH$_2$)n —ONH$_2$, and —O(CH$_2$)nON[(CH$_2$)n CH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981, 957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to (base pair to) complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185, 444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science 254:1497-1500 (1991)).

Oligonucleotides can be comprised of nucleotides and can be made up of different types of nucleotides or the same type of nucleotides. For example, one or more of the nucleotides in an oligonucleotide can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides.

K. Solid Supports

Solid supports are solid-state substrates or supports with which analytes (or other components used in the disclosed method) can be associated. Analytes can be associated with solid supports directly or indirectly. For example, analytes can be directly immobilized on solid supports. Analyte capture agents and accessory molecules can also be immobilized on solid supports. A preferred form of solid support is a microtiter dish. Another form of solid support is an array detector. An array detector is a solid support to which multiple different address probes or detection molecules have been coupled in an array, grid, or other organized pattern.

Rolling circle amplification of decoupled amplification target circles can be performed on solid supports having reaction chambers. A reaction chamber is any structure in which a separate amplification reaction can be performed. Useful reaction chambers include wells, vessels, tubes, chambers, holes, depressions, dimples, locations, or other structures that can support separate reactions. Solid supports preferably comprise arrays of reaction chambers. In connection with reaction chambers, a separate reaction refers to a reaction where substantially no cross contamination of reactants or products will occur between different reaction chambers. Substantially no cross contamination refers to a level of contamination of reactants or products below a level that would be detected in the particular reaction or assay involved. For example, if TS-DNA contamination from another reaction chamber would not be detected in a given reaction chamber in a given assay (even though it may be present), there is no substantial cross contamination of the TS-DNA. It is understood, therefore, that reaction chambers can comprise, for example, locations on a planar surface so long as the reactions performed at the locations remain separate and are not subject to mixing.

Solid-state substrates for use in solid supports can include any solid material with which analytes can be associated, directly or indirectly. This includes materials such as acrylamide, agarose, cellulose, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A preferred form for a solid-state substrate is a microtiter dish. The most preferred form of microtiter dish is the standard 96-well type. In some embodiments, a multiwell glass slide can be employed.

Different analytes, analyte capture agents, or accessory molecules can be used together as a set. The set can be used as a mixture of all or subsets of the analytes, analyte capture agents, and accessory molecules used separately in separate reactions, or immobilized on a solid support. Analytes, analyte capture agents, and accessory molecules used separately or as mixtures can be physically separable through, for example, association with or immobilization on a solid support. An array includes a plurality of analytes, analyte capture agents and/or accessory molecules immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification of analytes.

Although preferred, it is not required that the solid support be a single unit or structure. The set of analytes, analyte capture agents, or accessory molecules may be distributed over any number of solid supports. For example, at one extreme, each probe may be immobilized in a separate reaction tube or container, or on separate beads or microparticles. Different modes of the disclosed method can be performed with different components (for example, analytes, analyte capture agents, and accessory molecules) immobilized on a solid support.

In alternative embodiments, RCA is performed in solution, and the products of the amplification are captured on a solid support. For example, the decoupled amplification target circles can be amplified together (that is, not in separate reaction chambers) and the products captured. For example, a biotinylated capture antibody can be added to a sample containing the analyte, followed by a reporter binding molecule that binds to a different location on the analyte. These components—the capture antibody and the reporter binding molecule—can be added in any order. RCA then can be performed to produce TS-DNA, and purified on a matrix containing streptavidin (streptavidin beads (Dynal), for example). The TS-DNA then can be detected or quantitated by hybridization to a solid support containing oligonucleotide probes complementary to the TS-DNA. Such probes are referred to herein as address probes. By attaching different address probes to different regions of a solid support, different RCA products can be captured at different, and therefore diagnostic, locations on the solid support. For example, in a microtiter plate multiplex assay, address probes specific for up to 96 different TS-DNAs (each amplified via different primers and ATCs) can be immobilized on a microtiter plate, each in a different well. Capture and detection will occur only in those probe elements on the solid support corresponding to TS-DNAs for which the corresponding analytes were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022-5026 (1994), and Khrapko et al., *Mol Biol* (*Mosk*) (*USSR*) 25:718-730 (1991). A method for immobilization of 3'-amine oligonucleotides on casein-coated slides is described by Stimpson et al., *Proc. Natl. Acad. Sci. USA* 92:6379-6383 (1995). A preferred method of attaching oligonucleotides to solid-state substrates is described by Guo et al., *Nucleic Acids Res.* 22:5456-5465 (1994).

Some solid supports useful in RCA assays have detection antibodies attached to a solid-state substrate. Such antibodies can be specific for a molecule of interest. Captured molecules of interest can then be detected by binding of a second, reporter antibody, followed by RCA. Such a use of antibodies in a solid support allows RCA assays to be developed for the detection of any molecule for which antibodies can be generated. Methods for immobilizing antibodies to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is the heterobifunctional cross-linker N-[γ-Maleimidobutyryloxy] succinimide ester (GMBS). These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209-216 and 241-242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the solid-state substrate. For example, antibodies may be chemically cross-linked to a substrate that contains free amino, carboxyl, or sulfur groups using glutaraldehyde, carbodiimides, or GMBS, respectively, as cross-linker agents. In this method, aqueous solutions containing free antibodies are incubated with the solid-state substrate in the presence of glutaraldehyde or carbodiimide.

A preferred method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate ($BS^3$) or a heterobifunctional cross-linker agent such as GMBS. For cross-linking with GMBS, glass substrates are chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides are activated by immersing in a 0.5 mg/ml solution of GMBS in 1% dimethylformamide, 99% ethanol for 1 hour at room temperature. Antibodies or proteins are added directly to the activated substrate, which are then blocked with solutions containing agents such as 2% bovine serum albumin, and air-dried. Other standard immobilization chemistries are known by those of skill in the art.

Each of the components (analyte capture agents, accessory molecules, and/or analytes) immobilized on the solid support preferably is located in a different predefined region of the solid support. The different locations preferably are different reaction chambers. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components preferably are immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

L. DNA Polymerases

DNA polymerases useful in the disclosed method must be capable, either alone or in combination with a compatible strand displacement factor, perform rolling circle replication of primed single-stranded circles. Such polymerases are referred to herein as rolling circle DNA polymerases. It is preferred that a rolling circle DNA polymerase lack a 5' to 3' exonuclease activity. Strand displacement is necessary to result in synthesis of multiple tandem copies of an amplification target circle. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out strand displacement replication. Preferred strand displacement DNA polymerases are Bst large fragment DNA polymerase (Exo(-) Bst; Aliotta et al., *Genet. Anal. (Netherlands)* 12:185-195 (1996)), exo(-) Bca DNA polymerase (Walker and Linn, *Clinical Chemistry* 42:1604-1608 (1996)), and bacteriophage φ29 DNA polymerase (U.S. Pat. Nos. 5,198,543 and 5,001,050 to Blanco et al.). Other useful polymerases include phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), exo(-)VENT® DNA polymerase (Kong et al., *J. Biol. Chem.* 268:1965-1975 (1993)), Klenow fragment of DNA polymerase I (Jacobsen et al., *Eur. J Biochem.* 45:623-627 (1974)), T5 DNA polymerase (Chattejee et al., *Gene* 97:13-19 (1991)), Sequenase (U.S. Biochemicals), PRD1 DNA polymerase (Zhu and Ito, *Biochim. Biophys. Acta.* 1219:267-276 (1994)), and T4 DNA polymerase holoenzyme (Kaboord and Benkovic, *Curr. Biol.* 5:149-157 (1995)). Bst DNA polymerase is most preferred.

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. Strand displacement factors useful in strand displacement replication include BMRF1 polymerase accessory subunit (Tsurumi et al., *J. Virology* 67(12):7648-7653 (1993)), adenovirus DNA-binding protein (Zijderveld and van der Vliet, *J. Virology* 68(2): 1158-1164 (1994)), herpes simplex viral protein ICP8 (Boehmer and Lehman, *J. Virology* 67(2):711-715 (1993); Skaliter and Lehman, *Proc. Natl. Acad. Sci. USA* 91(22):10665-10669 (1994)); single-stranded DNA binding proteins (SSB; Rigler and Romano, *J. Biol. Chem.* 270:8910-8919 (1995)); phage T4 gene 32 protein (Villemain and Giedroc, *Biochemistry* 35:14395-14404 (1996); and calf thymus helicase (Siegel et al., *J. Biol. Chem.* 267:13629-13635 (1992)).

The ability of a polymerase to carry out rolling circle replication can be determined by using the polymerase in a rolling circle replication assay such as those described in Fire and Xu, *Proc. Natl. Acad. Sci. USA* 92:4641-4645 (1995).

The materials described above can be packaged together in any suitable combination as a kit useful for performing the disclosed method. For example, a kit can include a plurality of reporter binding molecules and/or a plurality of analyte capture agents. The analyte capture agents in the kit can be associated with a solid support.

Method

The disclosed method is a form of rolling circle amplification (RCA) where a reporter binding molecule provides the amplification target circle for amplification. The disclosed method allows RCA to produce an amplified signal (that is, tandem sequence DNA (TS-DNA)) based on association of the reporter binding molecule with a target molecule (also referred to as an analyte). The specific amplification target circle that is a part of the reporter binding molecule provides the link between the specific interaction of the reporter binding molecule to an analyte (via the affinity portion of the reporter binding molecule) and RCA. Once the reporter binding molecule is associated with an analyte, a rolling circle replication primer is hybridized to the amplification target circle (ATC) of the reporter binding molecule, followed by amplification of the ATC by RCA (a secondary DNA strand displacement primer is also used if exponential RCA is performed). The disclosed method can be performed using any analyte. Preferred analytes are proteins, peptides, nucleic acids, including amplified nucleic acids such as TS-DNA and amplification target circles, antigens and ligands. Target molecules for the disclosed method are generally referred to herein as analytes.

The amplification target circle is released from the reporter binding molecule prior to amplification. Such release, referred to herein as decoupling, can be accomplished in any suitable manner. In general, the manner in which the amplification target circle is associated with, or linked or coupled to, the reporter binding molecule determines the form of decoupling. For example, where the amplification target circle is base paired to a circle capture probe in the reporter binding molecule, the amplification target circle can be decoupled from the reporter binding molecule by disrupting the base pairing. Where the amplification target circle is covalently coupled to the reporter binding molecule via circle linker having a cleavable bond, the amplification target circle can be decoupled from the reporter binding molecule by cleaving the cleavable bond. To identify analytes using the amplification target circles, reporter binding molecules that are not associated with analytes should be removed prior to decoupling.

Following decoupling, the amplification target circle can be replicated by rolling circle amplification. If multiple different analytes are to be detected, the amplification products of amplification target circles associated with different analytes should be distinguishable. This can be accomplished in any suitable manner. For example, the amplification target circles can be in separate locations prior to decoupling and remain separated following decoupling. The separate locations could be determined, for example, by the location of the analytes with which the amplification target circles are associated. In this case, some or all of the amplification target circles can be the same (thus producing the same amplification product). The different locations of the amplification products identifies the analyte involved. As another example, some or all of the amplification target circles that are associated with different analytes can be different (thus producing different amplification products). The different amplification products identify the analytes involved. Even if the amplification target circles are mixed together and/or amplified in the same reaction, the different amplification target circles (and thus the different corresponding analytes) can be detected and distinguished based on the differences in the amplification products.

The amplification products of RCA can be detected using any suitable technique. Real time detection, that is, detection during the RCA reaction is a preferred mode of detection with the disclosed method. Real time detection can be facilitated by use of Amplifluor™ primers. Amplifluor™ primers produce a fluorescent signal when they become incorporated into a replicated strand and are based paired with a complementary strand.

The disclosed method is particularly useful for generating a profile of analytes present in a given sample. For example, the presence and amount of various proteins present in cells can be assessed, thus providing a direct protein expression profile. Such analysis, a form of proteomics, is analogous to genomics analysis of the presence and expression of nucleic acids. Multiple analyte analysis, such as the proteomics mode of the disclosed invention, is preferably carried out using sets of analyte capture agents. By including in the set analyte capture agents specific for all of the analytes to be assessed, the full range of analytes can be assayed in a single procedure. This form of the method also allows easy comparison of the same suite of analytes in multiple samples.

In a preferred form of the disclosed method, the analytes in two (or more) different samples can be assessed in the same reaction by mixing a different set of reporter binding molecules with each sample. Each set of reporter binding molecules has the same set of specific binding molecules but a different set of amplification target circles. By making the different amplification target circles specific for different rolling circle replication primers (and different secondary DNA strand displacement primers if exponential RCA is performed), the amplification of a specific amplification target circle will indicate in which sample the corresponding analyte is present. Alternatively, by using different detection tag sequences in the different amplification target circles the amplification products of the different amplification target circles can be distinguished. This allows the identification of the analyte corresponding to a given amplification target circle.

Identification of multiple analytes can be facilitated by using analyte capture agents to capture and/or separate analytes based on their identity. For example, a set of immobilized analyte capture agents can be used to associate particular analytes with predefined regions on a solid support. Detection of an analyte in that region identifies the analyte. One useful form of analyte capture agent is peptides. When various peptides are immobilized on a solid support, they can be used as "bait" for analytes. For example, an array of different peptides can be used to access whether a sample has analytes that interact with any of the peptides. Comparisons of different samples can be made by, for example, noting differences in the peptides to which analytes in the different samples become associated. In another form of the disclosed method, a set of analyte capture agents specific for analytes of interest can be used to access the presence of a whole suite of analytes in a sample.

In another form of the disclosed method, accessory molecules can be used to affect the interaction of analytes with specific binding molecules or analyte capture agents. For example, the disclosed method can be used to screen for competitors (or binding co-factors) of an analyte interaction with a specific binding molecule or analyte capture agent. If an accessory molecule affects interaction of the analyte, the results of RCA will change since the association of the reporter binding molecule to the analyte (or of the analyte capture agent to the analyte) will be lost or gained.

Different modified forms of analytes can also be detected with the disclosed method. For example, phosphorylated and glycosylated forms of proteins can be detected. This can be accomplished, for example, by using reporter binding molecules having specific binding molecules specific for the different forms of analyte.

In another aspect, the disclosed method involves immobilization of analytes present in complex biological samples and determining and quantitating their presence in the samples. In another aspect, the disclosed method involves multiplexed detection and quantitation of more than one analytes in a sample. For example, a solid support containing immobilized capture antibodies can be incubated with sample containing a mixture of protein analytes to be detected. The solid support next can be incubated with a mixture containing at least one biotinylated antibody for each analyte. An immunoRCA assay then can be employed for detection and quantitation.

In another aspect, an immunoRCA assay can be performed in 16 microwell-glass slides, wherein each well is separated by a Teflon mask. Each of these wells can be used, for example, to assay different samples and controls, to assay different analytes, or to assay different sets of analytes. Multiwell slides also can be printed with arrays of anti-IgE capture antibodies in the wells. Semi-automation of immunoRCA assays on allergen microarrays in this multiwell format can be implemented, for example, on an inexpensive Beckman BioMek liquid handling robot.

ImmunoRCA assay can be applied to other multiplexed antibody assays. For example, certain immunological reactions are caused by specific $IgG_4$ rather than IgE (AAAI Board of Directors, *J. Allergy Clin Immunol.* 95:652-654 (1995)). The use of an anti-human $IgG_4$ conjugated to a DNA circle that is different in sequence from the DNA circle conjugated to an anti-IgE would allow the simultaneous measurement of allergen-specific $IgG_4$ and IgE. Such an assay can be used during allergen desensitization therapy or for monitoring response to anti-IgE therapy (Chang *Nature Biotech.* 18:157-162 (2000)).

The disclosed method generally includes the following steps:

(a) Bringing into contact one or more analyte samples and one or more reporter binding molecules, incubating the analyte samples and the reporter binding molecules under conditions that promote interaction of the specific binding molecules and analytes, and separating the specific binding molecules that interact with the analytes from the specific binding molecules that do not interact with the analytes. Each reporter binding molecule comprises a specific binding molecule and an amplification target circle, wherein each specific binding molecule interacts with an analyte directly or indirectly.

(b) Decoupling the amplification target circles from the reporter binding molecules that interact with the analytes.

(c) Bringing into contact the amplification target circles and one or more rolling circle replication primers, and incubating the rolling circle replication primers and amplification target circles under conditions that promote hybridization between the amplification target circles and the rolling circle replication primers. The amplification target circles each comprise a single-stranded, circular DNA molecule comprising a primer complement portion, wherein the primer complement portion is complementary to at least one of the rolling circle replication primers.

(d) Incubating the rolling circle replication primers and amplification target circles under conditions that promote replication of the amplification target circles. Replication of the amplification target circles results in the formation of tandem sequence DNA, wherein detection of tandem sequence DNA indicates the presence of the corresponding analytes.

The method can also be performed where at least one of the reporter binding molecules further comprises a circle capture probe, and where the amplification target circle of the reporter binding molecule is associated with the reporter binding molecule via a non-covalent interaction with the circle capture probe. The non-covalent interaction can be base pairing. Decoupling of the amplification target circle can be accomplished by disrupting the base pairing. Base pairing can be disrupted by heating the reporter binding molecules. The circle capture probe can comprise an oligonucleotide. In some embodiments, the oligonucleotide cannot be extended. For example, the oligonucleotide can comprise a 3' end and a 5' end, wherein only the 5' end is free. The oligonucleotide can be coupled to the specific binding molecule of the reporter binding molecule via the 3' end of the oligonucleotide, the 3' end of the oligonucleotide can be blocked, or the oligonucleotide can be blocked.

The method can also be performed where at least one of the reporter binding molecules further comprises a circle linker, and where the amplification target circle of the reporter binding molecule is coupled to the reporter binding molecule via the circle linker. The circle linker can comprise a cleavable bond. Decoupling of the amplification target circle can be accomplished by cleaving the cleavable bond. In some embodiments, the cleavable bond can be cleaved by treatment with a reducing agent. The cleavable bond can be a disulfide bond. For example the circle linker can comprise dithiobis succinimidyl propionate, dimethyl 3,3'-dithiobispropionimidate, dithio-bis-maleimidoethane, 3,3'-dithiobis sulfosuccinimidyl propionate, succinimidyl 6-[3-(2-pyridyldithio)-propionamido]hexonate, or N-succinimidyl 3-[2-pyridyldithio] propionate. In some embodiments, the cleavable bond can be cleaved by treatment with periodate. The cleavable bond can be a dihydroxy bond. For example, the circle linker can comprise 1,4 bis-maleimidyl-2,3-dihydroxybutane, disuccinimidyl tartrate, or disulfosuccinimidyl tartrate. The circle linker can be coupled to the amplification target circle via a reactive group on the amplification target circle. The reactive group can be an allyl amino group.

The method can be performed wherein a plurality of reporter binding molecules are brought into contact with the one or more analyte samples; wherein a plurality of analyte samples are brought into contact with the one or more reporter binding molecules; wherein at least one of the analytes is a protein or peptide; wherein at least one of the analytes is a lipid, glycolipid, or proteoglycan; wherein at least one of the analytes is from a human source; wherein at least one of the analytes is from a non-human source; wherein none of the analytes are nucleic acids; wherein at least one of the specific binding molecules is an antibody specific for at least one of the analytes; wherein at least one of the specific binding molecules is a molecule that specifically binds to at least one of the analytes; wherein at least one of the specific binding molecules is a molecule that specifically binds to at least one of the analytes in combination with an accessory molecule; and/or wherein the specific binding molecules and analytes interact by binding to each other directly or indirectly. The reporter binding molecules can be at least 20% pure, at least 50% pure, at least 80% pure, or at least 90% pure.

The method can also include bringing into contact at least one of the analyte samples and one or more analyte capture agents, and separating analyte capture agents from the analyte samples, thus separating analytes from the analyte samples. Each analyte capture agent interacts with an analyte directly or indirectly, and at least one analyte, if present in the analyte sample, interacts with at least one analyte capture agent. The method can also include bringing into contact at least one of the analyte samples and at least one of the reporter binding molecules with at least one accessory molecule. The accessory molecule affects the interaction of at least one of the analytes and at least one of the specific binding molecules or at least one of the analyte capture agents.

The method can further comprise, simultaneous with, or following, step (d), bringing into contact a secondary DNA strand displacement primer and the tandem sequence DNA, and incubating under conditions that promote (i) hybridization between the tandem sequence DNA and the secondary DNA strand displacement primer, and (ii) replication of the tandem sequence DNA, wherein replication of the tandem sequence DNA results in the formation of secondary tandem sequence DNA. In this form of the method, the rolling circle replication primer can hybridize to the secondary tandem sequence DNA and the secondary tandem sequence DNA can be replicated to form tertiary tandem sequence DNA. The rolling circle replication primer and secondary DNA strand displacement primer can continue to hybridize with and replicate the tandem sequence DNA, secondary tandem sequence DNA, tertiary tandem sequence DNA (and other higher order tandem sequence DNAs) to form more amplified DNA (that is, various generations of tandem sequence DNA).

This form of the method can further comprise, simultaneous with, or following, step (d), bringing into contact a tertiary DNA strand displacement primer and the secondary tandem sequence DNA, and incubating under conditions that promote (i) hybridization between the secondary tandem sequence DNA and the tertiary DNA strand displacement primer, and (ii) replication of the secondary tandem sequence DNA, wherein replication of the secondary tandem sequence DNA results in the formation of tertiary tandem sequence DNA. The tertiary DNA strand displacement primer and secondary DNA strand displacement primer can continue to hybridize with and replicate the tandem sequence DNA, secondary tandem sequence DNA, tertiary tandem sequence DNA (and other higher order tandem sequence DNAs) to form more amplified DNA (that is, various generations of tandem sequence DNA). In this form of the method, the rolling circle replication primer can be used as the tertiary DNA strand displacement primer.

The method can be performed wherein a plurality of reporter binding molecules are brought into contact with one or more analyte samples, wherein two or more of the amplification target circles are replicated in the same reaction, wherein the amplification target circles replicated in the same reaction are different, wherein each different amplification target circle produces a different tandem sequence DNA, wherein the presence or absence of different analytes is indicated by the presence or absence of corresponding tandem sequence DNA. Replication of each different amplification target circle can be primed by a different one of the rolling circle replication primers.

The method can be performed wherein at least one of the analytes is associated with a solid support. The solid support can comprise one or more reaction chambers, wherein a plurality of the analytes associated with the solid support are associated with the solid support in the same reaction chamber. At least one of the analytes associated with the solid support can be associated with the solid support indirectly. The analytes associated with the solid support can interact with analyte capture agents, wherein the analyte capture agents are associated with the solid support thereby indirectly associating the analytes with the solid support.

The method can be performed wherein at least one specific binding molecule interacts with at least one analyte indirectly. The analyte can interact with an analyte capture agent, wherein the specific binding molecule interacts with the analyte capture agent thereby indirectly associating the specific binding molecule with the analyte. The method can be performed wherein at least one of the analytes is a modified form of another analyte, wherein the specific binding molecule of at least one of the reporter binding molecules interacts, directly or indirectly, with the analyte that is a modified form of the other analyte, wherein the specific binding molecule of another reporter binding molecule interacts, directly or indirectly, with the other analyte. The analytes can be proteins, wherein the modification of the modified form of the other analyte can be a post-translational modification. The modification can be phosphorylation or glycosylation.

The method can be performed wherein detection of the tandem sequence DNA is accomplished by mixing a set of detection probes with the tandem sequence DNA under conditions that promote hybridization between the tandem sequence DNA and the detection probes. A plurality of different tandem sequence DNAs can be detected separately and simultaneously via multiplex detection. The set of detection probes can be labeled using combinatorial multicolor coding.

In one form of the method, the specific binding molecules that interact with the analytes can be separated by bringing into contact at least one of the analyte samples and one or more analyte capture agents, and separating analyte capture agents from the analyte samples, thus separating specific binding molecules that interact with the analytes from the analyte samples. Each analyte capture agent can interact with an analyte directly or indirectly, and at least one analyte, if present in the analyte sample, can interact with at least one analyte capture agent. At least one analyte capture agent can be associated with a solid support, wherein analytes that interact with the analyte capture agent associated with a solid support become associated with the solid support. The solid support can comprise one or more reaction chambers, wherein a plurality of the analyte capture agents are located in the same reaction chamber on the solid support.

In this form of the method, a plurality of reporter binding molecules can be brought into contact with one or more analyte samples, wherein two or more of the amplification target circles are replicated in the same reaction chamber of the solid support, wherein the amplification target circles replicated in the same reaction chamber of the solid support are different, and wherein each different amplification target circle produces a different tandem sequence DNA. The presence or absence of different analytes is indicated by the presence or absence of corresponding tandem sequence DNA. Replication of each different amplification target circle can be primed by a different one of the rolling circle replication primers.

The solid support can comprise acrylamide, agarose, cellulose, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, or polyamino acids.

This form of the method can further comprise bringing into contact at least one of the analyte samples and at least one of the reporter binding molecules with at least one accessory molecule, wherein the accessory molecule affects the interaction of at least one of the analytes and at least one of the specific binding molecules or at least one of the analyte capture agents. The accessory molecule can be brought into contact with at least one of the analyte samples, at least one of the reporter binding molecules, or both, prior to, simultaneous with, or following step (a). At least one analyte capture agent can be associated with a solid support, wherein the accessory molecule is associated with the solid support. The accessory molecule can be associated with the solid support by bringing the accessory molecule into contact with the solid support prior to, simultaneous with, or following step (a). The accessory molecule can be a protein kinase, a protein phosphatase, an enzyme, or a compound. The accessory molecule can be a molecule of interest, wherein one or more of the analytes are test molecules, wherein interactions of the test molecules with the molecule of interest are detected. At least one of the analytes can be a molecule of interest, wherein the accessory molecule is a test molecule, wherein interactions of the test molecule with the molecule of interest are detected.

In this form of the method, the analyte samples can include one or more first analyte samples and one or more second analyte samples, wherein the reporter binding molecules include one or more first reporter binding molecules and one or more second reporter binding molecules. The method can further comprise, following step (a) and prior to bringing the analyte samples and the solid support into contact, mixing one or more of the first analyte samples and one or more of the second analyte samples. For each first reporter binding molecule there is a matching second reporter binding molecule, wherein the specific binding molecules of the first reporter binding molecules interacts with the same analyte as the specific binding molecules of the matching second reporter binding molecule. The amplification target circle of each different reporter binding molecule is different, and each different amplification target circle produces a different tandem sequence DNA. The presence or absence of the same analyte in different analyte samples is indicated by the presence or absence of corresponding tandem sequence DNA. Replication of each different amplification target circle can be primed by a different one of the rolling circle replication primers. The tandem sequence DNA corresponding to one of the analytes and produced in association with a first reporter binding molecule is in the same location on the solid support as tandem sequence DNA corresponding to the same analyte and produced in association with the matching second reporter binding molecule. The presence or absence of the same analyte in different analyte samples is indicated by the presence or absence of corresponding tandem sequence DNA.

In this form of the method, at least one of the analyte capture agents is a molecule of interest, wherein one or more of the analytes are test molecules, wherein interactions of the test molecules with the molecule of interest are detected; or at least one of the analytes is a molecule of interest, wherein one or more of the analyte capture agents are test molecules, wherein interactions of the test molecules with the molecule of interest are detected.

Another form of the method further comprises, prior to, simultaneous with, or following step (a), bringing into contact one or more first analyte capture agents and one or more first analyte samples, and bringing into contact one or more second analyte capture agents and one or more second analyte samples. Each analyte capture agent comprises an analyte interaction portion and a capture portion, wherein for each first analyte capture agent there is a matching second analyte capture agent. The analyte interaction portions of the first analyte capture agents interact with the same analyte as the analyte interaction portions of the matching second analyte capture agents. The capture portions of the first and second analyte capture agents each interact with a specific binding molecule of one or more of the reporter binding molecules, wherein the capture portions of the first analyte capture agents interact with different specific binding molecules than the capture portions of the matching second analyte capture agents. Each different specific binding molecule is part of a different one of the reporter binding molecules, wherein the amplification target circle of each different reporter binding molecule is different, wherein replication of each different amplification target circle is primed by a different one of the rolling circle replication primers, wherein each different amplification target circle produces a different tandem sequence DNA, wherein the amplification target circle of a reporter binding molecule that comprises a specific binding molecule that interacts with an analyte capture agent corresponds to the analyte capture agent. The presence or absence of the same analyte in different analyte samples is indicated by the presence or absence of corresponding tandem sequence DNA.

This form of the method can further comprise mixing one or more of the first analyte samples and one or more of the second analyte samples, or mixing the one or more first analyte capture agents and the one or more second analyte capture agents. Mixing the one or more first analyte capture agents and the one or more second analyte capture agents can be accomplished by associating, simultaneously or sequentially, the one or more first analyte capture agents and the one or more second analyte capture agents with the same solid support.

In this form of the method, the tandem sequence DNA corresponding to one of the analytes and produced in association with a first analyte capture agent can be in the same location as, and can be simultaneously detected with, tandem sequence DNA corresponding to the same analyte and produced in association with the matching second analyte capture agent. The presence or absence of the same analyte in different analyte samples is indicated by the presence or absence of corresponding tandem sequence DNA.

In this form of the method, the capture portion of each first analyte capture agent can be the same, wherein the reporter binding molecules corresponding to the first analyte capture agents are the same, wherein the amplification target circles corresponding to the first analyte capture agents are the same. The capture portion of each second analyte capture agent can be the same, wherein the reporter binding molecules corresponding to the second analyte capture agents are the same, wherein the amplification target circles corresponding to the second analyte capture agents are the same.

In another form of the method, at least one accessory molecule can be brought into contact with at least one of the analyte samples and at least one of the reporter binding molecules, wherein the accessory molecule affects the interaction of at least one of the analytes and at least one of the specific binding molecules or at least one of the analyte capture agents. The accessory molecule can compete with the interaction of at least one of the specific binding molecules or at least one of the analyte capture agents. The accessory molecule can be an analog of at least one of the analytes. The accessory molecule can facilitate the interaction of at least one of the specific binding molecules or at least one of the analyte capture agents. The accessory molecule can be brought into contact with at least one of the analyte samples, at least one of the reporter binding molecules, or both, prior to, simultaneous with, or following step (a).

In this form of the method, the accessory molecule can be a protein kinase, a protein phosphatase, an enzyme, or a compound. The accessory molecule can be at least 20% pure, at least 50% pure, at least 80% pure, or at least 90% pure.

Another form of the disclosed method generally includes the following steps:

(a) Bringing into contact one or more analyte samples and one or more analyte capture agents, and incubating the analyte samples and the analyte capture agents under conditions that promote interaction of the analyte capture agents and analytes. Each analyte capture agent can interact with an analyte directly or indirectly. At least one analyte, if present in the analyte sample, can interact with at least one analyte capture agent.

(b) Bringing into contact at least one of the analyte samples and one or more reporter binding molecules, incubating the analyte samples and the reporter binding molecules under conditions that promote interaction of the specific binding molecules and analyte capture agents, and separating the specific binding molecules that interact with the analyte capture agents from the specific binding molecules that do not interact with the analyte capture agents. Each reporter binding molecule can comprise a specific binding molecule and an amplification target circle, and each specific binding molecule can interact with an analyte capture agent directly or indirectly.

(c) Decoupling the amplification target circles from the reporter binding molecules that interact with the analyte capture agents.

(d) Bringing into contact the amplification target circles and one or more rolling circle replication primers, and incubating the rolling circle replication primers and amplification target circles under conditions that promote hybridization between the amplification target circles and the rolling circle replication primers. The amplification target circles each can comprise a single-stranded, circular DNA molecule comprising a primer complement portion, and the primer complement portion is complementary to at least one of the rolling circle replication primers.

(e) Incubating the rolling circle replication primers and amplification target circles under conditions that promote replication of the amplification target circles. Replication of the amplification target circles results in the formation of tandem sequence DNA, wherein detection of tandem sequence DNA indicates the presence of the corresponding analytes.

Another form of the disclosed method generally includes the following steps:

(a) Treating one or more analyte samples so that one or more analytes are modified.

(b) Bringing into contact at least one of the analyte samples and one or more reporter binding molecules, incubating the analyte samples and the reporter binding molecules under conditions that promote interaction of the specific binding molecules and modified analytes, and separating the specific binding molecules that interact with the modified analytes from the specific binding molecules that do not interact with the modified analytes. Each reporter binding molecule can comprise a specific binding molecule and an amplification target circle, and each specific binding molecule can interact with a modified analyte directly or indirectly.

(c) Decoupling the amplification target circles from the reporter binding molecules that interact with the modified analytes.

(d) Bringing into contact the amplification target circles and one or more rolling circle replication primers, and incubating the rolling circle replication primers and amplification target circles under conditions that promote hybridization between the amplification target circles and the rolling circle replication primers. The amplification target circles each can comprise a single-stranded, circular DNA molecule comprising a primer complement portion, and the primer complement portion is complementary to at least one of the rolling circle replication primers.

(e) Incubating the rolling circle replication primers and amplification target circles under conditions that promote replication of the amplification target circles. Replication of the amplification target circles results in the formation of tandem sequence DNA, wherein detection of tandem sequence DNA indicates the presence of the corresponding modified analytes.

In this form of the method, all of the analytes can be modified by associating a modifying group to the analytes, wherein the modifying group is the same for all of the analytes, wherein all of the specific binding molecules interact with the modifying group.

Another form of the disclosed method generally includes the following steps:

(a) Bringing into contact one or more analyte samples and a set of analyte capture agents, a set of accessory molecules, or both. Each analyte capture agent can interact with an analyte directly or indirectly.

(b) Prior to, simultaneous with, or following step (a), bringing into contact at least one of the analyte samples and one or more reporter binding molecules. Each reporter binding molecule can comprise a specific binding molecule and an amplification target circle, each specific binding molecule can interact with an analyte directly or indirectly, and each accessory molecule can affect the interaction of at least one of the analytes and at least one of the specific binding molecules or at least one of the analyte capture agents.

(c) Simultaneous with, or following, steps (a) and (b), incubating the analyte samples, the analyte capture agents, the accessory molecules, and the reporter binding molecules under conditions that promote interaction of the specific binding molecules, analytes, analyte capture agents, and accessory molecules, separating the specific binding molecules that interact with the analytes from the specific binding molecules that do not interact with the analytes, and decoupling the amplification target circles from the reporter binding molecules that interact with the analytes.

(d) Bringing into contact the amplification target circles and one or more rolling circle replication primers, and incubating the rolling circle replication primers and amplification target circles under conditions that promote hybridization between the amplification target circles and the rolling circle replication primers. The amplification target circles each can comprise a single-stranded, circular DNA molecule comprising a primer complement portion, and the primer complement portion is complementary to at least one of the rolling circle replication primers.

(e) Incubating the reporter binding molecules and amplification target circles under conditions that promote replication of the amplification target circles. Replication of the amplification target circles results in the formation of tandem sequence DNA, wherein detection of tandem sequence DNA indicates the presence of the corresponding analytes.

The method can also be performed where the analyte capture agents are immobilized on a solid support, where the solid support comprises one or more reaction chambers, and where a plurality of the analyte capture agents are immobilized in the same reaction chamber of the solid support. The analyte capture agents can be immobilized to the solid support at a density exceeding 400 different analyte capture agents per cubic centimeter. The analyte capture agents can be peptides. Each of the different peptides can be at least 4 amino acids in length, from about 4 to about 20 amino acids in length, at least 10 amino acids in length, or at least 20 amino acids in length.

The solid support can comprise a plurality of reaction chambers. The solid support can comprise acrylamide, agarose, cellulose, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, or polyamino acids.

The analyte capture agents in the reaction chambers can be at least 20% pure, at least 50% pure, at least 80% pure, or at least 90% pure.

Another form of the disclosed method generally includes:

Bringing into contact one or more analyte samples and one or more reporter binding molecules. Each reporter binding molecule can comprise a specific binding molecule and an amplification target circle, and each specific binding molecule can interact with an analyte directly or indirectly.

Separating the specific binding molecules that interact with the analytes from the specific binding molecules that do not interact with the analytes.

Decoupling the amplification target circles from the reporter binding molecules that interact with the analytes.

Replicating the amplification target circles. Replication of the amplification target circles results in the formation of tandem sequence DNA, wherein detection of tandem sequence DNA indicates the presence of the corresponding analytes.

Another form of the disclosed method generally includes:

Bringing into contact one or more analyte samples and one or more analyte capture agents. Each analyte capture agents can interact with an analyte directly or indirectly.

Bringing into contact at least one of the analyte samples and one or more reporter binding molecules. Each reporter binding molecule can comprise a specific binding molecule and an amplification target circle, and each specific binding molecule can interact with an analyte capture agent directly or indirectly.

Separating the specific binding molecules that interact with the analyte capture agents from the specific binding molecules that do not interact with the analyte capture agents.

Decoupling the amplification target circles from the reporter binding molecules that interact with the analyte capture agents.

Replicating the amplification target circles. Replication of the amplification target circles results in the formation of tandem sequence DNA, wherein detection of tandem sequence DNA indicates the presence of the corresponding analytes.

Another form of the disclosed method generally includes:

Treating one or more analyte samples so that one or more analytes are modified.

Bringing into contact at least one analyte samples and one or more reporter binding molecules. Each reporter binding molecule can comprise a specific binding molecule and an amplification target circle, and each specific binding molecule can interact with a modified analyte directly or indirectly.

Separating the specific binding molecules that interact with the modified analytes from the specific binding molecules that do not interact with the modified analytes.

Decoupling the amplification target circles from the reporter binding molecules that interact with the modified analytes.

Replicating the amplification target circles. Replication of the amplification target circles results in the formation of tandem sequence DNA, wherein detection of tandem sequence DNA indicates the presence of the corresponding modified analytes.

Another form of the disclosed method generally includes:

Bringing into contact one or more analyte samples and a set of analyte capture agents, a set of accessory molecules, or both, wherein each analyte capture agent can interact with an analyte directly or indirectly, Bringing into contact at least one of the analyte samples and one or more reporter binding molecules. Each reporter binding molecule can comprise a specific binding molecule and an amplification target circle, each specific binding molecule can interact with an analyte directly or indirectly, and each accessory molecule can affect the interaction of at least one of the analytes and at least one of the specific binding molecules or at least one of the analyte capture agents.

Separating the specific binding molecules that interact with the analytes from the specific binding molecules that do not interact with the analytes.

Decoupling the amplification target circles from the reporter binding molecules that interact with the analytes.

Replicating the amplification target circles. Replication of the amplification target circles results in the formation of tandem sequence DNA, wherein detection of tandem sequence DNA indicates the presence of the corresponding analytes.

The amplification target circles serve as substrates for a rolling circle replication. This reaction requires the addition of two reagents: (a) a rolling circle replication primer, which is complementary to the primer complement portion of the ATC, and (b) a rolling circle DNA polymerase. The DNA polymerase catalyzes primer extension and strand displacement in a processive rolling circle polymerization reaction that proceeds as long as desired, generating a molecule of up to 100,000 nucleotides or larger that contains up to approximately 1000 tandem copies of a sequence complementary to the amplification target circle. A preferred rolling circle DNA polymerase is Bst DNA polymerase.

Many different forms of RCA can be used in the disclosed method, most of which are described in U.S. Pat. No. 5,854,033 and WO 97/19193. For example, linear rolling circle amplification (LRCA) involves the basic rolling circle replication of an amplification target circle to form a strand of TS-DNA. Exponential rolling circle amplification (ERCA) involves replication of TS-DNA by strand displacement replication initiated at the numerous repeated sequences in the TS-DNA. Multiple priming on both strands of TS-DNA leads to an exponential amplification of sequences in the amplification target circle. ERCA is preferred for the disclosed method. If desired, the TS-DNA can be collapsed into a compact structure for detection as described in WO 97/19193.

During rolling circle replication one may additionally include radioactive or modified nucleotides such as bromodeoxyuridine triphosphate, in order to label the DNA generated in the reaction. Alternatively, one may include suitable precursors that provide a binding moiety such as biotinylated nucleotides (Langer et al. (1981)).

Examples of proteins that can be analyzed and detected using the disclosed method include IL-1alpha, IL-1beta, IL-1RA, IL-2, IL-3, IL-4, IL-6, IL-6R, IL-7, IL-8, IL-9, IL-10, GROalpha, MIP-1alpha, MIP-1beta, MCP, RANTES, MIF, G-CSF, GM-CSF, M-CSF, EGF, FGF acidic, FGF basic, IGF-1, IGF-2, IFN-gamma, TGF-beta, TNF-alpha, TNF-beta, TNF-RI, TNF-RII, ICAM-1, ICAM-2, IL-2Ra, IL-4R, IL-5, IL-11, IL-12, IL-13, IL-15, IL-16, IL-17, IL-18, IP-10, FGF-4, FGF-6, MCP-2, and MCP3.

A. Detection of Amplification Products

Amplification products can be detected directly by, for example, primary labeling or secondary labeling, as described below.

i. Primary Labeling

Primary labeling consists of incorporating labeled moieties, such as fluorescent nucleotides, biotinylated nucleotides, digoxygenin-containing nucleotides, or bromodeoxyuridine, during strand displacement replication. For example, one may incorporate cyanine dye deoxyuridine analogs (Yu et al., *Nucleic Acids Res.,* 22:3226-3232 (1994)) at a frequency of 4 analogs for every 100 nucleotides. A preferred method for detecting nucleic acid amplified in situ is to label the DNA during amplification with BrdUrd, followed by binding of the incorporated BrdU with a biotinylated anti-BrdU antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.). Other methods for detecting nucleic acid amplified in situ include labeling the DNA during amplification with 5-methylcytosine, followed by binding of the incorporated 5-methylcytosine with an antibody (Sano et al., *Biochim. Biophys. Acta* 951:157-165 (1988)), or labeling the DNA during amplification with aminoallyl-deoxyuridine, followed by binding of the incorporated aminoallyl-deoxyuridine with an Oregon Green® dye (Molecular Probes, Eugene, Oreg.) (Henegariu et al., *Nature Biotechnology* 18:345-348 (2000)).

Another method of labeling amplified nucleic acids is to incorporate 5-(3-aminoallyl)-dUTP (AAdUTP) in the nucleic acid during amplification followed by chemical labeling at the incorporated nucleotides. Incorporated 5-(3-aminoallyl)-deoxyuridine (AAdU) can be coupled to labels that have reactive groups that are capable of reacting with amine groups. AAdUTP can be prepared according to Langer et al. (1981). Proc. Natl. Acad. Sci. USA. 78: 6633-37. Other modified nucleotides can be used in analogous ways. That is, other modified nucleotides with minimal modification can be incorporated during replication and labeled after incorporation.

Examples of labels suitable for addition to AAdUTP are radioactive isotopes, fluorescent molecules, phosphorescent molecules, enzymes, antibodies, and ligands. Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH$_3$, Diamino Phenyl Oxydiazole (DAO), Dimethylamino-5-Sulphonic acid, Dipyrromethaneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxy-fluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 mn) and Cy7 (755 run; 778 nm), thus allowing their simultaneous detection. Other examples of fluorescein dyes include 6-carboxyfluorescein (6-FAM), 2',4', 1,4,-tetrachlorofluorescein (TET), 2',4',5',7', 1,4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Another useful label, related to molecular beacon technology, is Amplifluors™. Amplifluors™ are fluorescent moieties and quenchers incorporated into primers containing stem structures (usually in hairpin or stem and loop structures) such that the quencher moiety is in proximity with the fluorescent moiety. That is, the quencher and fluorescent are incorporated into opposite strands of the stem structure. In the structured state, the quencher prevents or limits fluorescence of the fluorescent moiety. When the stem of the primer is disrupted, the quencher and fluorescent moiety are no longer in proximity and the fluorescent moiety produces a fluorescent signal. In the disclosed method, use of Amplifluor™ primers in ERCA produces double stranded tandem sequence DNA where the primer stem is disrupted in favor of a complementary, replicated strand. From a reaction initially containing structured (that is, non-fluorescent) Amplifluor™ primers, fluorescence signal increases as amplification takes place, as more and more of the Amplifluor™ primers are incorporated into double stranded TS-DNA, as the Amplifluor™ stems are disrupted, and as the fluorescent moieties as consequently unquenched. Thus, use of Amplifluors™ is particularly suited for real-time detection of amplification in ERCA.

The amplification products of RCA can be detected using any suitable technique. Real time detection, that is, detection during the RCA reaction is a preferred mode of detection with the disclosed method. Real time detection can be facilitated by use of Amplifluor™ primers. Amplifluor™ primers produce a fluorescent signal when they become incorporated into a replicated strand and are based paired with a complementary strand.

2. Secondary Labeling with Detection Probes

Secondary labeling consists of using suitable molecular probes, referred to as detection probes, to detect the amplified DNA or RNA. For example, an amplification target circle may be designed to contain several repeats of a known arbitrary sequence, referred to as detection tags. A secondary hybridization step can be used to bind detection probes to these detection tags. The detection probes may be labeled as described above with, for example, an enzyme, fluorescent moieties, or radioactive isotopes. By using three detection tags per amplification target circle, and four fluorescent moieties per each detection probe, one may obtain up to twelve fluorescent signals for every amplification target circle repeat in the TS-DNA, yielding up to 12,000 fluorescent moieties for every amplification target circle that is amplified by RCA.

3. Multiplexing and Hybridization Array Detection

RCA is easily multiplexed by using sets of different amplification target circles, each set carrying different address tag sequences designed for binding to unique address probes. Note that although the address tag sequences for each amplification target circle are different, the primer complement portion may remain unchanged, and thus the primer for rolling circle replication can remain the same for all targets. The TS-DNA molecules generated by RCA are of high molecular weight and low complexity; the complexity being the length of the amplification target circle. A given TS-DNA can be captured to a fixed position in a solid support by, for example, including within the spacer region of the amplification target circles a unique address tag sequence for each unique amplification target circle. TS-DNA generated from a given amplification target circle will then contain sequences corresponding to a specific address tag sequence.

4. Combinatorial Multicolor Coding

A preferred form of multiplex detection involves the use of a combination of labels that either fluoresce at different wavelengths or are colored differently. One of the advantages of fluorescence for the detection of hybridization probes is that several targets can be visualized simultaneously in the same sample. Using a combinatorial strategy, many more targets can be discriminated than the number of spectrally resolvable fluorophores. Combinatorial labeling provides the simplest way to label probes in a multiplex fashion since a probe fluor is either completely absent (−) or present in unit amounts (+); image analysis is thus more amenable to automation, and a number of experimental artifacts, such as differential photobleaching of the fluors and the effects of changing excitation source power spectrum, are avoided.

The combinations of labels establish a code for identifying different detection probes and, by extension, different analytes to which those detection probes are associated with. This labeling scheme is referred to as Combinatorial Multicolor Coding (CMC). Such coding is described by Speicher et al., *Nature Genetics* 12:368-375 (1996). Any number of labels, which when combined can be separately detected, can be used for combinatorial multicolor coding. It is preferred that 2, 3, 4, 5, or 6 labels be used in combination. It is most preferred that 6 labels be used. The number of labels used establishes the number of unique label combinations that can be formed according to the formula $2^N-1$, where N is the number of labels. According to this formula, 2 labels forms three label combinations, 3 labels forms seven label combinations, 4 labels forms 15 label combinations, 5 labels form 31 label combinations, and 6 labels forms 63 label combinations.

Speicher et al. describes a set of fluors and corresponding optical filters spaced across the spectral interval 350-770 nm that give a high degree of discrimination between all possible fluor pairs. This fluor set, which is preferred for combinatorial multicolor coding, consists of 4'-6-diamidino-2-phenylindole (DAPI), fluorescein (FITC), and the cyanine dyes Cy3, Cy3.5, Cy5, Cy5.5 and Cy7. Any subset of this preferred set can also be used where fewer combinations are required. The absorption and emission maxima, respectively, for these fluors are: DAPI (350 nm; 456 nm), FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm). The excitation and emission spectra, extinction coefficients and quantum yield of these fluors are described by Ernst et al., *Cytometry* 10:3-10 (1989), Mujumdar et al., *Cytometry* 10:11-19 (1989), Yu, *Nucleic Acids Res.* 22:3226-3232 (1994), and Waggoner, *Meth. Enzymology* 246:362-373 (1995). These fluors can all be excited with a 75 W Xenon arc.

B. Further Amplification

Secondary DNA strand displacement is another way to amplify TS-DNA. Secondary DNA strand displacement is accomplished by hybridizing secondary DNA strand displacement primers to TS-DNA and allowing a DNA polymerase to synthesize DNA from these primed sites. The product of secondary DNA strand displacement is referred to as secondary tandem sequence DNA or TS-DNA-2. Secondary DNA strand displacement and strand displacement cascade amplification are described in U.S. Pat. No. 5,854,033 and WO 97/19193. Strand displacement cascade amplification, also referred to as exponential rolling circle amplification (ERCA) is a preferred form of RCA for use in the disclosed method.

In exponential RCA, a secondary DNA strand displacement primer primes replication of TS-DNA to form a complementary strand referred to as secondary tandem sequence DNA or TS-DNA-2. As a secondary DNA strand displacement primer is elongated, the DNA polymerase will run into the 5' end of the next hybridized secondary DNA strand displacement molecule and will displace its 5' end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. A tertiary DNA strand displacement primer strand (which is complementary to the TS-DNA-2 strand and which can be the rolling circle replication primer) can then hybridize to, and prime replication of, TS-DNA-2 to form TS-DNA-3 (which is equivalent to the original TS-DNA). Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. The additional forms of tandem sequence DNA beyond secondary tandem sequence DNA are collectively referred to herein as higher order tandem sequence DNA. Higher order tandem sequence DNA encompasses TS-DNA-3, TS-DNA-4, and any other tandem sequence DNA produced from replication of secondary tandem sequence DNA or the products of such replication. In a preferred mode of ERCA, the rolling circle replication primer serves as the tertiary DNA strand displacement primer, thus eliminating the need for a separate primer. Exponential rolling circle amplification is further described in U.S. Pat. No. 5,854,033 and WO 97/19193 (where it is referred to as strand displacement cascade amplification).

Illustrations

The disclosed method can be further described by the following illustrations.

One form of the disclosed method involving the use of circle capture probes for the detection of HIV p24 antigen is described below.

Microtiter plates will be pre-coated with mouse anti-HIV p24 antibody. Incubation of sample with HIV p24 with antibody-coated microtiter plates will result in the binding of HIV p24 antigen to antibodies anchored on to the plates. Plate bound HIV p24 antigen will then be recognized by polyclonal anti-HIV p24 goat antibody that has been conjugated with the amplification target circle (the conjugate is the reporter binding molecule) and has been preannealed to a RCA circle. Subsequent to washing, captured amplification target circles will be released (decoupled) during ERCA amplification using appropriate primers. RCA signals will be detected with either a plate reader or ABI-7700 real time instrument and using Amplifluors™ or molecular beacons.

Another form of the disclosed method involving the use of circle linkers for the detection of antigens is described below.

Microtiter plates will be pre-coated with appropriate capture antibodies, in an arrayed fashion, for analyte detection. Incubation of test samples will result in the binding of specific analyte to antibodies anchored on to the plates. Plate bound analytes will then be recognized by a detector antibody that has been conjugated with the amplification target circle (the conjugate is the reporter binding molecule) via a cleavable linker (that is, a circle linker). Subsequent to washing, antibody-conjugated amplification target circle will be released (decoupled), inside a microtiter plate, by cleaving the linker (for example, by DTT treatment to cleave disulfide linkage). Released amplification target circle will be used for signal amplification by ERCA. The signal detection will be carried out with either a real time assay instrument (ABI 7700 sequence detector) or a plate reader using Amplifluors™ or molecular beacons.

EXAMPLES

The disclosed method can be further described, and relevant principles illustrated, through the following examples.

A. Example 1

Coating of Micro Amp Polypropylene Tubes with Antibody

Figure 2:
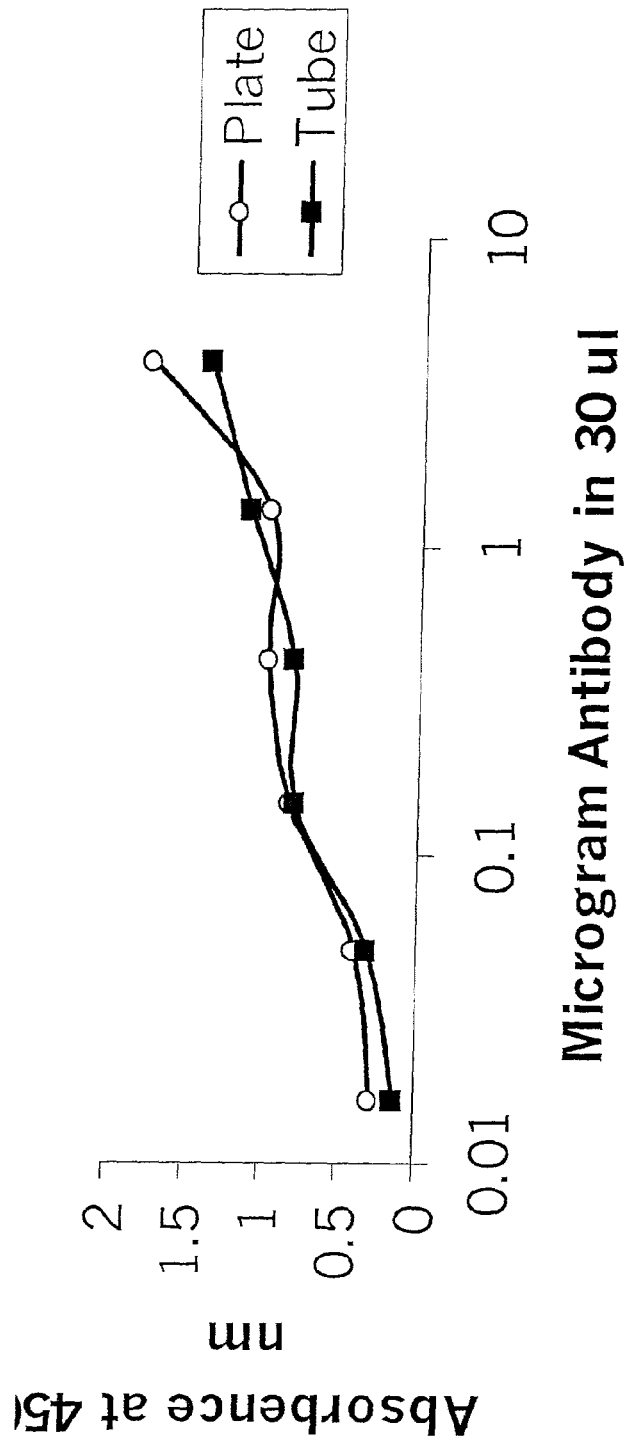
FIG. 2 is a graph of antibody (micrograms in 30 µl) versus absorbance at 450 nm. This shows the amount of coating by the antibody when different amounts of antibody are used.

This example demonstrates that Micro Amp tubes can be coated with antibody as efficiently as microtiter plates. Micro Amp polypropylene tubes (appropriate for use in ABI 7700 sequence detector) and polystyrene ELISA microtiter plates were coated with variable amounts of anti-biotin antibody. For this purpose, 40 µl of desired antibody, in 50 mM carbonate buffer pH 9.6, was incubated overnight at 4° C. in these tubes. Subsequent to incubation, any uncoated material was washed with 150 mM phosphate buffer saline, pH 7.2. Subsequent to washing, coated anti-biotin antibody was recognized by 1 µg/ml of biotin coupled horse reddish peroxidase (HRP). Subsequent to washing of unbound proteins, the relative amounts of bound HRP were detected by using OPD assay. After 10-15 min, the assay mixture was transferred from Micro Amp tubes to Costar plates and the absorbance of the assay mixture was evaluated at 450 nm using a plate reader. As shown in FIG. 2, both microtiter plates and Micro Amp tubes showed similar levels of antibody coating.

B. Example 2

Figure 4:
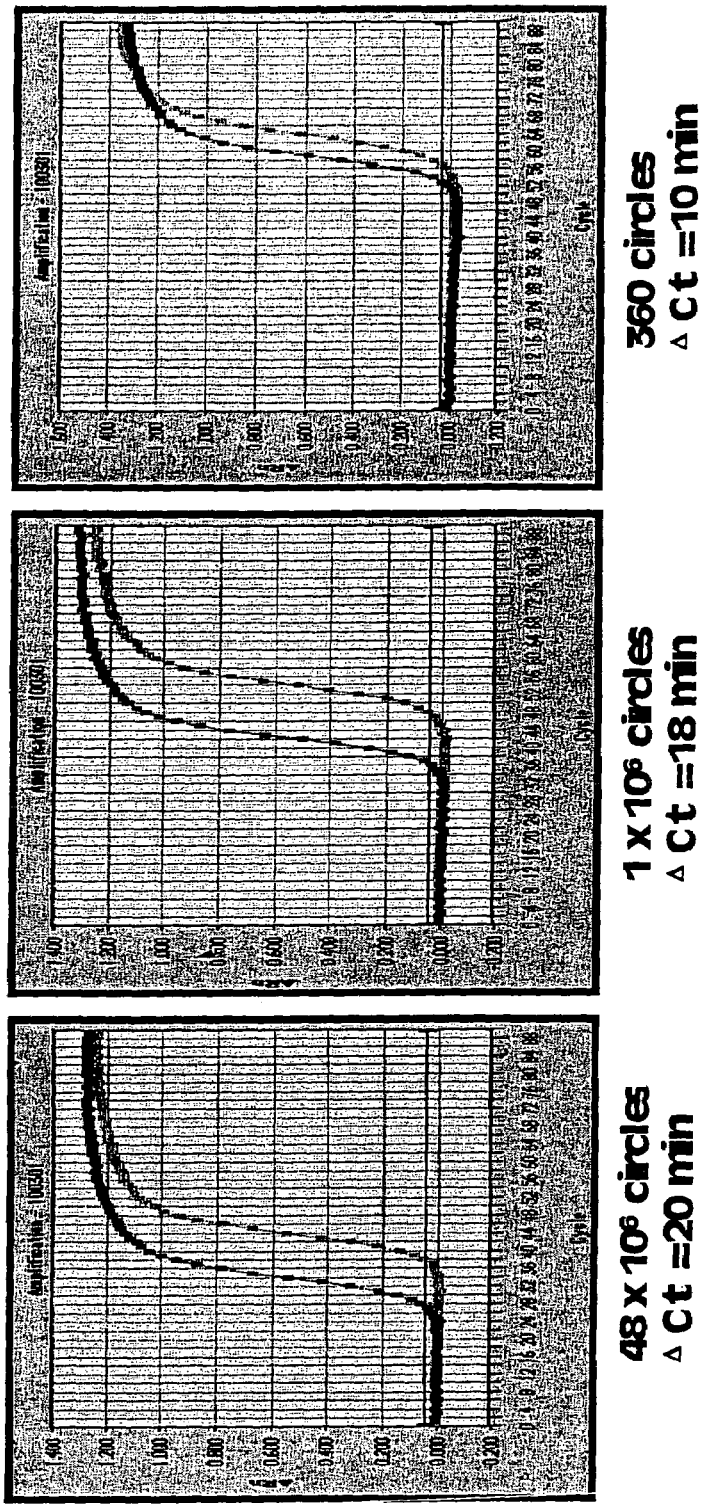
FIGS. 4A, 4B, and 4C are graphs of time (in "cycles," which are 2 minute time units) versus fluorescence. The difference in delta Ct when using different numbers of reporter binding agents is shown between the three graphs.

Detection of Amplification Target Circles, Captured on Antibody-coated Micro Amp Tubes, by Immuno ERCA Using ABI 7700 Sequence Detector Instrument This example demonstrates amplification and detection of captured amplification target circles. The strategy for this example is shown in FIG. 3. In this example, variable amounts of reporter binding molecules were used to assess, in part, the effect of the amount of reporter binding molecules on signal over background. Micro Amp tubes were coated, as described in Example 1, with 30 µl of 10 µg/ml of either anti-biotin antibody or mouse IgG. These antibodies serve as "analytes" in this example. Subsequent to washing, the tubes were blocked using blocking solution (blocker casein in PBS, Pierce Chemicals) and washed again with PBS carrying 0.05% Tween 20. In a separate tube, amplification target circle 1822oc88 was annealed to 3'-biotin labeled circle capture probe in 2×SSC. The amplification target circle/circle capture probe/biotin is a reporter binding molecule. The biotin is the specific binding molecule. Various amounts of circle capture probe annealed circles (freshly diluted in 30 µl PBS) were added to coated Micro Amp tubes and incubated at 37° C. for 1 hour. Unbound probe-annealed circles as well as probes were washed away using PBS. Trapped circles were detected by ERCA using TET linked Amplifluor™ as one of the two primers and real time detection of fluorescence in ABI 7700 sequence detector. This allowed real-time detection of amplification products as TET moieties emitted fluorescent signal after synthesis of complementary strands. 30 µl of the ERCA mix contained 5% tetramethyl ammonium oxlate, 400 µM dNTP mix, 1 µM each of the two primers, 8 units of Bst DNA polymerase (New England Biolabs, Mass.), and 1× modified ThermoPol buffer containing 20 mM Tris-HCl (pH 8.8), 10 mM KCl, 10 mM $(NH_4)_2SO_4$ and 0.1% Triton X-100. ERCA reactions were performed at 60° C. Histographic analysis of the amplification results is shown in FIG. 4. The graphs show fluorescence detected over time (the time units are labeled as "cycles" in the graphs although there was no cycling involved). Fluorescent signal is observed in assays containing the anti-biotin antibody "analyte" prior to signal seen in the control assays without analyte. FIG. 4 notes this difference in signal appearance as ΔCt. As can be seen, even when very few reporter binding molecules (360) were used, there was still an easily observable difference in the time of signal appearance.

C. Example 3

Detection of the Binding of Variable Number of Amplification Target Circles Using Fixed Number of Amplification Target Circles in Immuno ERCA with Amplifluors™

Figure 6:
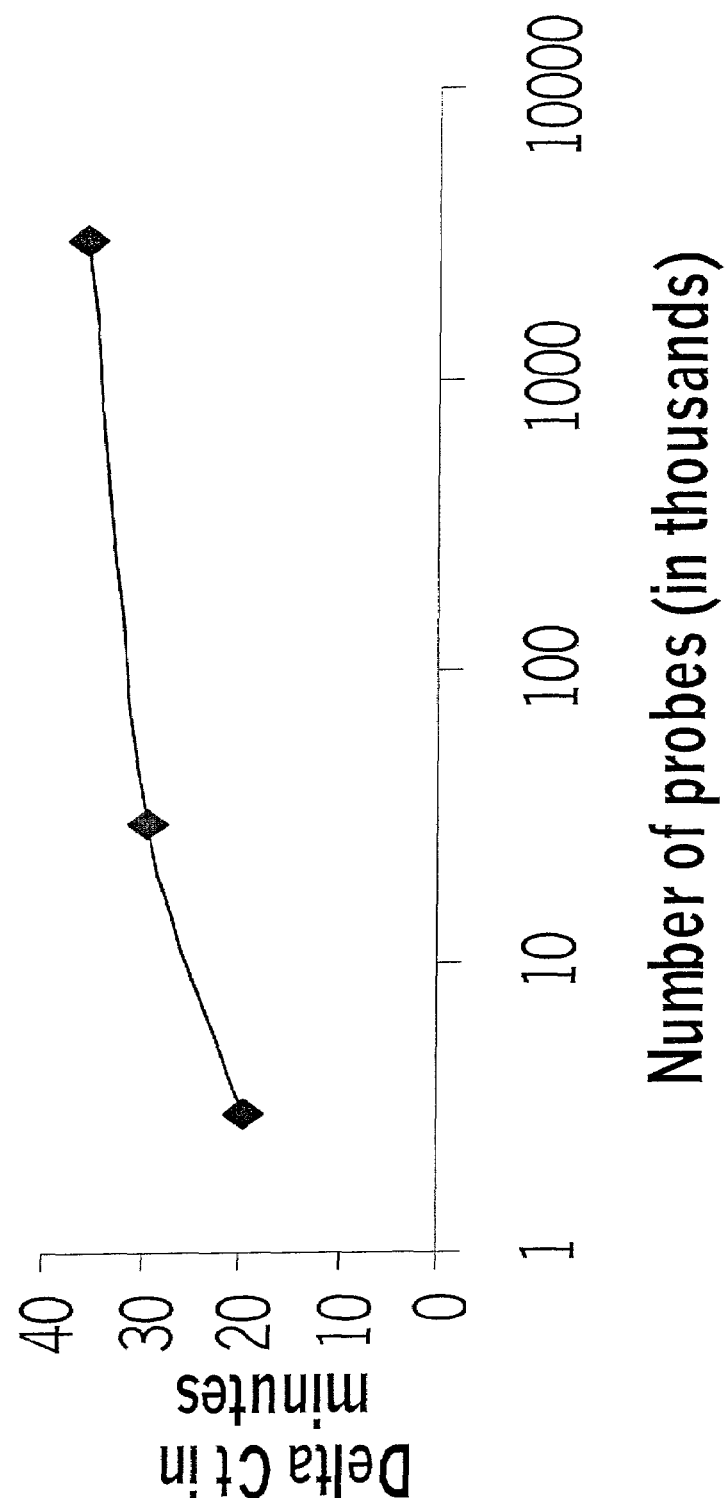
FIG. 6 is a graph of the number of circle capture probes used (in thousands) versus the change in counts (in minutes).

This example demonstrates detection binding of a fixed number of amplification target circles to a variable number of circle capture probes. The strategy for this example is shown in FIG. 5. Because the number of amplification target circles used were the same, the background caused by the circles was expected to be similar in all of the assays. Anti biotin antibody-coated or mouse IgG-coated Micro Amp tubes were used to incubate various amounts of 3'-biotin labeled circle capture probes, in PBS. Subsequent to the removal of unbound probes, $1\times10^6$ 1822oc88 amplification target circles, in 2×SSC, were used for annealing to antibody-bound circle capture probes at 37° C. for 1 hour. Subsequent to the washing of excess circles, probe-annealed circles were detected by ERCA as indicated before. Amplification products were detected in real time as TET moieties emitted fluorescent signal after synthesis of complementary strands. Difference in Ct values between anti biotin antibody-coated and mouse IgG-coated tubes at various for various amounts of circle capture probes are plotted in FIG. 6. The graph shows the difference in the time of fluorescent signal detection ($\Delta$Ct) using different amounts of circle capture probes. As can be seen, there was an easily observable difference in the time of signal appearance at all amounts of circle capture probe. These results also demonstrate that variations in the circle capture probe, bound to capture antibodies, can be successfully detected by immuno-ERCA.

D. Example 4

Detection of IL-8 Using Immuno-ERCA (ERCA-ELISA)

Figure 7:
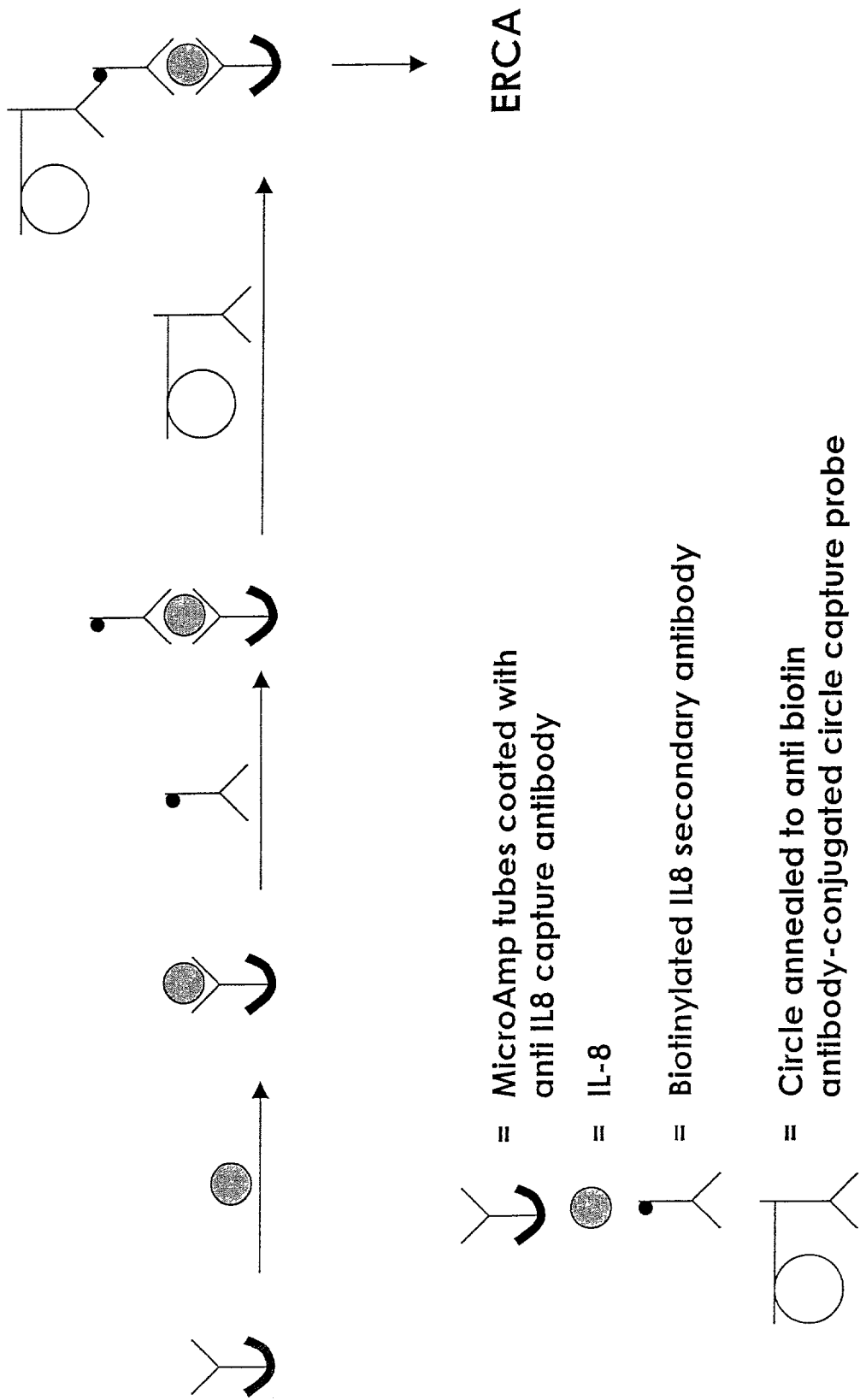
FIG. 7 is a diagram of an example of immunoRCA involving amplification target circles associated with specific binding molecules via base pairing to circle capture probes. Micro Amp tubes coated with anti-IL8 antibodies (analyte capture agents) are brought into contact with IL8 (analyte) and the IL8 binds to the antibodies. A biotinylated anti-IL8 antibody is brought into contact with the captured IL8 and they bind. Reporter binding molecules (comprising an anti-biotin antibody, a circle capture probe and an amplification target circle) are brought into contact with the biotinylated anti-IL8 antibody and they bind. This associates the reporter binding molecule with the analyte (IL8) indirectly (via the biotinylated anti-IL8 antibody). The amplification target circle is decoupled from the reporter binding molecule by disrupting the base pairing between the amplification target circle and the circle capture probe and amplified in ERCA.
Figure 8:
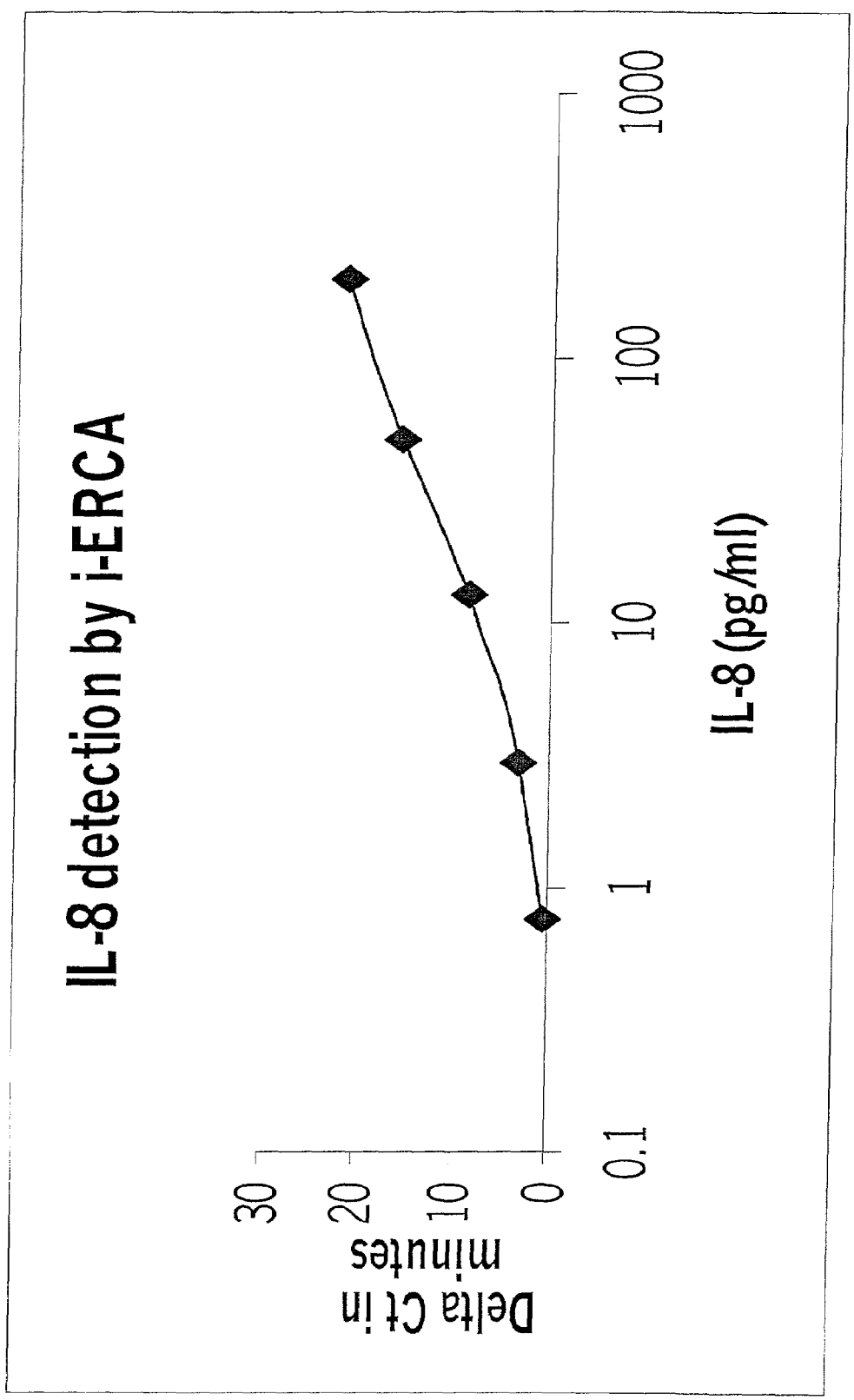
FIG. 8 is a graph of the amount of IL8 (in pg/ml) versus the change in counts (in minutes).
Figure 9:
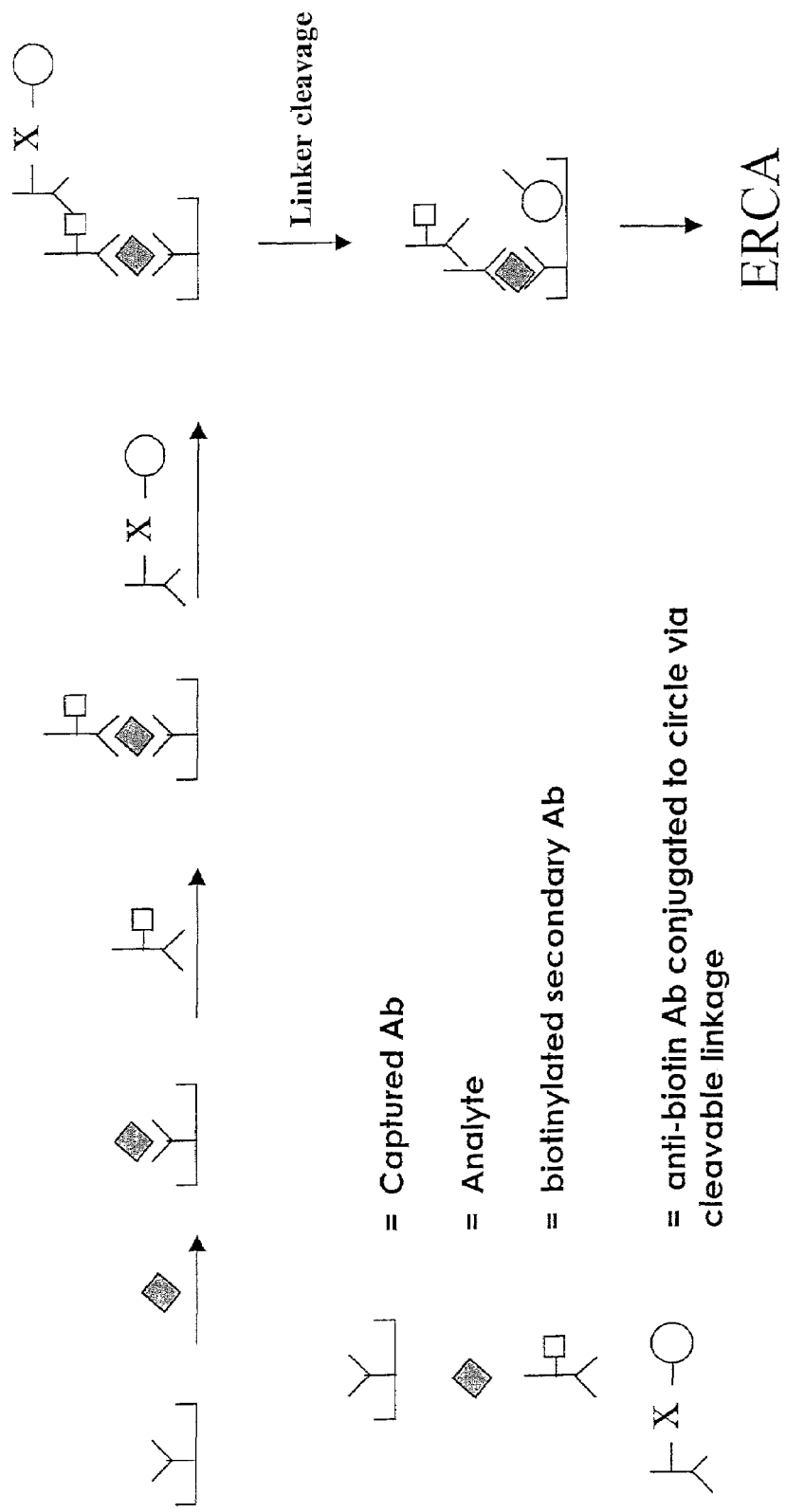
FIG. 9 is a diagram of an example of immunoRCA involving amplification target circles coupled to specific binding molecules via circle linkers having cleavable bonds. Anti-analyte antibodies (analyte capture agents) are brought into contact with analyte and the analyte binds to the antibodies. Biotinylated anti-analyte antibodies are brought into contact with the captured analyte and they bind. Reporter binding molecules (comprising an anti-biotin antibody, a circle linker containing a cleavable bond, and an amplification target circle) are brought into contact with the biotinylated anti-analyte antibody and they bind. This associates the reporter binding molecule with the analyte indirectly (via the biotinylated anti-analyte antibody). The amplification target circle is decoupled from the reporter binding molecule by cleaving the cleavable bond and the circle capture probe and amplified in ERCA.

This example demonstrates use of a form of the disclosed method to detect IL-8. The strategy for this example is shown in FIG. 7. Micro Amp tubes were coated with 40 µl of 10 µg/ml anti-IL-8 mouse mAb in 50 mM carbonate buffer, pH 9.6, at 4° C. for 12 hrs. Variable concentrations of IL-8 (40 µl) were incubated in these tubes, at 37° C., for 1 hr. Subsequent to the washing of unbound IL-8 molecules, 1 µg/ml of biotinylated anti-IL-8 secondary antibody (40 µl) was incubated at 37° C. for 1 hr. Subsequent to washing, the tubes were incubated with 40 µl of 10 ng/ml anti-biotin antibody that has been covalently conjugated with circle capture probe via its 3' end and is pre-annealed with the 1822in88 amplification target circle at 37° C. for 5 hrs. Trapped circles were detected by ERCA using FAM Amplifluors™ as described before. This allowed real-time detection of amplification products as FAM moieties emitted fluorescent signal after synthesis of complementary strands. Differences in $\Delta$Ct values between no IL-8 and various concentrations of IL-8, used in this assay, are plotted in FIG. 8. The graph shows the difference in the time of fluorescent signal detection ($\Delta$Ct) when different amounts of IL-8 were present. As can be seen, the $\Delta$Ct increases steadily as the amount of IL-8 increased.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method for detecting one or more analytes, the method comprising
   (a) bringing into contact one or more analyte samples and one or more reporter binding molecules, wherein each reporter binding molecule comprises a specific binding molecule and an amplification target circle, wherein each specific binding molecule interacts with an analyte directly or indirectly,
   incubating the analyte samples and the reporter binding molecules under conditions that promote interaction of the specific binding molecules and analytes, and
   separating the specific binding molecules that interact with the analytes from the specific binding molecules that do not interact with the analytes,
   (b) decoupling the amplification target circles associated with the analytes from the specific binding molecules,
   (c) bringing into contact the decoupled amplification target circles and one or more rolling circle replication primers, wherein the amplification target circles each comprise a single-stranded, circular DNA molecule comprising a primer complement portion, wherein the primer complement portion is complementary to at least one of the rolling circle replication primers, and
   incubating the rolling circle replication primers and amplification target circles under conditions that promote hybridization between the amplification target circles and the rolling circle replication primers,
   (d) incubating the rolling circle replication primers and amplification target circles under conditions that promote replication of the amplification target circles,
   wherein replication of the amplification target circles results in the formation of tandem sequence DNA, wherein detection of tandem sequence DNA indicates the presence of the corresponding analytes.

2. The method of claim 1, wherein at least one of the reporter binding molecules further comprises a circle capture probe, wherein the amplification target circle of the reporter binding molecule is associated with the reporter binding molecule via a non-covalent interaction with the circle capture probe.

3. The method of claim 2, wherein the non-covalent interaction is base pairing.

4. The method of claim 3, wherein decoupling of the amplification target circle is accomplished by disrupting the base pairing.

5. The method of claim 4, wherein the base pairing is disrupted by heating the reporter binding molecules.

6. The method of claim 2, wherein the circle capture probe comprises an oligonucleotide.

7. The method of claim 6, wherein the oligonucleotide cannot be extended.

8. The method of claim 7, wherein the oligonucleotide comprises a 3' end and a 5' end, wherein only the 5' end is free.

9. The method of claim 8, wherein the oligonucleotide is coupled to the specific binding molecule of the reporter binding molecule via the 3' end of the oligonucleotide.

10. The method of claim 8, wherein the 3' end of the oligonucleotide is blocked.

11. The method of claim 7, wherein the oligonucleotide is blocked.

12. The method of claim 1, wherein at least one of the reporter binding molecules further comprises a circle linker, wherein the amplification target circle of the reporter binding molecule is coupled to the reporter binding molecule via the circle linker.

13. The method of claim 12, wherein the circle linker comprises a cleavable bond.

14. The method of claim 13, wherein decoupling of the amplification target circle is accomplished by cleaving the cleavable bond.

15. The method of claim 14, wherein the cleavable bond is cleaved by treatment with a reducing agent.

16. The method of claim 15, wherein the cleavable bond is a disulfide bond.

17. The method of claim 16, wherein the circle linker comprises dithiobis succinimidyl propionate, dimethyl 3,3'-dithiobispropionimidate, dithio-bis-maleimidoethane, 3,3'-dithiobis sulfosuccinimidyl propionate, succinimidyl 6-[3-(2-pyridyldithio)-propionamido]hexonate, or N-succinimidyl 3-[2-pyridyldithio]propionate.

18. The method of claim 14, wherein the cleavable bond is cleaved by treatment with periodate.

19. The method of claim 18, wherein the cleavable bond is a dihydroxy bond.

20. The method of claim 19, wherein the circle linker comprises 1,4bis-maleimidyl-2,3-dihydroxybutane, disuccinimidyl tartrate, or disulfosuccinimidyl tartrate.

21. The method of claim 12, wherein the circle linker is coupled to the amplification target circle via a reactive group on the amplification target circle.

22. The method of claim 21, wherein the reactive group is an allyl amino group.

23. The method of claim 1, wherein a plurality of reporter binding molecules are brought into contact with the one or more analyte samples.

24. The method of claim 1, wherein a plurality of analyte samples are brought into contact with the one or more reporter binding molecules.

25. The method of claim 1, wherein at least one of the analytes is a protein or peptide.

26. The method of claim 1, wherein at least one of the analytes is a lipid, glycolipid, or proteoglycan.

27. The method of claim 1, wherein at least one of the analytes is from a human source.

28. The method of claim 1, wherein at least one of the analytes is from a non-human source.

29. The method of claim 1, wherein none of the analytes are nucleic acids.

30. The method of claim 1, wherein the specific binding molecules that interact with the analytes are separated by
bringing into contact at least one of the analyte samples and one or more analyte capture agents, wherein each analyte capture agent interacts with an analyte directly or indirectly, wherein at least one analyte, if present in the analyte sample, interacts with at least one analyte capture agent, and
separating analyte capture agents from the analyte samples, thus separating specific binding molecules that interact with the analytes from the analyte samples.

31. The method of claim 30, wherein at least one analyte capture agent is associated with a solid support, wherein analytes that interact with the analyte capture agent associated with a solid support become associated with the solid support.

32. The method of claim 31, wherein the solid support comprise one or more reaction chambers, wherein a plurality of the analyte capture agents are located in the same reaction chamber on the solid support.

33. The method of claim 31, wherein a plurality of reporter binding molecules are brought into contact with one or more analyte samples, wherein two or more of the amplification target circles are replicated in the same reaction chamber of the solid support, wherein the amplification target circles replicated in the same reaction chamber of the solid support are different, wherein each different amplification target circle produces a different tandem sequence DNA,
wherein the presence or absence of different analytes is indicated by the presence or absence of corresponding tandem sequence DNA.

34. The method of claim 33, wherein replication of each different amplification target circle is primed by a different one of the rolling circle replication primers.

35. The method of claim 31, wherein the solid support comprises acrylamide, agarose, cellulose, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, or polyamino acids.

36. The method of claim 30, further comprising bringing into contact at least one of the analyte samples and at least one of the reporter binding molecules with at least one accessory molecule, wherein the accessory molecule affects the interaction of at least one of the analytes and at least one of the specific binding molecules or at least one of the analyte capture agents.

37. The method of claim 36, wherein the accessory molecule is brought into contact with at least one of the analyte samples, at least one of the reporter binding molecules, or both, prior to, simultaneous with, or following step (a).

38. The method of claim 36, wherein at least one analyte capture agent is associated with a solid support, wherein the accessory molecule is associated with the solid support.

39. The method of claim 38, wherein the accessory molecule is associated with the solid support by bringing the accessory molecule into contact with the solid support prior to, simultaneous with, or following step (a).

40. The method of claim 36, wherein the accessory molecule is a protein kinase, a protein phosphatase, an enzyme, or a compound.

41. The method of claim 36, wherein the accessory molecule is a molecule of interest, wherein one or more of the analytes are test molecules, wherein interactions of the test molecules with the molecule of interest are detected.

42. The method of claim 36, wherein at least one of the analytes is a molecule of interest, wherein the accessory molecule is a test molecule, wherein interactions of the test molecule with the molecule of interest are detected.

43. The method of claim 30, wherein the analyte samples include one or more first analyte samples and one or more second analyte samples, wherein the reporter binding molecules include one or more first reporter binding molecules and one or more second reporter binding molecules, the method further comprising, following step (a) and prior to bringing the analyte samples and the solid support into contact, mixing one or more of the first analyte samples and one or more of the second analyte samples, wherein for each first reporter binding molecule there is a matching second reporter binding molecule, wherein the specific binding molecules of the first reporter binding molecules interacts with the same analyte as the specific binding molecules of the matching second reporter binding molecule, wherein the amplification target circle of each different reporter binding molecule is different, wherein each different amplification target circle produces a different tandem sequence DNA, wherein the presence or absence of the same analyte in different analyte samples is indicated by the presence or absence of corresponding tandem sequence DNA.

44. The method of claim 43, wherein replication of each different amplification target circle is primed by a different one of the rolling circle replication primers.

45. The method of claim 44, wherein the tandem sequence DNA corresponding to one of the analytes and produced in association with a first reporter binding molecule is in the same location on the solid support as tandem sequence DNA corresponding to the same analyte and produced in association with the matching second reporter binding molecule, wherein the presence or absence of the same analyte in different analyte samples is indicated by the presence or absence of corresponding tandem sequence DNA.

46. The method of claim 30, wherein at least one of the analyte capture agents is a molecule of interest, wherein one or more of the analytes are test molecules, wherein interactions of the test molecules with the molecule of interest are detected.

47. The method of claim 30, wherein at least one of the analytes is a molecule of interest, wherein one or more of the analyte capture agents are test molecules, wherein interactions of the test molecules with the molecule of interest are detected.

48. The method of claim 1, wherein a plurality of reporter binding molecules are brought into contact with one or more analyte samples, wherein two or more of the amplification target circles are replicated in the same reaction, wherein the amplification target circles replicated in the same reaction are different, wherein each different amplification target circle produces a different tandem sequence DNA, wherein the presence or absence of different analytes is indicated by the presence or absence of corresponding tandem sequence DNA.

49. The method of claim 48, wherein replication of each different amplification target circle is primed by a different one of the rolling circle replication primers.

50. The method of claim 1, further comprising, prior to, simultaneous with, or following step (a), bringing into contact one or more first analyte capture agents and one or more first analyte samples, and bringing into contact one or more second analyte capture agents and one or more second analyte samples, wherein each analyte capture agent comprises an analyte interaction portion and a capture portion, wherein for each first analyte capture agent there is a matching second analyte capture agent, wherein the analyte interaction portions of the first analyte capture agents interact with the same analyte as the analyte interaction portions of the matching second analyte capture agents, wherein the capture portions of the first and second analyte capture agents each interact with a specific binding molecule of one or more of the reporter binding molecules, wherein the capture portions of the first analyte capture agents interact with different specific binding molecules than the capture portions of the matching second analyte capture agents, wherein each different specific binding molecule is part of a different one of the reporter binding molecules, wherein the amplification target circle of each different reporter binding molecule is different, wherein replication of each different amplification target circle is primed by a different one of the rolling circle replication primers, wherein each different amplification target circle produces a different tandem sequence DNA, wherein the amplification target circle of a reporter binding molecule that comprises a specific binding molecule that interacts with an analyte capture agent corresponds to the analyte capture agent, wherein the presence or absence of the same analyte in different analyte samples is indicated by the presence or absence of corresponding tandem sequence DNA.

51. The method of claim 50, further comprising mixing one or more of the first analyte samples and one or more of the second analyte samples.

52. The method of claim 50, further comprising mixing the one or more first analyte capture agents and the one or more second analyte capture agents.

53. The method of claim 52, wherein mixing the one or more first analyte capture agents and the one or more second analyte capture agents is accomplished by associating, simultaneously or sequentially, the one or more first analyte capture agents and the one or more second analyte capture agents with the same solid support.

54. The method of claim 50, wherein the tandem sequence DNA corresponding to one of the analytes and produced in association with a first analyte capture agent is in the same location as, and is simultaneously detected with, tandem sequence DNA corresponding to the same analyte and produced in association with the matching second analyte capture agent, wherein the presence or absence of the same analyte in different analyte samples is indicated by the presence or absence of corresponding tandem sequence DNA.

55. The method of claim 50, wherein the capture portion of each first analyte capture agent is the same, wherein the reporter binding molecules corresponding to the first analyte capture agents are the same, wherein the amplification target circles corresponding to the first analyte capture agents are the same, wherein the capture portion of each second analyte capture agent is the same, wherein the reporter binding molecules corresponding to the second analyte capture agents are the same, wherein the amplification target circles corresponding to the second analyte capture agents are the same.

56. The method of claim 1, wherein at least one of the specific binding molecules is an antibody specific for at least one of the analytes.

57. The method of claim 1, wherein at least one of the specific binding molecules is a molecule that specifically binds to at least one of the analytes.

58. The method of claim 1, wherein at least one of the specific binding molecules is a molecule that specifically binds to at least one of the analytes in combination with an accessory molecule.

59. The method of claim 1, wherein the specific binding molecules and analytes interact by binding to each other directly or indirectly.

60. The method of claim 1, wherein at least one accessory molecule is brought into contact with at least one of the analyte samples and at least one of the reporter binding molecules, wherein the accessory molecule affects the interaction of at least one of the analytes and at least one of the specific binding molecules or at least one of the analyte capture agents.

61. The method of claim 60, wherein the accessory molecule competes with the interaction of at least one of the specific binding molecules or at least one of the analyte capture agents.

62. The method of claim 61, wherein the accessory molecule is an analog of at least one of the analytes.

63. The method of claim 60, wherein the accessory molecule facilitates the interaction of at least one of the specific binding molecules or at least one of the analyte capture agents.

64. The method of claim 60, wherein the accessory molecule is brought into contact with at least one of the analyte samples, at least one of the reporter binding molecules, or both, prior to, simultaneous with, or following step (a).

65. The method of claim 60, wherein the accessory molecule is a protein kinase, a protein phosphatase, an enzyme, or a compound.

66. The method of claim 60, wherein the accessory molecule is at least 20% pure.

67. The method of claim 60, wherein the accessory molecule is at least 50% pure.

68. The method of claim 60, wherein the accessory molecule is at least 80% pure.

69. The method of claim 60, wherein the accessory molecule is at least 90% pure.

70. The method of claim 1, wherein at least one of the analytes is associated with a solid support.

71. The method of claim 70, wherein the solid support comprises one or more reaction chambers, wherein a plurality of the analytes associated with the solid support are associated with the solid support in the same reaction chamber.

72. The method of claim 70, wherein at least one of the analytes associated with the solid support is associated with the solid support indirectly.

73. The method of claim 72, wherein the analytes associated with the solid support interact with analyte capture agents, and wherein the analyte capture agents are associated with the solid support thereby indirectly associating the analytes with the solid support.

74. The method of claim 1, wherein at least one specific binding molecule interacts with at least one analyte indirectly.

75. The method of claim 74, wherein the analyte interacts with an analyte capture agent, and wherein the specific binding molecule interacts with the analyte capture agent thereby indirectly associating the specific binding molecule with the analyte.

76. The method of claim 1, wherein at least one of the analytes is a modified form of another analyte, wherein the specific binding molecule of at least one of the reporter binding molecules interacts, directly or indirectly, with the analyte that is a modified form of the other analyte, and wherein the specific binding molecule of another reporter binding molecule interacts, directly or indirectly, with the other analyte.

77. The method of claim 76, wherein the analytes are proteins, wherein the modification of the modified form of the other analyte is a post-translational modification.

78. The method of claim 77, wherein the modification is phosphorylation or glycosylation.

79. The method of claim 1, wherein detection of the tandem sequence DNA is accomplished by
mixing a set of detection probes with the tandem sequence DNA under conditions that promote hybridization between the tandem sequence DNA and the detection probes.

80. The method of claim 79, wherein a plurality of different tandem sequence DNAs are detected separately and simultaneously via multiplex detection.

81. The method of claim 80, wherein the set of detection probes is labeled using combinatorial multicolor coding.

82. The method of claim 1, further comprising, simultaneous with, or following, step (d),
bringing into contact a secondary DNA strand displacement primer and the tandem sequence DNA, and incubating under conditions that promote (i) hybridization between the tandem sequence DNA and the secondary DNA strand displacement primer, and (ii) replication of the tandem sequence DNA, wherein replication of the tandem sequence DNA results in the formation of secondary tandem sequence DNA.

83. The method of claim 82, wherein the tandem sequence DNA, secondary tandem sequence DNA, or both, are detected during replication of the amplification target circles.

84. The method of claim 83, wherein the tandem sequence DNA, secondary tandem sequence DNA, or both, are detected by detecting fluorescent moieties incorporated into the tandem sequence DNA, secondary tandem sequence DNA, or both.

85. The method of claim 82, wherein the tandem sequence DNA, secondary tandem sequence DNA, or both, are detected during replication of the tandem sequence DNA.

86. The method of claim 82, wherein at least one of the rolling circle replication primers is a fluorescent quenched primer.

87. The method of claim 82, wherein at least one of the secondary DNA strand displacement primers is a fluorescent quenched primer.

88. The method of claim 82, wherein at least one of the rolling circle replication primers and at least one of the secondary DNA strand displacement primers are fluorescent quenched primers.

89. The method of claim 82, wherein the tandem sequence DNA, secondary tandem sequence DNA, or both, are detected by detecting fluorescent moieties incorporated into the tandem sequence DNA.

90. The method of claim 82, wherein the secondary tandem sequence DNA is replicated to form higher order tandem sequence DNA.

91. The method of claim 90, wherein the amplification target circles, the tandem sequence DNA, and the secondary tandem sequence DNA are replicated simultaneously.

92. The method of claim 90, wherein the tandem sequence DNA, secondary tandem sequence DNA, higher order tandem sequence DNA, or a combination, is detected during replication of the amplification target circles.

93. The method of claim 90, wherein the tandem sequence DNA, secondary tandem sequence DNA, higher order tandem sequence DNA, or a combination, is detected by detecting fluorescent moieties incorporated into the tandem sequence DNA, secondary tandem sequence DNA, higher order tandem sequence DNA, or a combination.

94. The method of claim 90, wherein the tandem sequence DNA, secondary tandem sequence DNA, higher order tandem sequence DNA, or a combination, is detected during replication of the tandem sequence DNA.

95. The method of claim 90, wherein at least one of the rolling circle replication primers is a fluorescent quenched primer.

96. The method of claim 90, wherein at least one of the secondary DNA strand displacement primers is a fluorescent quenched primer.

97. The method of claim 90, wherein at least one of the rolling circle replication primers and at least one of the secondary DNA strand displacement primers are fluorescent quenched primers.

98. The method of claim 90, wherein the tandem sequence DNA, secondary tandem sequence DNA, higher order tandem sequence DNA, or a combination, is detected by detecting fluorescent moieties incorporated into the tandem sequence DNA.

99. The method of claim 1, wherein the tandem sequence DNA is detected during replication of the amplification target circles.

100. The method of claim 99, wherein the tandem sequence DNA is detected by detecting fluorescent moieties incorporated into the tandem sequence DNA.

101. The method of claim 1, wherein at least one of the rolling circle replication primers is a fluorescent quenched primer.

102. The method of claim 1, wherein the tandem sequence DNA is detected by detecting fluorescent moieties incorporated into the tandem sequence DNA.

103. The method of claim 1, wherein the reporter binding molecules are at least 20% pure.

104. The method of claim 1, wherein the reporter binding molecules are at least 50% pure.

105. The method of claim 1, wherein the reporter binding molecules are at least 80% pure.

106. The method of claim 1, wherein the reporter binding molecules are at least 90% pure.

107. A method for detecting one or more analytes, the method comprising
  (a) bringing into contact one or more analyte samples and one or more analyte capture agents, wherein each analyte capture agent interacts with an analyte directly or indirectly, wherein at least one analyte, if present in the analyte sample, interacts with at least one analyte capture agent,
  incubating the analyte samples and the analyte capture agents under conditions that promote interaction of the analyte capture agents and analytes,
  (b) bringing into contact at least one of the analyte samples and one or more reporter binding molecules, wherein each reporter binding molecule comprises a specific binding molecule and an amplification target circle, wherein each specific binding molecule interacts with an analyte capture agent directly or indirectly,
  incubating the analyte samples and the reporter binding molecules under conditions that promote interaction of the specific binding molecules and analyte capture agents, and
  separating the specific binding molecules that interact with the analyte capture agents from the specific binding molecules that do not interact with the analyte capture agents,
  (c) decoupling the amplification target circles associated with the analytes from the specific binding molecules,
  (d) bringing into contact the decoupled amplification target circles and one or more rolling circle replication primers, wherein the amplification target circles each comprise a single-stranded, circular DNA molecule comprising a primer complement portion, wherein the primer complement portion is complementary to at least one of the rolling circle replication primers, and
  incubating the rolling circle replication primers and amplification target circles under conditions that promote hybridization between the amplification target circles and the rolling circle replication primers,
  (e) incubating the rolling circle replication primers and amplification target circles under conditions that promote replication of the amplification target circles,
  wherein replication of the amplification target circles results in the formation of tandem sequence DNA, wherein detection of tandem sequence DNA indicates the presence of the corresponding analytes.

108. A method for detecting one or more analytes, the method comprising
  (a) treating one or more analyte samples so that one or more analytes are modified,
  (b) bringing into contact at least one of the analyte samples and one or more reporter binding molecules, wherein each reporter binding molecule comprises a specific binding molecule and an amplification target circle, wherein each specific binding molecule interacts with a modified analyte directly or indirectly,
  incubating the analyte samples and the reporter binding molecules under conditions that promote interaction of the specific binding molecules and modified analytes, and
  separating the specific binding molecules that interact with the modified analytes from the specific binding molecules that do not interact with the modified analytes,
  (c) decoupling the amplification target circles associated with the analytes from the specific binding molecules,
  (d) bringing into contact the decoupled amplification target circles and one or more rolling circle replication primers, wherein the amplification target circles each comprise a single-stranded, circular DNA molecule comprising a primer complement portion, wherein the primer complement portion is complementary to at least one of the rolling circle replication primers, and
  incubating the rolling circle replication primers and amplification target circles under conditions that promote hybridization between the amplification target circles and the rolling circle replication primers,
  (e) incubating the rolling circle replication primers and amplification target circles under conditions that promote replication of the amplification target circles,
  wherein replication of the amplification target circles results in the formation of tandem sequence DNA, wherein detection of tandem sequence DNA indicates the presence of the corresponding modified analytes.

109. The method of claim 108, wherein all of the analytes are modified by associating a modifying group to the analytes, wherein the modifying group is the same for all of the analytes, wherein all of the specific binding molecules interact with the modifying group.

110. A method for detecting one or more analytes, the method comprising
  (a) bringing into contact one or more analyte samples and a set of analyte capture agents, a set of accessory molecules, or both, wherein each analyte capture agent interacts with an analyte directly or indirectly, (b) prior to, simultaneously with, or following step (a), bringing into contact at least one of the analyte samples and one or more reporter binding molecules, wherein each reporter binding molecule comprises a specific binding molecule and an amplification target circle, wherein each specific binding molecule interacts with an analyte directly or indirectly, wherein each accessory molecule affects the interaction of at least one of the analytes and at least one of the specific binding molecules or at least one of the analyte capture agents, (c) simultaneous with, or following, steps (a) and (b), incubating the analyte samples, the analyte capture agents, the accessory molecules, and the reporter binding molecules under conditions that promote interaction of the specific binding molecules, analytes, analyte capture agents, and accessory molecules, and separating the specific binding molecules that interact with the analytes from the specific binding molecules that do not interact with the analytes, decoupling the amplification target circles associated with the analytes from the specific binding molecules, (d) bringing into contact the decoupled amplification target circles and one or more rolling circle replication primers, wherein the amplification target circles each comprise a single-stranded, circular DNA molecule comprising a primer complement portion, wherein the primer complement portion is complementary to at least one of the rolling circle replication primers, and incubating the rolling circle replication primers and amplification target circles under conditions that promote hybridization between the amplification target circles and the rolling circle replication primers, (e) incubating the reporter binding molecules and amplification target circles under conditions that promote replication of the amplification target circles, wherein replication of the amplification target circles results in the formation of tandem sequence DNA, wherein detection of tandem sequence DNA indicates the presence of the corresponding analytes.

111. The method of claim 110, wherein the analyte capture agents are immobilized on a solid support, wherein the solid support comprises one or more reaction chambers, wherein a plurality of the analyte capture agents are immobilized in the same reaction chamber of the solid support.

112. The method of claim 111, wherein the analyte capture agents are immobilized to the solid support at a density exceeding 400 different analyte capture agents per cubic centimeter.

113. The method of claim 111, wherein the analyte capture agents are peptides.

114. The method of claim 113, wherein each of the different peptides is at least 4 amino acids in length.

115. The method of claim 114, wherein each different peptide is from about 4 to about 20 amino acids in length.

116. The method of claim 114, wherein each different peptide is at least 10 amino acids in length.

117. The method of claim 114, wherein each different peptide is at least 20 amino acids in length.

118. The method of claim 111, wherein the solid support comprises a plurality of reaction chambers.

119. The method of claim 111, wherein the solid support comprises acrylamide, agarose, cellulose, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, or polyamino acids.

120. The method of claim 111, wherein the analyte capture agents in the reaction chambers are at least 20% pure.

121. The method of claim 111, wherein the analyte capture agents in the reaction chambers are at least 50% pure.

122. The method of claim 111, wherein the analyte capture agents in the reaction chambers are at least 80% pure.

123. The method of claim 111, wherein the analyte capture agents in the reaction chambers are at least 90% pure.

124. A method for detecting one or more analytes, the method comprising bringing into contact one or more analyte samples and one or more reporter binding molecules, wherein each reporter binding molecule comprises a specific binding molecule and an amplification target circle, wherein each specific binding molecule can interact with an analyte directly or indirectly, separating the specific binding molecules that interact with the analytes from the specific binding molecules that do not interact with the analytes, decoupling the amplification target circles associated with the analytes from the specific binding molecules, replicating the decoupled amplification target circles, wherein replication of the amplification target circles results in the formation of tandem sequence DNA, secondary tandem sequence DNA, and higher order tandem sequence DNA, wherein detection of tandem sequence DNA, secondary tandem sequence DNA, and higher order tandem sequence DNA, or a combination, indicates the presence of the corresponding analytes.

125. The method of claim 124, wherein the amplification target circles, the tandem sequence DNA, and the secondary tandem sequence DNA are replicated simultaneously.

126. The method of claim 124, wherein the tandem sequence DNA, secondary tandem sequence DNA, higher order tandem sequence DNA, or a combination, is detected during replication of the amplification target circles.

127. The method of claim 124, wherein the tandem sequence DNA, secondary tandem sequence DNA, higher order tandem sequence DNA, or a combination, is detected by detecting fluorescent moieties incorporated into the tandem sequence DNA, secondary tandem sequence DNA, higher order tandem sequence DNA, or a combination.

128. The method of claim 124, wherein the tandem sequence DNA, secondary tandem sequence DNA, higher order tandem sequence DNA, or a combination, is detected during replication of the tandem sequence DNA.

129. The method of claim 124, wherein at least one of the rolling circle replication primers is a fluorescent quenched primer.

130. The method of claim 124, wherein at least one of the secondary DNA strand displacement primers is a fluorescent quenched primer.

131. The method of claim 124, wherein at least one of the rolling circle replication primers and at least one of the secondary DNA strand displacement primers are fluorescent quenched primers.

132. The method of claim 124, wherein the tandem sequence DNA, secondary tandem sequence DNA, higher order tandem sequence DNA, or a combination, is detected by detecting fluorescent moieties incorporated into the tandem sequence DNA.

133. A method for detecting one or more analytes, the method comprising bringing into contact one or more analyte samples and one or more reporter binding molecules, wherein each reporter binding molecule comprises a specific binding molecule and an amplification target circle, wherein each specific binding molecule can interact with an analyte directly or indirectly, separating the specific binding molecules that interact with the analytes from the specific binding molecules that do not interact with the analytes, decoupling the amplification target circles associated with the analytes from the specific binding molecules, replicating the decoupled amplification target circles, wherein replication of the amplification target circles results in the formation of tandem sequence DNA, wherein detection of tandem sequence DNA indicates the presence of the corresponding analytes.

134. A method for detecting one or more analytes, the method comprising bringing into contact one or more analyte samples and one or more analyte capture agents, wherein each analyte capture agents can interact with an analyte directly or indirectly, bringing into contact at least one of the analyte samples and one or more reporter binding molecules, wherein each reporter binding molecule comprises a specific binding molecule and an amplification target circle, wherein each specific binding molecule can interact with an analyte capture agent directly or indirectly, separating the specific binding molecules that interact with the analyte capture agents from the specific binding molecules that do not interact with the analyte capture agents, decoupling the amplification target circles associated with the analytes from the specific binding molecules, replicating the decoupled amplification target circles, wherein replication of the amplification target circles results in the formation of tandem sequence DNA, wherein detection of tandem sequence DNA indicates the presence of the corresponding analytes.

135. A method for detecting one or more analytes, the method comprising treating one or more analyte samples so that one or more analytes are modified, bringing into contact at least one analyte samples and one or more reporter binding molecules, wherein each reporter binding molecule comprises a specific binding molecule and an amplification target circle, wherein each specific binding molecule can interact with a modified analyte directly or indirectly, separating the specific binding molecules that interact with the modified analytes from the specific binding molecules that do not interact with the modified analytes, decoupling the amplification target circles associated with the analytes from the specific binding molecules, replicating the decoupled amplification target circles, wherein replication of the amplification target circles results in the formation of tandem sequence DNA, wherein detection of tandem sequence DNA indicates the presence of the corresponding modified analytes.

136. A method for detecting one or more analytes, the method comprising bringing into contact one or more analyte samples and a set of analyte capture agents, a set of accessory molecules, or both, wherein each analyte capture agent can interact with an analyte directly or indirectly, bringing into contact at least one of the analyte samples and one or more reporter binding molecules, wherein each reporter binding molecule comprises a specific binding molecule and an amplification target circle, wherein each specific binding molecule can interact with an analyte directly or indirectly, wherein each accessory molecule can affect the interaction of at least one of the analytes and at least one of the specific binding molecules or at least one of the analyte capture agents, separating the specific binding molecules that interact with the analytes from the specific binding molecules that do not interact with the analytes, decoupling the amplification target circles associated with the analytes from the specific binding molecules, replicating the decoupled amplification target circles, wherein replication of the amplification target circles results in the formation of tandem sequence DNA, wherein detection of tandem sequence DNA indicates the presence of the corresponding analytes.

* * * * *